US012631589B2

(12) United States Patent
Bashir et al.

(10) Patent No.: US 12,631,589 B2
(45) Date of Patent: May 19, 2026

(54) LABEL FREE ANALYTE DETECTION BY ELECTRONIC DESALTING AND FIELD EFFECT TRANSISTORS

(71) Applicant: The Board of Trustees of the University of Illinois, Urbana, IL (US)

(72) Inventors: Rashid Bashir, Champaign, IL (US); Vikhram Vilasur Swaminathan, Redwood City, CA (US); Bobby Reddy, Jr., Savoy, IL (US); Eric M. Salm, Champaign, IL (US); Carlos Duarte-Guevara, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 780 days.

(21) Appl. No.: 16/690,032

(22) Filed: Nov. 20, 2019

(65) Prior Publication Data

US 2020/0103370 A1 Apr. 2, 2020

Related U.S. Application Data

(62) Division of application No. 15/128,879, filed as application No. PCT/US2015/023101 on Mar. 27, 2015, now Pat. No. 10,527,579.

(Continued)

(51) Int. Cl.
*G01N 27/414* (2006.01)
*G01N 33/543* (2006.01)

(52) U.S. Cl.
CPC ..... *G01N 27/4145* (2013.01); *G01N 27/4146* (2013.01); *G01N 33/5438* (2013.01)

(58) Field of Classification Search
CPC ........... G01N 27/4145; G01N 27/4146; G01N 33/5438
See application file for complete search history.

(56) References Cited

U.S. PATENT DOCUMENTS 4,180,771 A 12/1979 Guckel
6,284,117 B1 9/2001 Smolko et al.
(Continued)

FOREIGN PATENT DOCUMENTS

WO WO 2012/078340 A1 6/2012
WO WO 2013/016486 A1 1/2013
(Continued)

OTHER PUBLICATIONS

Shinwari, M. Waleed, et al. "Microfabricated reference electrodes and their biosensing applications." Sensors 10.3 (2010): 1679-1715. (Year: 2010).*

(Continued)

*Primary Examiner* — Robert J Eom
(74) *Attorney, Agent, or Firm* — Leydig, Voit & Mayer, Ltd.

(57) ABSTRACT

Provided are methods and devices for the label free detection of analytes in solution, including analytes suspended in a biological fluid. A field effect transistor (FET) is positioned in close proximity to a paired set of reference electrodes and the reference electrodes electrically biased to provide desalting and a stable gate voltage to the FET. In this manner, charged ions are depleted in the sensing region of the sensor and device sensitivity to analyte detection improved by the removal of charge that otherwise interferes with measurement. Also provided are methods and systems providing increased in reference electrode surface area and/or decrease in droplet volume to further improve label-free detection of analytes.

17 Claims, 62 Drawing Sheets

Related U.S. Application Data

(60) Provisional application No. 62/007,808, filed on Jun. 4, 2014, provisional application No. 61/972,148, filed on Mar. 28, 2014.

(56) References Cited

U.S. PATENT DOCUMENTS

| | | | |
|---|---|---|---|
| 8,377,280 | B2 | 2/2013 | Johnson |
| 9,250,113 | B2 | 2/2016 | Bashir et al. |
| 9,376,713 | B2 | 6/2016 | Bashir et al. |
| 9,433,943 | B2 | 9/2016 | Bashir et al. |
| 9,835,634 | B2 | 12/2017 | Bashir et al. |
| 10,527,579 | B2 | 1/2020 | Bashir et al. |
| 2007/0264623 | A1 | 11/2007 | Wang et al. |
| 2008/0280776 | A1 | 11/2008 | Bashir et al. |
| 2009/0142825 | A1 | 6/2009 | Murray et al. |
| 2010/0140096 | A1 | 6/2010 | Yang et al. |
| 2011/0086352 | A1 | 4/2011 | Bashir et al. |
| 2011/0279130 | A1 | 11/2011 | Reccius et al. |
| 2012/0021918 | A1 | 1/2012 | Bashir et al. |
| 2012/0134880 | A1 | 5/2012 | Kurkina et al. |
| 2014/0054651 | A1 | 2/2014 | Bashir et al. |
| 2014/0106338 | A1 | 4/2014 | Fischer |
| 2014/0174927 | A1 | 6/2014 | Bashir et al. |
| 2017/0022546 | A1 | 1/2017 | Bashir et al. |
| 2018/0119218 | A1 | 5/2018 | Bashir et al. |

FOREIGN PATENT DOCUMENTS

| | | |
|---|---|---|
| WO | WO 2013/173754 A1 | 11/2013 |
| WO | WO 2017/123730 A1 | 7/2017 |

OTHER PUBLICATIONS

U.S. Appl. No. 15/128,879, filed Sep. 23, 2016, Patented.

Ahn et al., "Double-gate nanowire field effect transistor for a biosensor," Nano Letters, 10(8): 2934-2938 (2010).

Ahn et al., "A pH sensor with a double-gate silicon nanowire field-effect transistor," Applied Physics Letters, 102(8): 083701 (2013).

Andelman, "Flow through capacitor basics," Separation and Purification Technology, 80(2): 262-269 (2011).

Barragán et al., "Effect of an AC perturbation on a desalination electrodialysis process," Desalination, 142(3): 235-244 (2002).

Bergveld, "The development and application of FET-based biosensors," Biosensors, 2(1): 15-33 (1986).

Bergveld, "Thirty years of Isfetology: What happened in the past 30 years and what may happen in the next 30 years," Sensors and Actuators B: Chemical, 88(1): 1-20 (2003).

Borukhov et al., "Steric effects in electrolytes: A modified Poisson-Boltzmann equation," Physical Review Letters, 79(3): 435 (1997).

Bunimovich et al., "Quantitative real-time measurements of DNA hybridization with alkylated nonoxidized silicon nanowires in electrolyte solution," Journal of the American Chemical Society, 128(50): 16323-16331 (2006).

Chapman, "Li. A contribution to the theory of electrocapillarity," The London, Edinburgh, and Dublin Philosophical Magazine and Journal of Science, 25(148): 475-481 (1913).

Chen et al., "Contacting versus insulated gate electrode for Si nanoribbon field-effect Sensors operating in electrolyte," Analytical Chemistry, 83(24): 9546-9551 (2011).

Cheung et al., "Impedance spectroscopy flow cytometry: On-chip label-free cell differentiation," Cytometry Part A, 65(2): 124-132 (2005).

Cui et al., "Nanowire nanosensors for highly sensitive and selective detection of biological and chemical species," Science, 293(5533): 1289-1292 (2001).

Delgado et al., "Measurement and interpretation of electrokinetic phenomena (IUPAC technical report)," Pure and Applied Chemistry, 77(10): 1753-1805 (2005).

Demirer et al., "Laser-induced fluorescence visualization of ion transport in a pseudo-porous capacitive deionization microstructure," Microfluidics and Nanofluidics, 16(1-2): 109-122 (2014).

Dorvel et al., "Vapor-phase deposition of monofunctional alkoxysilanes for sub-nanometer-level biointerfacing on silicon oxide surfaces," Advanced Functional Materials, 20(1): 87-95 (2010).

Dorvel et al., "Silicon nanowires with high-k hafnium oxide dielectrics for sensitive detection of small nucleic acid oligomers," ACS Nano, 6(7): 6150-6164 (2012).

Dorvel et al., "Effect of biointerfacing linker chemistries on the sensitivity of silicon nanowires for protein detection," Analytical Chemistry, 85(20): 9493-9500 (2013).

Elnathan et al., "Biorecognition layer engineering: overcoming screening limitations of nanowire-based FET devices," Nano Letters, 12(10): 5245-5254 (2012).

Go et al., "Coupled heterogeneous nanowire-nanoplate planar transistor sensors for giant (> 10 V/pH) Nernst response," ACS Nano, 6(7): 5972-5979 (2012).

Gao et al., "Enhanced sensing of nucleic acids with silicon nanowire field effect transistor biosensors," Nano Letters, 12(10): 5262-5268 (2012).

Guan et al., "Field-effect reconfigurable nanofluidic ionic diodes," Nature Communications, 2: 506 (2011).

Hindson et al., "High-throughput droplet digital PCR system for absolute quantitation of DNA copy number," Analytical Chemistry, 83(22): 8604-8610 (2011).

Honig et al., "Classical electrostatics in biology and chemistry," Science, 268(5214): 1144-1149 (1995).

Huang et al., "Metal-Assisted Chemical Etching of Silicon: A Review: In memory of Prof. Ulrich Gösele," Advanced materials, 23(2): 285-308 (2011).

Huh et al., "Advanced cleanup process of the free-flow microfluidic device for protein analysis," Ultramicroscopy, 108(10): 1365-1370 (2008).

Ishikawa et al., "Label-free, electrical detection of the SARS virus N-protein with nanowire biosensors utilizing antibody mimics as capture probes," ACS Nano, 3(5): 1219-1224 (2009).

Jayashree et al., "Characterization and application of electrodeposited Pt, Pt/Pd, and Pd catalyst structures for direct formic acid micro fuel cells," Electrochimica Acta, 50(24): 4674-4682 (2005).

Kilic et al., "Steric effects in the dynamics of electrolytes at large applied voltages. I. Double-layer charging," Physical Review E, 75(2): 021502 (2007).

Kim et al., "Direct label-free electrical immunodetection in human serum using a flow-through-apparatus approach with integrated field-effect transistors," Biosensors and Bioelectronics, 25(7): 1767-1773 (2010).

Kulkarni et al., "Detection beyond the Debye screening length in a high-frequency nanoelectronic biosensor," Nano Letters, 12(2): 719-723 (2012).

Lee et al., "Electrode reactions and adsorption/desorption performance related to the applied potential in a capacitive deionization process," Desalination, 258(1-3): 159-163 (2010).

Mani, "Electrodialysis water splitting technology," Journal of Membrane Science, 58(2): 117-138 (1991).

Nair et al., "Performance limits of nanobiosensors," Applied Physics Letters, 88(23): 233120 (2006).

Nair et al., "Design considerations of silicon nanowire biosensors," IEEE Transactions on Electron Devices, 54(12): 3400-3408 (2007).

Patolsky et al., "Electrical detection of single viruses," Proceedings of the National Academy of Sciences, 101(39): 14017-14022 (2004).

Purushothaman et al., "Protons and single nucleotide polymorphism detection: A simple use for the Ion Sensitive Field Effect Transistor," Sensors and Actuators B: Chemical, 114(2): 964-968 (2006).

Rajan et al., "Performance limitations for nanowire/nanoribbon biosensors," Wiley Interdisciplinary Reviews: Nanomedicine and Nanobiotechnology, 5(6): 629-645 (2013).

Reddy, Jr. et al., "High-k dielectric Al2O3 nanowire and nanoplate field effect sensors for improved pH sensing," Biomed Microdevices, 13(2): 335-344 (2011).

Rothberg et al. "An integrated semiconductor device enabling non-optical genome sequencing." Nature, 475(7356): 348 (2011).

(56)     References Cited

OTHER PUBLICATIONS

Salm et al., "Ultralocalized thermal reactions in subnanoliter droplets-in-air," Proceedings of the National Academy of Sciences, 110(9): 3310-3315 (2013).

Sørensen et al., "Screening model for nanowire surface-charge sensors in liquid," Applied Physics Letters, 91(10): 102105 (2007).

Stern, et al., "Importance of the Debye screening length on nanowire field effect transistor sensors," Nano Letters, 7(11): 3405-3409 (2007).

Stern et al., "Label-free biomarker detection from whole blood," Nature Nanotechnology, 5(2): 138 (2010).

U.S. Patent Office, International Search Report in International Patent Application No. PCT/US2015/023101, 2 pp. (Jul. 8, 2015).

U.S. Patent Office, Written Opinion in International Patent Application No. PCT/US2015/023101, 6 pp. (Jul. 8, 2015).

Van Den Berg et al., "A micro-volume open liquid-junction reference electrode for pH-ISFETs," Sensors and Actuators B: Chemical, 1(1-6): 425-432 (1990).

Welgemoed et al., "Capacitive deionization technology™: an alternative desalination solution," Desalination, 183(1-3): 327-340 (2005).

Ye et al., "Self-assembled synthesis of SERS-active silver dendrites and photoluminescence properties of a thin porous silicon layer," Electrochemistry Communications, 10(4): 625-629 (2008).

Zhang et al., "DNA sensing by silicon nanowire: charge layer distance dependence," Nano Letters, 8(4): 1066-1070 (2008).

Zhang et al., "Label-free direct detection of MiRNAs with silicon nanowire biosensors," Biosensors and Bioelectronics, 24(8): 2504-2508 (2009).

Zhang et al., "Porous dendritic platinum nanotubes with extremely high activity and stability for oxygen reduction reaction," Scientific Reports, 3: 1526 (2013).

Zheng et al., "Multiplexed electrical detection of cancer markers with nanowire sensor arrays," Nature Biotechnology, 23(10): 1294 (2005).

Zhu et al., "An on-demand microfluidic hydrogen generator with self-regulated gas generation and self-circulated reactant exchange with a rechargeable reservoir," Microfluidics and nanofluidics, 11(5): 569 (2011).

* cited by examiner (a)
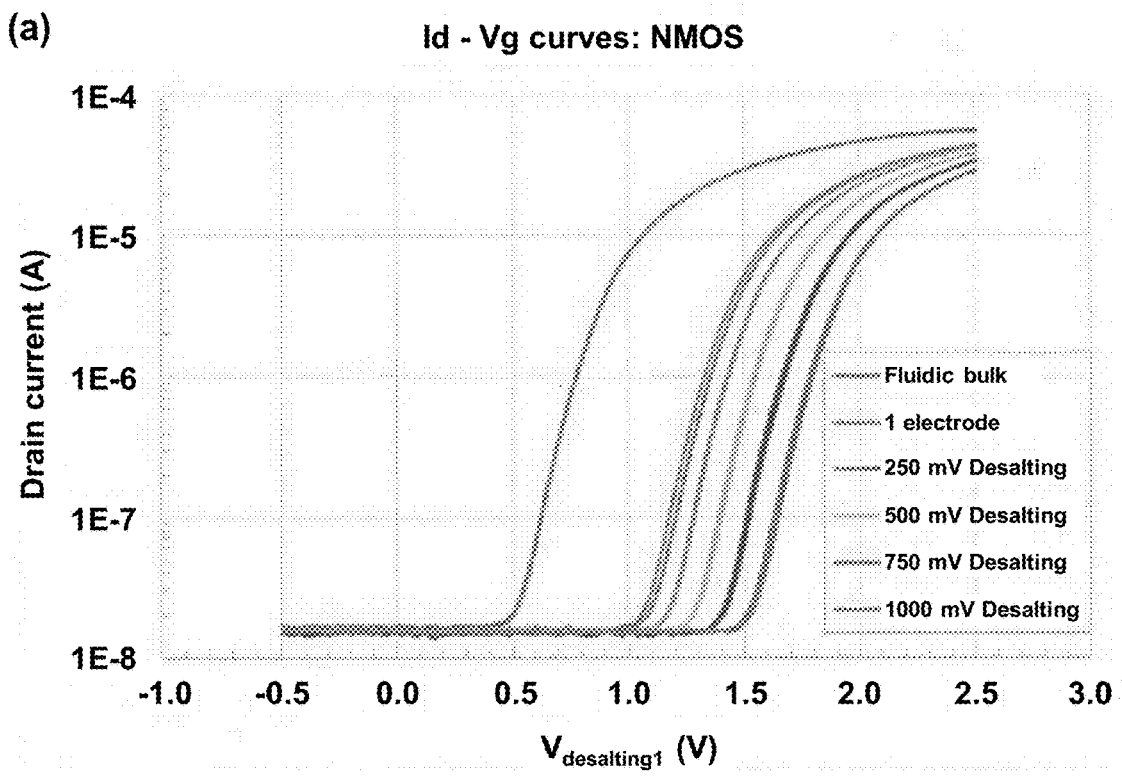
(b)
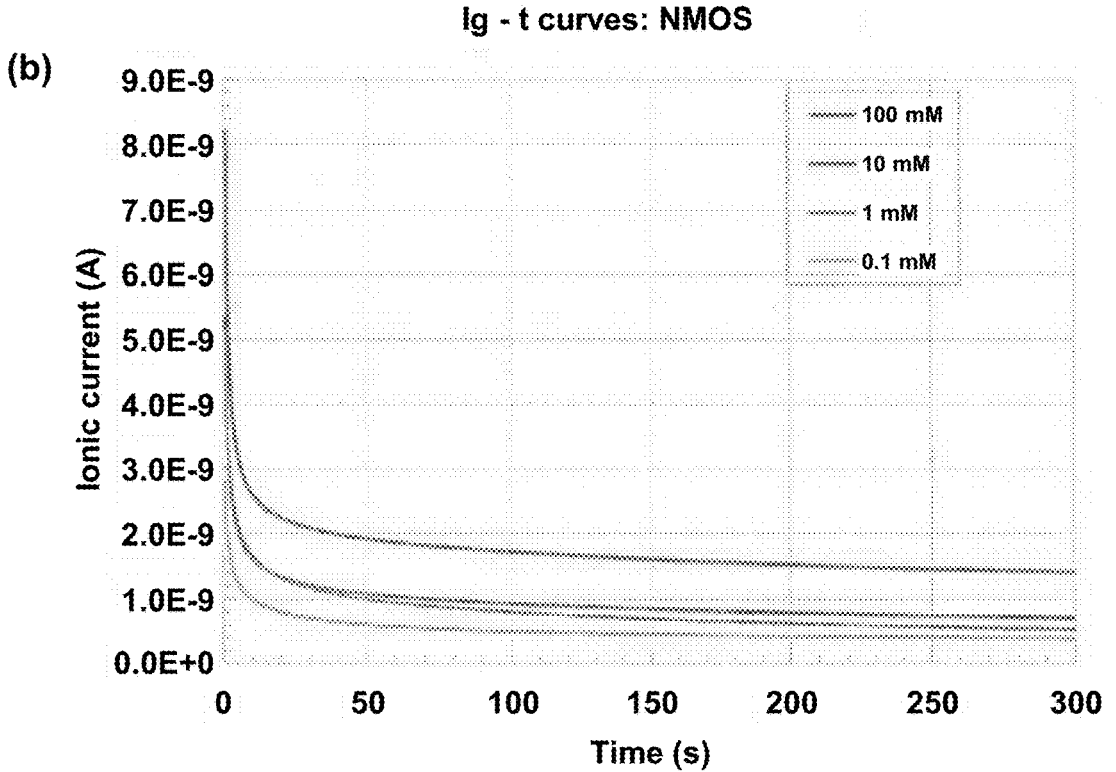
FIG. 2

(c)
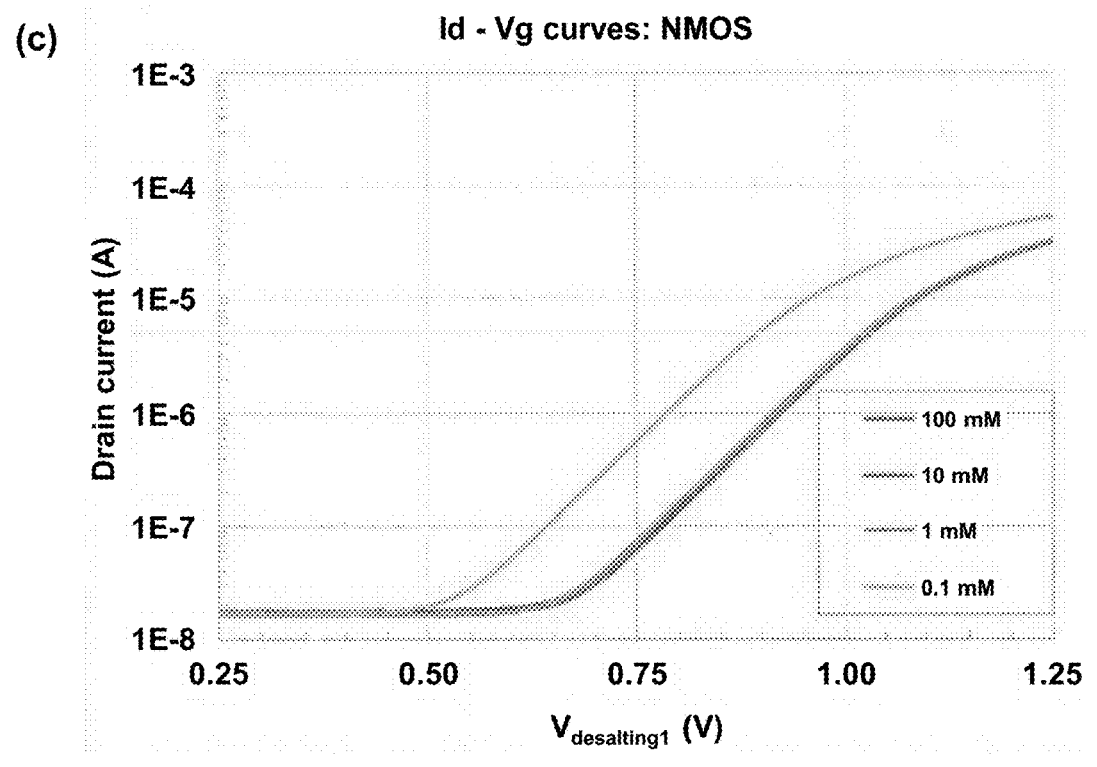
(d)
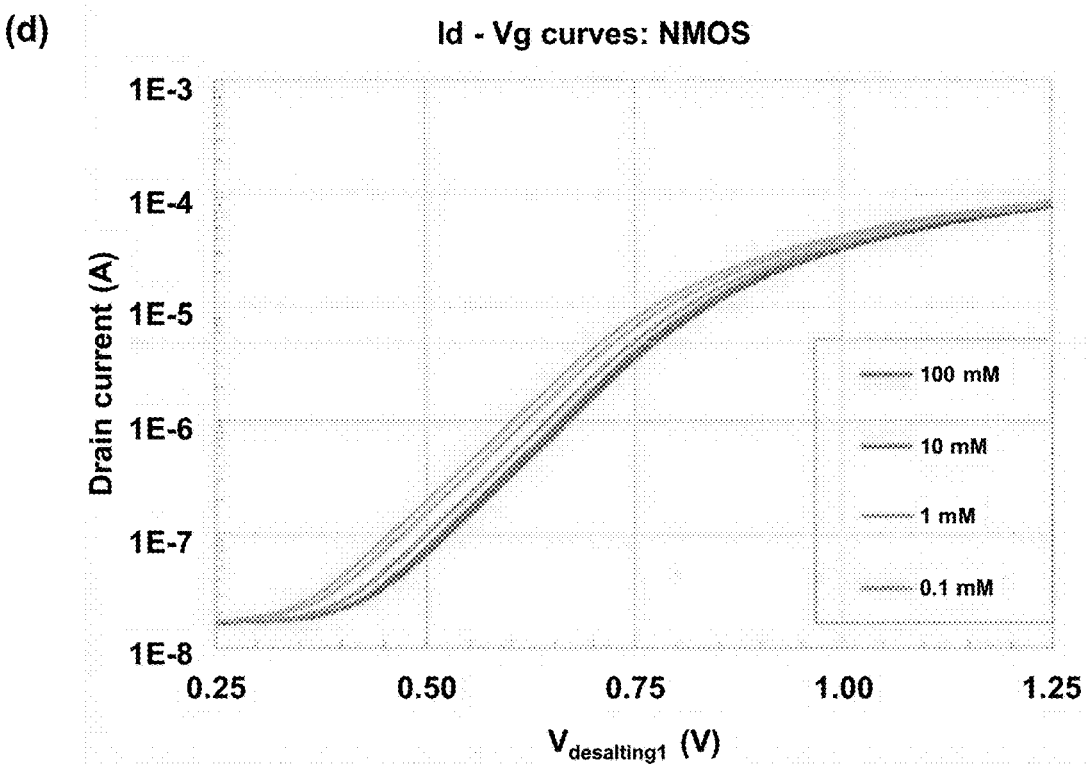
FIG. 2 (Cont'd)

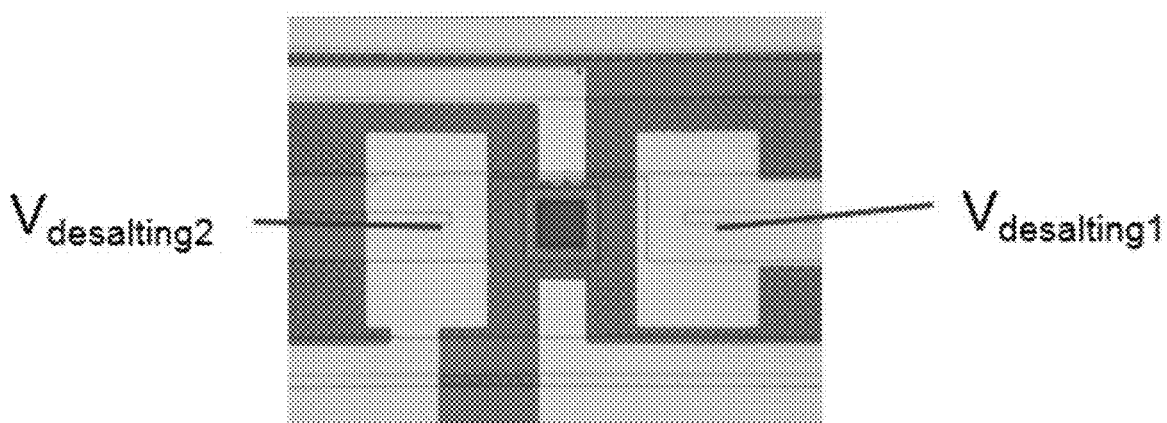
*Two electrode configuration*
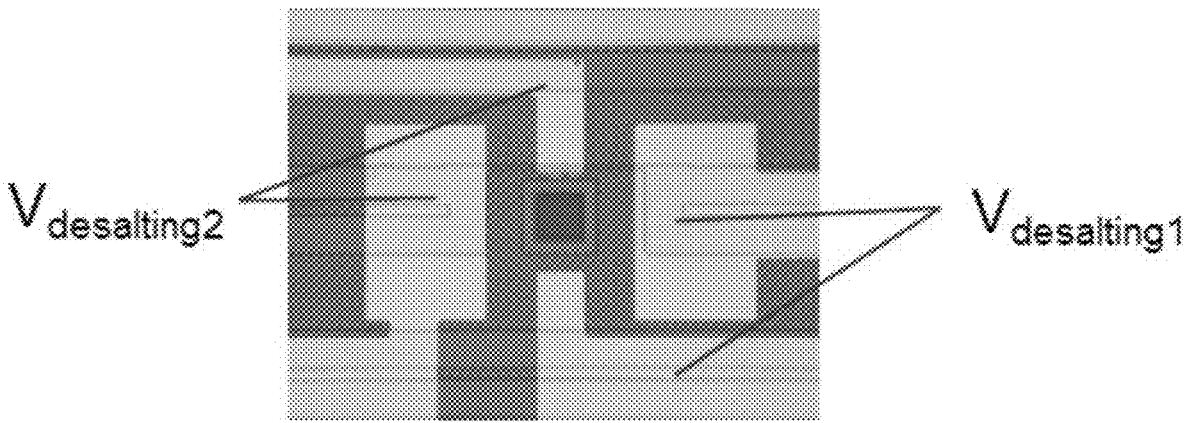
*Four electrode configuration*
FIG. 6

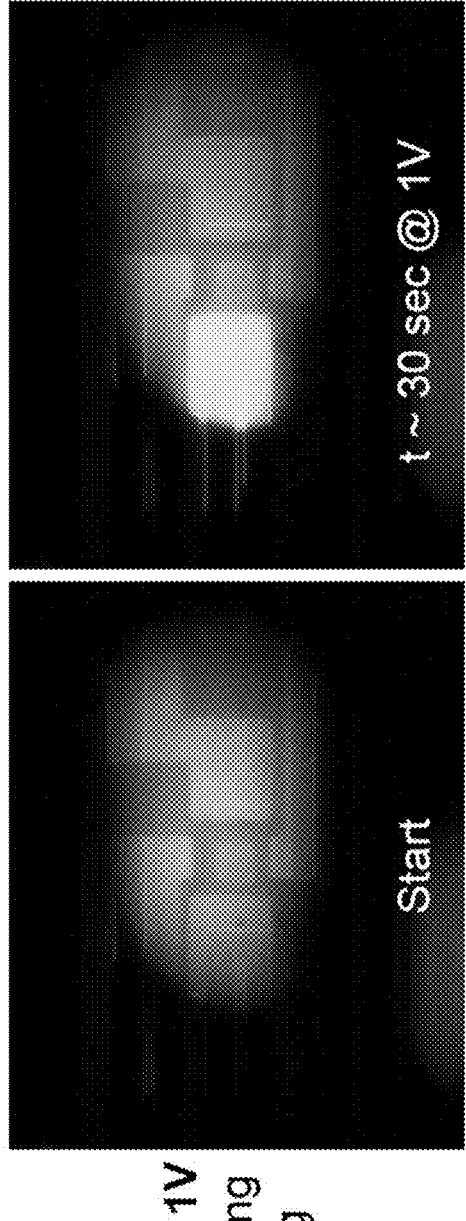
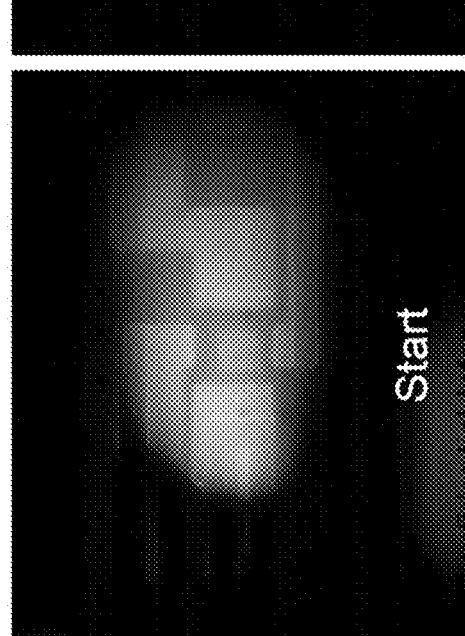
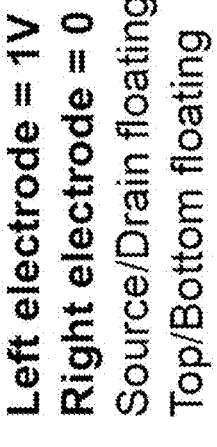
Left electrode = 0
Right electrode = 1V
Source/Drain floating
Top/Bottom floating
**Reverse
control**
Left electrode = 1V
Right electrode = 0
Source/Drain floating
Top/Bottom floating
10 mM ionic strength
FIG. 7

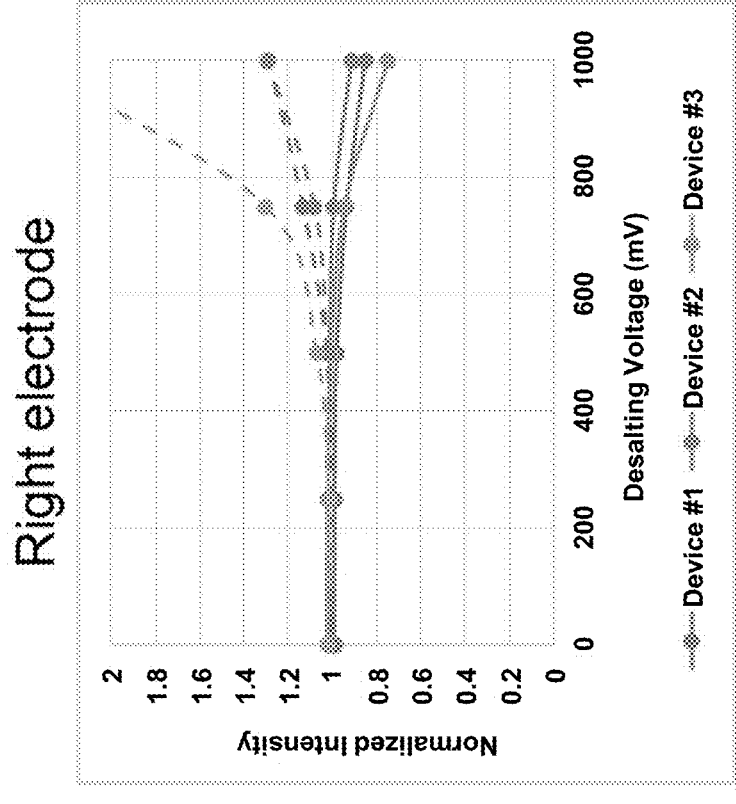
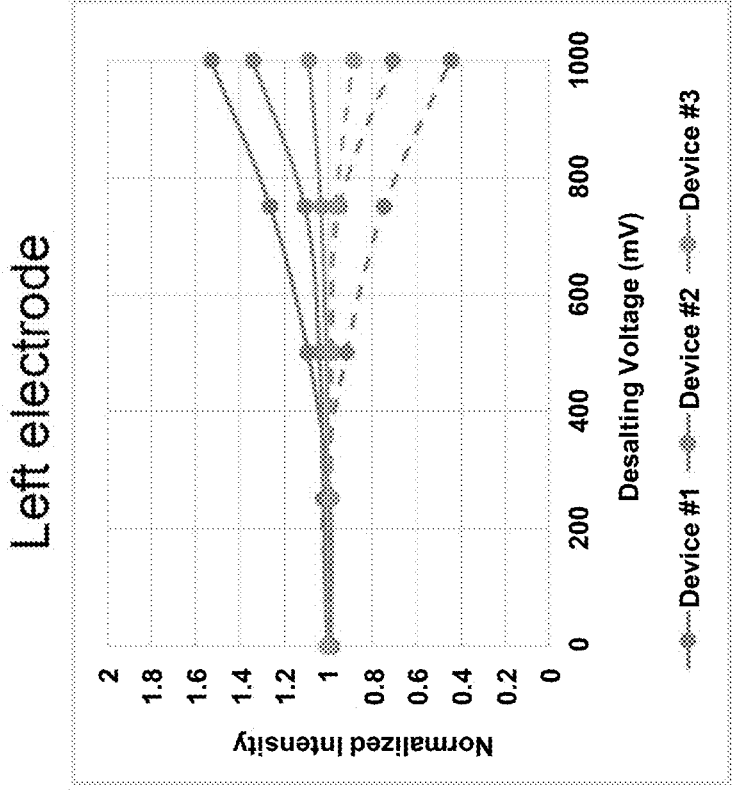
FIG. 8

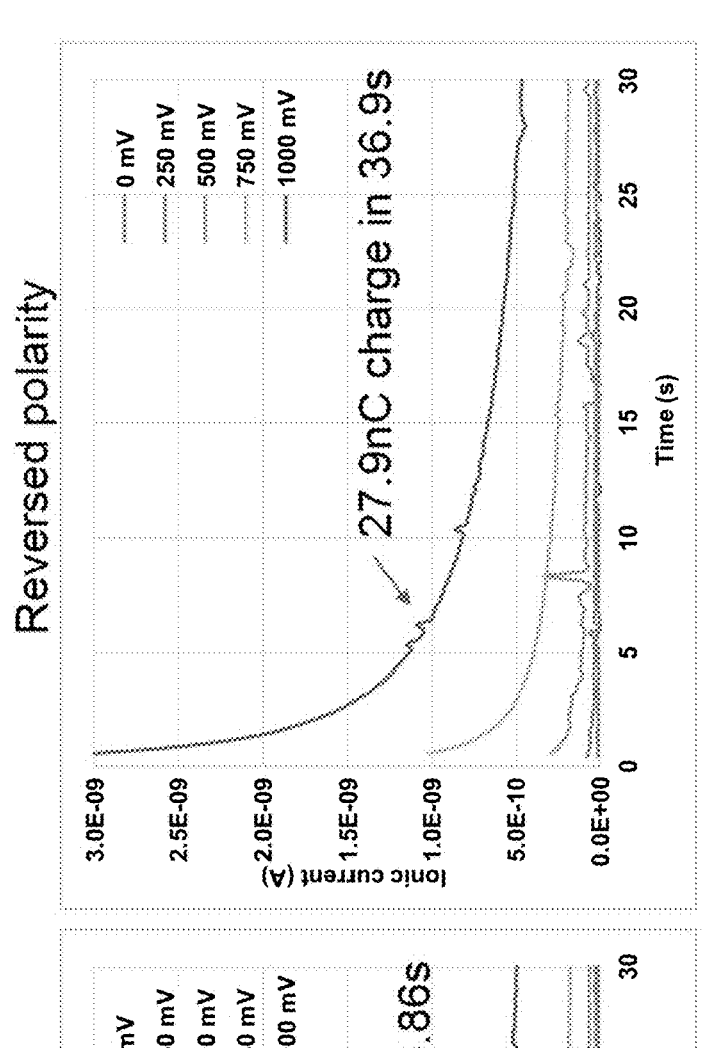
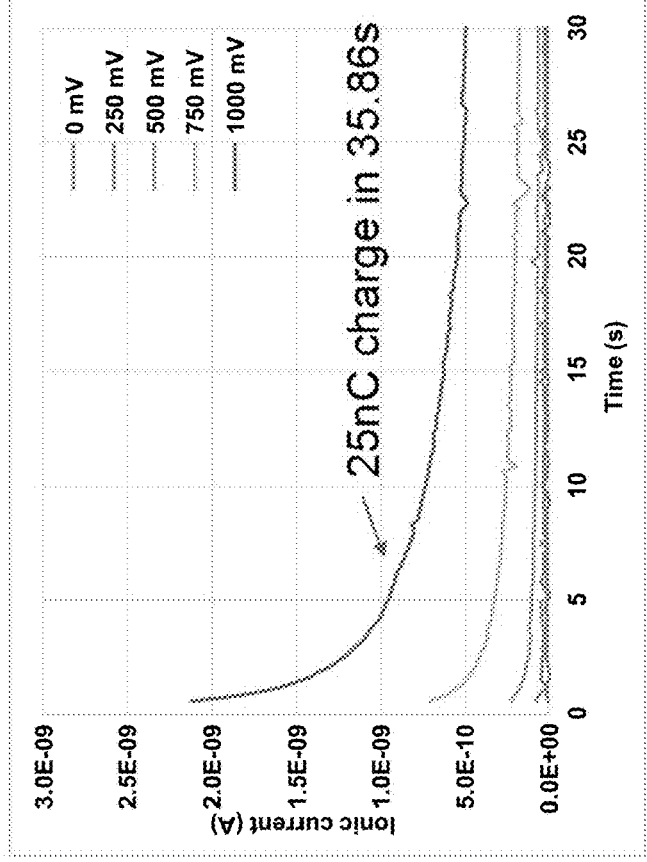
FIG. 9

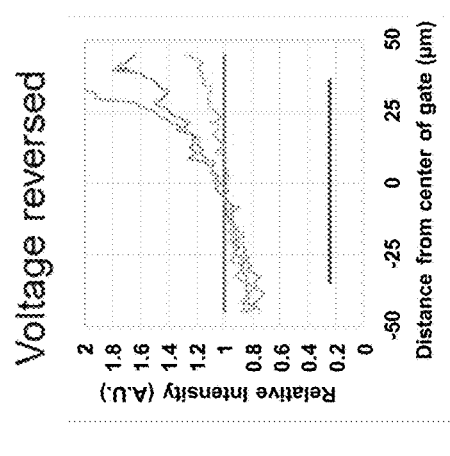
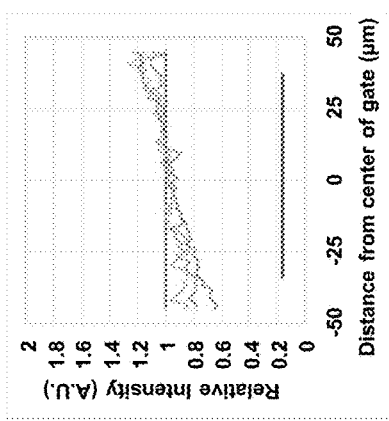
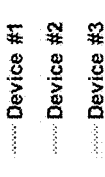
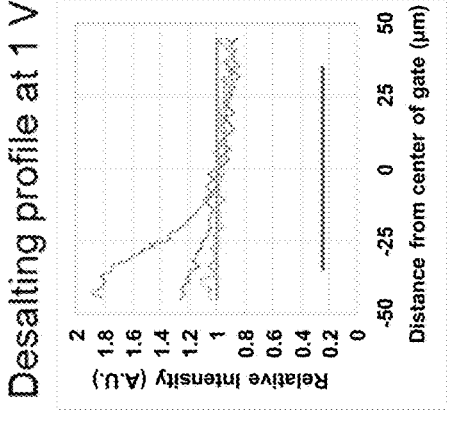
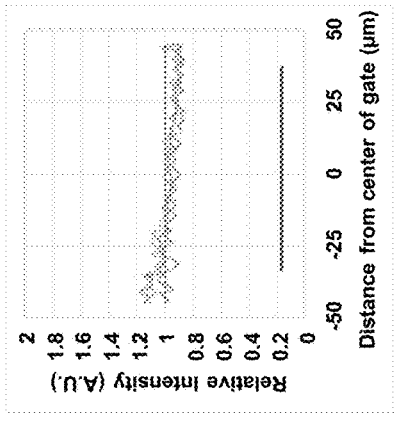
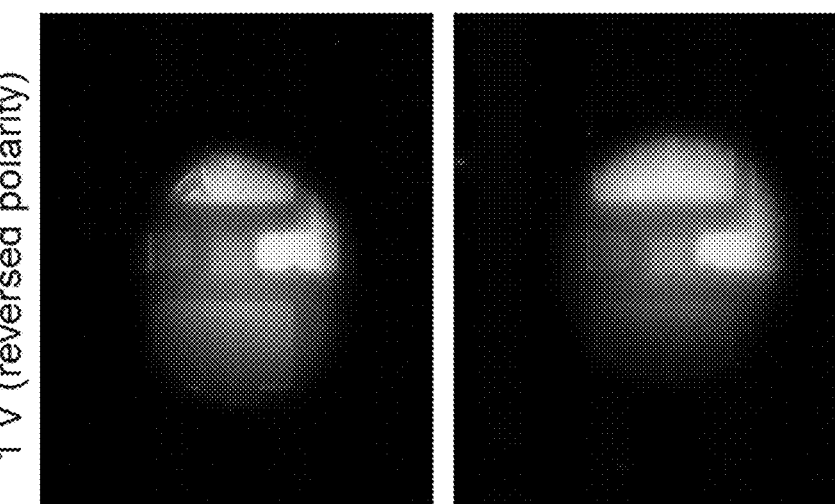
FIG. 13

*Total charge in a 1 nL droplet (positive + negative)*

| Ionic Strength | Total Charge (nC) |
|---|---|
| 0.1mM | 19.27 |
| 1mM | 192.74 |
| 10mM | 1927.4 |
| 100mM | 19273.6 |

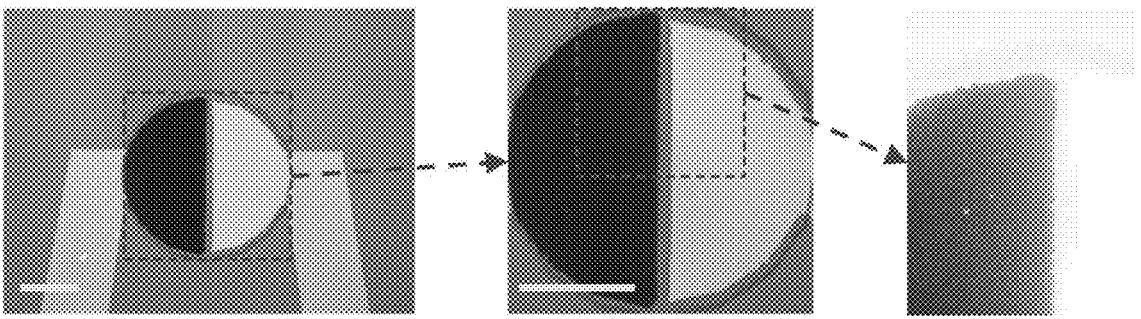
FIG. 22A
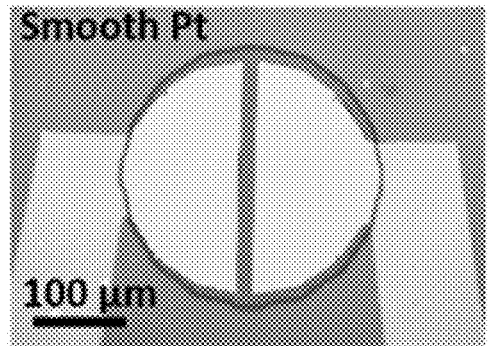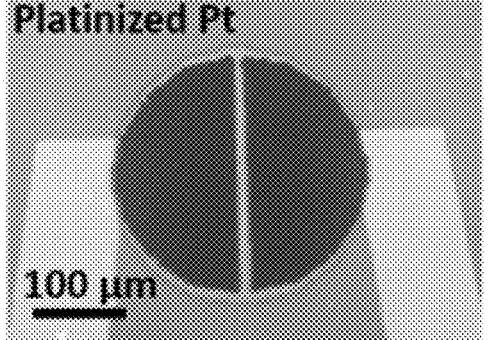
FIG. 22B
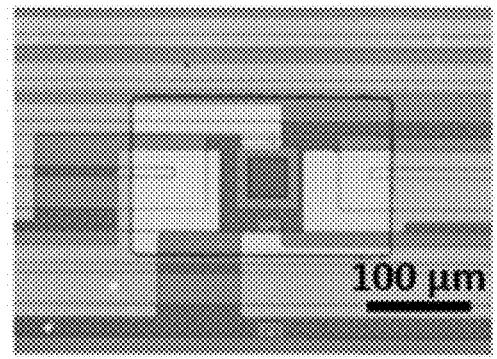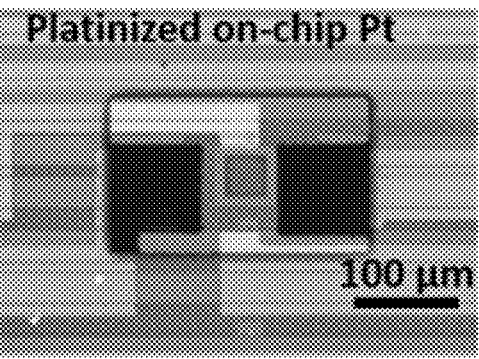
FIG. 22C AFM cannot give us true surface area due to 3D branching in structure, not only peaks/valleys

| Electrode designation | 5 μm x 5 μm section | | 0.25 μm² area | |
|---|---|---|---|---|
| | Smooth | Rough | Smooth | Rough |
| Projected area (μm²) | 3.08 | 3.08 | 0.249 | 0.254 |
| Measured surface area (μm²) | 3.16 | 8.31 | 0.256 | 0.781 |
| Surface area difference | 2.65% | 169% | 2.71% | 208% |
| Mean peak/valley height (nm) | 177 | 265 | 1.78 | 159 |
| RMS height deviation (nm) | 2.26 | 320 | 2.25 | 184 |
| Max peak-to-valley depth (nm) | 19.5 | 1512 | 13.3 | 850 |

Assumes Helmholtz-like linear capacitance behavior

| | Rough #1 | Rough #2 | Rough #3 | Smooth | |
|---|---|---|---|---|---|
| $R_s$ | 288.68 Ω | 256.29 Ω | 253.54 Ω | 239.02 Ω | |
| $f @ \phi_{min}$ | 8.02 kHz | 12.61 kHz | 12.61 kHz | 63.14 kHz | |
| $RC @ \phi_{min}$ | 72 μs | 31.7 μs | 31.8 μs | 1.68 μs | |
| $C/C_{smooth}$ | 42.87 | 18.88 | 18.92 | 1 | |
| $Z_{max}$ | 309.69 Ω | 291.35 Ω | 306.49 Ω | 348.47 Ω | Equivalent Area |
| $f @ Z_{max}$ | 251.20 kHz | 251.20 kHz | 316.27 kHz | 199.55 kHz | Enhanced |
| $|Z/Z_{smooth}|$ | 35.03 | 16.79 | 18.62 | 1 | |

At 1 Hz →

Extended Gate FET

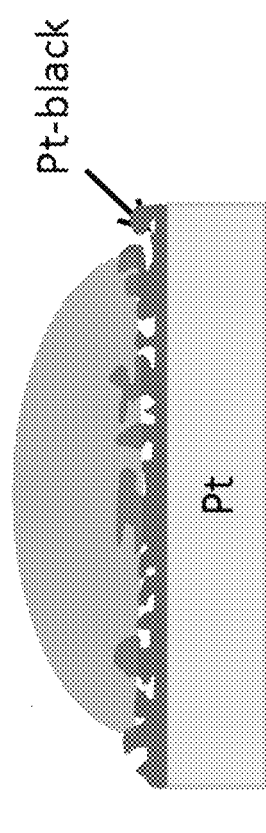
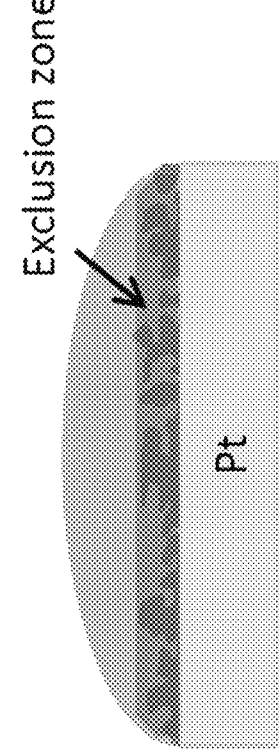
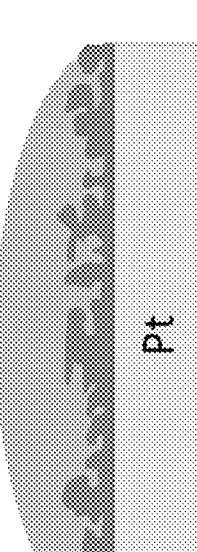
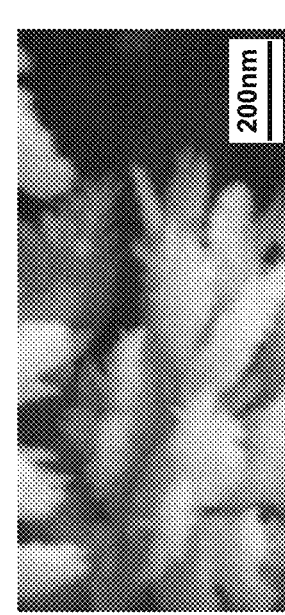
FIG. 37

Simulation Geometry

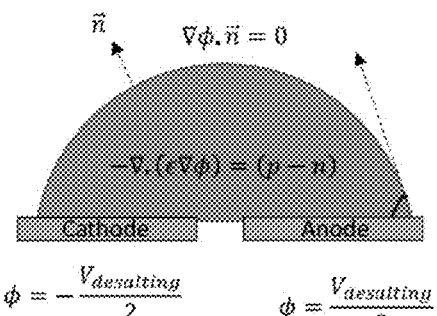

$$\phi = -\frac{V_{desalting}}{2} \qquad \phi = \frac{V_{desalting}}{2}$$

Poisson Equation (with cap on maximum ionic density):

$$-\nabla.\left(\varepsilon\nabla\phi\right) = (p - n)$$

For $p \leq 1/a^3$ or $n \leq 1/a^3$ $$p = n_i \exp\left(\frac{e\phi}{k_B T}\right)$$

$$n = n_i \exp\left(\frac{e\phi}{k_B T}\right)$$

For $p > 1/a^3$ $$p = \frac{1}{a^3}, \qquad n = 0$$

For $n > 1/a^3$ $$n = \frac{1}{a^3}, \qquad p = 0$$

Ion conservation:

$$\int_\Omega p \, dV = \int_\Omega n \, dV = n_0 \, V$$

Boundary Condition:

On Electrodes: $\phi = \pm V_{desalting}/2$ (Dirichlet Boundary Condition)

On Outer Boundaries: $\vec{n} = 0$ (Neumann Boundary Condition)

FIG. 41

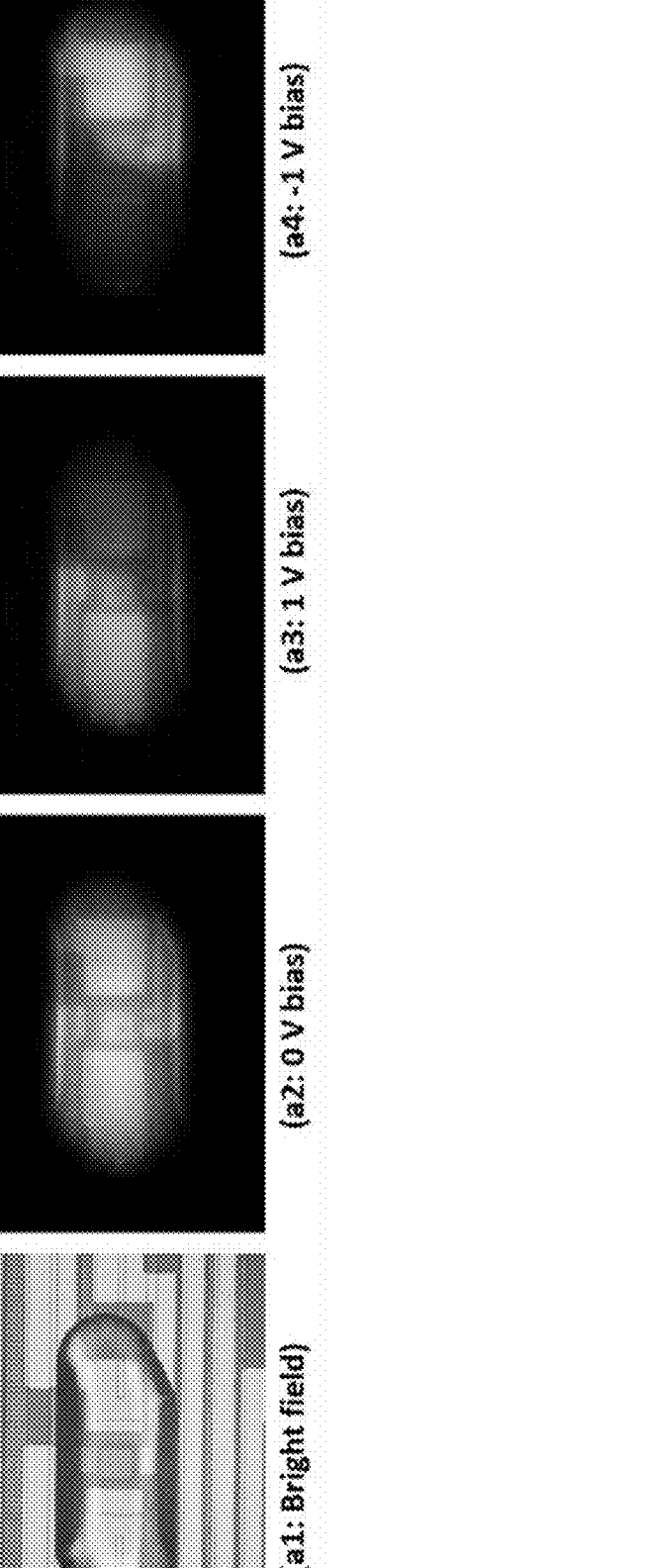
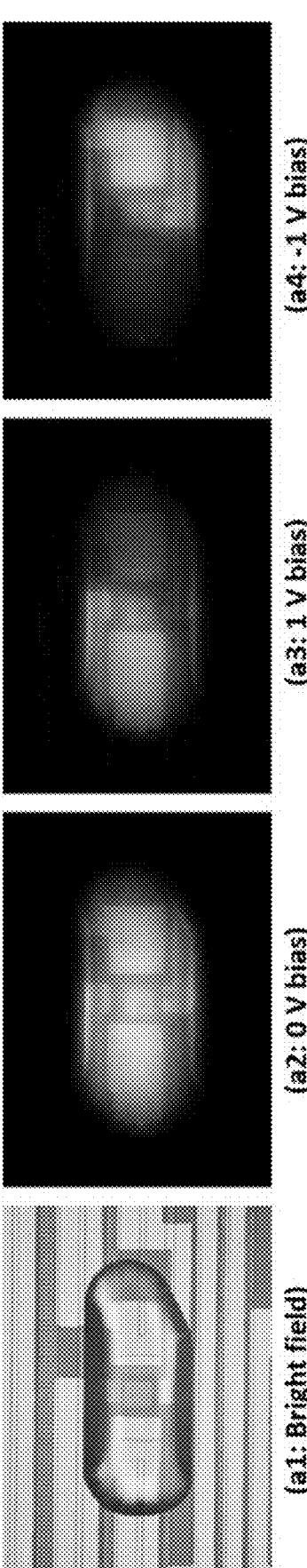
(a4: -1 V bias)     (a3: 1 V bias)     (a2: 0 V bias)     (a1: Bright field)
FIG. 48

LABEL FREE ANALYTE DETECTION BY ELECTRONIC DESALTING AND FIELD EFFECT TRANSISTORS

CROSS-REFERENCE TO RELATED APPLICATIONS

This application is a divisional of U.S. patent application Ser. No. 15/128,879 filed on Sep. 23, 2016, which is a 371 national stage of International Application No. PCT/US2015/023101 filed on Mar. 27, 2015, which claims the benefit of priority to U.S. Provisional Patent Application No. 62/007,808 filed on Jun. 4, 2014, and 61/972,148 filed Mar. 28, 2014, each of which is specifically incorporated by reference to the extent not inconsistent herewith.

STATEMENT REGARDING FEDERALLY SPONSORED RESEARCH OR DEVELOPMENT

This invention was made with government support under RO1CA120003 awarded by the National Institutes of Health, and EEC-0425626 awarded by the National Science Foundation. The government has certain rights in the invention.

BACKGROUND OF INVENTION

The invention is in the field of label free sensing, including label free electronic biomolecular detection using field effect transistors, including ion-sensitive-field-effect-transistors. The invention generally relates to methods for analyte detection and associated devices, particularly analytes comprising biological material suspended in biological material compatible fluids having high relatively high ionic strength.

There is a need in the art for low-cost reliable biological sensors for detecting various analytes. Although a variety of biosensors are available, many conventional sensors require use of a label to assist with analyte detection, including optical labels such as fluorescent dyes and the like, or require more involved amplification steps to amplify a target of interest, such as by polymerase chain reaction. Such conventional sensing systems suffer a common disadvantage of requiring sample preparation, such as one or more of washing, isolation, incubation, temperature control and other handling dependent on the biosensor type.

Field effect transistors (FET) are useful candidates for biosensors to address the above limitations. FETs can be of extreme sensitivity and rely on change in electrical signals attributed to the presence of analytes of interest, thereby avoiding a need for labels or amplification. Examples of various applications using FETs include U.S. Pub. Nos. 2014/0054651, 2011/0086352 and 2012/0021918; PCT Pub. Nos. WO2013/016486, WO2013/173754, WO2012/078340.

There are, however, certain limitations associated with FET sensing, particularly as applied to biological applications. For example, salt concentration is known to strongly influence the sensitivity of FET-based biosensors. The effect of shielding effect of excess ions, which is often represented by the "Debye length", on detecting biomolecules is examined by Stern et al. (Importance of the Debye Screening Length on Nanowire Field Effect Transistor Sensors, Nano Lett., vol. 7, no. 11, pp. 3405-3409, November 2007.) Nair and Alam ("Design Considerations of Silicon Nanowire Biosensors," IEEE Trans. Electron Devices, vol. 54, no. 12, pp. 3400-3408, 2007) analyzed the effect of high salt concentration on the electrical characteristics of nanowire-based FET sensors and show strong links between sensitivity and ionic strength and demonstrate that the response of these sensors rapidly tails off as physiological conditions of 0.15M salt is approached. Further, in a recent review, Rajan et al. (Performance limitations for nanowire/nanoribbon biosensors: Performance limitations for nanowire/nanoribbon biosensors," Wiley Interdiscip. Rev. Nanomed. Nanobiotechnol., vol. 5, no. 6, pp. 629-645, November 2013.) also discussed both the need to overcome ionic shielding and strategies to achieve the same—either through antibody fragmentation, or biomolecule pre-concentration followed by solution exchange to low ionic sensing buffers.

The use of an electrical method, by applying DC fields between a pair of electrodes, to deplete ions from aqueous solution is used in the field of seawater desalination. Capacitive Deionization (CDI) involves the electrophoretic movement of counterions towards charged electrodes, which are then absorbed within the "Debye capacitance layer" to deplete the bulk salt concentration (T. J. Welgemoed and C. F. Schutte, "Capacitive Deionization Technology™: An alternative desalination solution," Desalination, vol. 183, no. 1-3, pp. 327-340, November 2005; J.-H. Lee, W.-S. Bae, and J.-H. Choi, "Electrode reactions and adsorption/desorption performance related to the applied potential in a capacitive deionization process," Desalination, vol. 258, no. 1-3, pp. 159-163, August 2010; O. N. Demirer and C. H. Hidrovo, "Laser-induced fluorescence visualization of ion transport in a pseudo-porous capacitive deionization microstructure," Microfluid. Nanofluidics, July 2013.) See also U.S. Pat. No. 8,377,280 and Pat. Pub. No. 2010/0140096. A similar electrical method (membrane electrodialysis) for desalting with the use of ultraporous membranes is described in U.S. Pat. No. 6,284,117, for primarily PCR-SDA assay techniques.

A common strategy to address sensitivity of FETs is to perform sensing in low ionic buffers. This involves functionalization as well as sensing at low concentrations, far from physiological conditions, or physical desalting after binding in high salt to low sensing buffer concentrations by fluid swap through multiple washing steps (see Stern et al.; and Kim et al. "Direct label-free electrical immunodetection in human serum using a flow-through-apparatus approach with integrated field-effect transistors," Biosens. Bioelectron., vol. 25, no. 7, pp. 1767-1773, March 2010.). Other strategies include biomolecule fragmentation and pre-concentration methods.

Alternatively, complex AC excitation strategies have been incorporated to break the electrochemical double layer formation and sustain electric fields beyond the Debye length for sensing larger biomolecules ("Detection beyond the Debye Screening Length in a High-Frequency Nanoelectronic Biosensor," Nano Lett., vol. 12, no. 2, pp. 719-723, February 2012.). Again this method relies on electrophoretic movement of ions and the use of high-frequency excitations to perturb electric fields in solution at faster speeds than the mobility of ions.

Implementation of on-chip desalting around sensors generally include microfluidic in-line membrane-based desalting of analyte for FET based detection (U.S. Pat. Pub. No. 2009/0142825). Also described are electrophoretic schemes (DC electric fields using electrodes around mixing channels) for microfluidic desalting for protein enrichment in mass spectroscopy sensors ("Advanced cleanup process of the free-flow microfluidic device for protein analysis," Ultramicroscopy, vol. 108, no. 10, pp. 1365-1370, September 2008).

SUMMARY OF THE INVENTION

Provided herein are methods and related devices for label free sensing using FETs having improved sensor response and detection characteristics. In particular, the special geometry of the systems provided herein, including locally patterned on-chip metal electrodes in close proximity to the FET, allow for simultaneous electrical desalting and FET gating and corresponding analyte sensing. Other aspects that facilitate label free analyte sensing in high ionic strength solutions include reduced sample volume, such as in a droplet and also increased in effective surface area of the reference electrodes.

Conventional FET systems comprise a transistor whose gate is exposed to an ionic medium, with a gate voltage that determines conduction that is applied by a fluidic standard reference electrode. Sensing is then accomplished by an analyte reaction that affects change in the concentration of an ion or pH, which in turn perturbs the gate voltage. Detection of a change in the gate voltage provides an indication of analyte. In the methods and systems provided herein, the fluidic reference electrode is replaced by on-chip reference electrodes in close proximity to the FET. The reference electrodes may be precisely positioned and have precise geometrical layout, such as by patterning methods known in the art, including lithography and other microfabrication methods. In an aspect, the reference electrodes are arranged in a paired geometry, with the electrodes opposibly configured to one another and the sensor of the FET disposed therebetween in close proximity. In any of the methods and devices provided herein, the reference electrodes in this geometry are energized so as to attract charged carriers, such as ions, dissolved salts and electrolytes from the FET sensor to the surface of the reference electrodes, thereby reducing the screening effects associated with the charged ions. Both negatively and positively charged ions are attracted to a reference electrode by energizing one of the reference electrodes with a positive electric potential and the counter-electrode with a negative electric potential.

In an aspect, the potentials are selected so as to also provide an appropriate gate voltage to the FET. In this manner, the conventional fluidic standard reference electrode is replaced with the reference electrodes provided herein and the gate voltage may be described as coupled to the reference electrodes that are also electrically desalting the sample solution. Any of the methods provided herein relate to use of small sample volumes so that the electrodes can attract charged ions from throughout the sample, thereby avoiding a tendency of charged ions to simply backfill the depleted ion region from the rest of the sample solution via diffusion. In this manner, the fluid droplet is preferentially flattened and covers a significant portion or all the reference electrode contact surface area. Accordingly, any of the methods provided herein relate to electrode contact surface area having an increased working contact surface area, such as by processing the surface to increase surface area via roughening, or through the use of porous electrodes that increase surface area available to interact with charged ions.

In an embodiment, the invention is a method for detecting an analyte in a sample solution by providing a field effect transistor (FET) and a paired set of reference electrodes in close proximity to the FET with the FET positioned between the paired set of reference electrodes. Sample solution comprising charged ions is introduced to the FET and reference electrodes. At least one of the paired set of reference electrodes is electrically biased relative to the FET or to another reference electrode to electronically remove at least a portion of charged ions from a sensor area adjacent to a sensor of the FET, and thereby deplete charged ions in the sensor area, wherein the electrical biasing generates a stable FET gate voltage. A FET electrical parameter is monitored during the electrically biasing step, wherein a change in the electrical parameter corresponds to presence of analyte in the sample solution and a no change in the electrical parameter corresponds to absence of analyte in the sample, thereby detecting the presence or absence of analyte in the sample solution.

In an aspect, the removed charged ions comprise ions that adsorb to a surface of at least one of the reference electrodes. For example, negatively charged ions are attracted toward the surface of a positively charged electrode and positively charged ions are attracted toward the surface of a negatively charged electrode. To recharge the electrodes, the polarity may be temporarily reversed to release ions from the electrode surface and ready the system for another sample.

In an aspect, the depleted charged ions in the sensor area corresponds to a sensor area that extends from the sensor, such as a sensor surface, into the sample solution by a Debye screening length and defines a depletion region. Depletion of charged ions reduces the effective ionic strength in the region, thereby increasing the Debye screening length. In an aspect, the depletion region provides a Debye screening length that is increased by a factor of at least three, at least a factor of five, or at least a factor of ten, compared to a Debye screening length for an equivalent system without said electrically biasing step. In this manner, the electrostatic shielding effect associated with excess charged ions in solution is avoided or minimized, specifically for the analyte of interest. For example, any of the methods provided herein may be described in terms of increasing the Debye screening length to a value that is greater than or equal to a length of the analyte, or that is a substantial fraction thereof, such as at least 50%, at least 70%, or at least 90%. In an aspect, the electrically biasing step may be described in terms of absolute values, such as increasing the Debye screening length from less than about 1 nm (e.g., corresponding to a solution having an ionic strength similar to physiological solutions, such as about greater than 100 millimolar, such as about 150 millimolar or between about 100 millimolar to about 350 millimolar) to greater than about 3 nm, greater than 5 nm, greater than 10 nm, or between about 3 nm and 15 nm.

In an aspect, the depletion of charged ions described herein may be described in terms of a functional benefit of an analyte detection limit, such as an analyte detection limit selected from a range that is between about 1 nanomolar and 1 attomolar. This is a reflection that reducing electrostatic interference by excess free charged ions in the sample provides much higher detection limits than conventional FET biosensors that do not adequately address the interference by the excess charged ions.

One important aspect of any of the methods, systems and devices provided herein, is the electronic removal of charged ions that is substantially simultaneous or that is simultaneous with the monitoring step. This is a fundamental improvement of conventional FET systems that otherwise rely on an independent control of the FET gate voltage. The instant methods, systems, and devices, in contrast, have a FET gate voltage that is coupled to the reference electrode and the appropriate selection of reference electrode voltage both removes charged ions from the sample solution and provides a stable FET gate voltage.

In an aspect, the sample solution comprises a biological fluid obtained from a test subject. The biological fluid may be saliva, blood, plasma, urine, semen, perspiration or any fluid constituent thereof. In an aspect, the biological fluid is minimally processed before being introduced to the FET and reference electrodes. In an aspect the introduced sample solution has a high ionic strength, wherein the high ionic strength is greater than 100 mM, greater than 200 mM, or that is physiological, such as between about 100 mM and 350 mM or so that there is not adverse swelling or shrinkage due to an adverse osmotic pressure gradient between the suspending fluid and a solution contained within a semipermeable membrane, such as a membrane of a biological organism. In an aspect, the ionic strength corresponds to that of blood, which is generally about 150 mM.

In an aspect, the sample solution comprises a physiological level of salts and the charged ions comprise the salts dissolved in the sample solution. Such dissolved salts have positive and negative ions and can be a significant source of interference by electrically associating with an analyte that interacts with the FET sensor, thereby effectively screening or masking detected signal from the FET.

In an embodiment, any of the methods and devices described herein relate to an introduced sample that comprises a fluid droplet, such as a fluid droplet having a volume that is less than about 50 nL. Limited droplet sizes are one means for minimizing total amount of free charge in the introduced sample, so that depletion of charged ions are simply not backfilled with other charged ions that diffuse to the depletion region.

In an aspect, the method further comprises the step of wetting a contact surface of the reference electrodes to facilitate droplet anchoring to the contact surfaces of the reference electrodes. Similarly, the contact surface of the reference electrode may be suitably processed to provide hydrophilic and hydrophobic regions, to thereby confine a droplet to a desired position, such as over the FET sensor and the reference electrodes to maximize desalting and sensing. To maximize desalting or removal of charged ions, the droplet preferably spreads, is flattened and occupies a maximum amount to a contact surface of the electrodes.

In an embodiment, any of the methods and devices provided herein relate to an analyte that is a biological material suspended in a physiological fluid. The biological material may be one or more of a cell; a virus; a polynucleotide, a polypeptide, a protein, DNA, RNA, an antibody, a cell surface receptor; and a charged macromolecule. The methods and devices herein are compatible with any charged macromolecule, particularly to those macromolecules that are sufficiently large as to extend past a Debye screening length so that charged ions that interact with the marcromolecules interfere with the ability of detect changes in an electrical parameter with the FET.

The methods and devices provided herein is compatible with a wide range of FETs. In an aspect, the FET comprises: a source electrode, a drain electrode, wherein the sensor electrically connects the source and the drain electrodes, and a sensing surface over at least a portion of the sensor. To improve analyte interaction with the sensing surface, the sensing surface may be functionalized to facilitate a binding interaction with the analyte, wherein the binding interaction occurs prior to or simultaneously with the electrically biasing step. In an aspect, the sensor comprises a nanowire, so that the sensing surface corresponds to a surface of the nanowire.

Any of the devices or methods provided herein comprise the electrical biasing step that generates a stable FET gate voltage that is substantially simultaneous or simultaneous with the control of an ionic environment in the sensor area and detection of the analyte. In this manner, the FET gate is considered to be electrically coupled to the reference electrodes, with the reference electrodes providing two functions of: (1) desalting; and (2) FET gating.

In an aspect, the methods and devices provided herein comprise the FET and reference electrodes on a chip or other common substrate. A chip is useful as a variety of processing steps known in the art may be utilized to obtain the desired electrode and FET geometries, relative positioning, and further processing steps, such as electrode surface roughening and well-formation for confining nanoliter, sub-nanoliter, or picoleter size sample volumes.

The methods and systems provided herein may comprise an array of FETs and reference electrodes for multiplexed detection.

In an aspect, the reference electrodes comprise a patterned metal electrode. In an aspect, the patterned metal electrode is provided by a lithographic, microfabrication or nanofabrication method.

In an embodiment, the reference electrodes comprise symmetrically opposed metal electrodes with the FET disposed therebetween. One example of symmetrically opposed metal electrodes are substantially semi-circular opposed electrodes separated by the FET. Substantially semicircular includes semi-circular electrodes, and refer to the combination of the electrode pair having a substantially circular footprint to maximize contact area as a fluid droplet spreads and flattens. In this aspect, substantially circular refers to a maximum deviation from an average diameter that is less than 20%. In an aspect, the substantially semi-circular opposed electrodes separated by the FET are enclosed within a well, and the sample solution comprises a droplet that covers at least 90% of a contact surface within the well. In an aspect, the position of the well surface generally corresponds to a semicircular outer limit of the reference electrodes, so that the spread droplet occupies most, substantially all, or all the semicircular-portion of the reference electrodes. This aspect maximizes the working surface area available for charged ion interaction and can help ensure charged ions are substantially depleted from the sensor area.

In an aspect, the method or device comprises a plurality of electrode pairs, wherein each reference electrode within a pair symmetrically oppose each other. In an aspect, the plurality of electrode pairs comprises, two pairs, three pairs, four pairs or five pairs.

Any of the methods and devices herein are for a sample solution that is a fluid droplet having a volume (Vdroplet), and the paired set of reference electrodes has an electrode contact surface area in contact with the droplet (AED), with a ratio of droplet volume to electrode contact surface area (Vdroplet/AED) is less than or equal to 1 µm. Such a ratio facilitates substantial removal of charged ions from not only the sensor area, but also effectively from the entire droplet to avoid backfilling of charged ions to the sensor area via ion diffusion.

Any of the methods and devices provided herein comprise reference electrodes that are processed to increase an effective surface area available for contact, wherein the processing increases the effective surface area available for contact by a factor of at least 10 or 50 compared to an electrode surface area footprint. "Footprint" refers to the surface area defined by an outer edge of the electrode, such as corresponding to the outer limit of the fluid droplet. "Effective surface area" takes into account the surface morphology and, for recess and relief features on the electrode surface, can significantly increase surface area compared to an equivalent smooth surface electrode. In particular, the processing may result in surface roughening that increases the surface area. The surface processing may be selected from the group consisting of physical deposition, electrodeposition, etching, and chemical vapor deposition.

In an aspect, the reference electrodes comprise on-chip platinum electrodes.

In an aspect, the close proximity between the reference electrodes and the FET corresponds to a separation distance between the reference electrodes and the FET that is less than or equal to 30 μm, and the FET and reference electrodes are supported by a common substrate. Such a distance may provide sufficient space for electrode processing, such as for surface roughening or coatings.

The electrical biasing step may provide ion and counterion adsorption on the reference electrodes. The electrical biasing may comprise providing a first negative desalting voltage (Vdesalting1) to a first electrode of the reference electrode pair; and providing a second positive desalting voltage (Vdesalting2) to a second electrode of the reference electrode pair. Such negative and positive desalting voltages ensures ion and counterion attraction to their respective counterpart electrodes.

Any of the methods provided herein are for electrical biasing that provides a stable gating of the FET, corresponding to a gate voltage:

$$V_{gate} \sim \frac{1}{2} \times (V_{desalting1} + V_{desalting2}).$$

In an aspect, Vdesalting1 is a negative voltage having a magnitude greater than or equal to Vgate−0.5V and less than or equal to Vgate; Vdesalting2 is a positive voltage having a magnitude that is greater than or equal to Vgate and less than or equal to Vgate+0.5V; a net desalting voltage defined as Vdesalting2−Vdesalting1 is greater than or equal to 0V and less than or equal to 1V; and the net desalting voltage is maintained constant over a time period corresponding to analyte binding and sensing. Multiple electrode pairs may be electrically biased with the same Vdesalting1, Vdesalting2 and net desalting voltage.

In another embodiment, the invention is a device for carrying out any of the methods provided herein, such as for detecting an analyte in a sample solution. The device comprises a substrate; a field effect transistor (FET) supported by the substrate; a plurality of reference electrodes supported by the substrate and positioned in close proximity to the FET, wherein the plurality of reference electrodes comprises paired reference electrodes, each pair of reference electrodes having a first reference electrode and a second reference electrode opposably facing each other and separated by a separation distance, with the FET positioned between the paired reference electrodes; an electrical controller to electrically bias at least one reference electrode relative to the FET or to another reference electrode and generate a stable FET gate bias, to electronically remove at least a portion of charged ions in a sample solution from a sensor area and to generate a charged ion depletion region in the sensor area; and an electrical sensor to monitor a FET electrical parameter, wherein a change in the electrical parameter corresponds to presence of the analyte in the sample solution. In an aspect, the FET comprises a nanowire for sensing biological analytes.

The plurality of reference electrodes may comprise thin patterned metals having a high contact surface area for contacting and supporting a droplet of the sample solution, wherein the separation distance between paired reference electrodes is less than or equal to 30 μm. For example, the pair of reference electrodes may form a circle having a surface area that substantially corresponds to a droplet contact area. This may facilitate droplet spreading and flattening, to further improve the desalting effect of the energized reference electrodes.

In an aspect, the device comprises one or more pairs of non-circular electrodes that surround or partially surround the FET. In an aspect, the device comprises two pairs of non-circular reference electrodes that surround the FET.

In an aspect, a well surrounds the FET sensor and at least a portion of the reference electrodes for containing a droplet of sample solution. The well defines a well volume for holding the sample, the well volume that is less than 10 nL to confine a droplet of sample volume around the FET sensor and on the reference electrodes.

In an embodiment, the device further comprises platinum black on a contact surface of the reference electrodes to increase a surface roughness of the reference electrodes. The contact surface of the reference electrodes may comprise one or more of: electrodeposited platinum black; dendritic silver nanostructures; or platinum black nanotubes.

In an aspect, any of the disclosed FETs further comprise a source electrode and a drain electrode, and the sensor electrically connects the source and drain electrodes. An electrical parameter such as current, voltage, impedance or a parameter derived therefrom, is accordingly monitored or measured so as to detect presence of analyte interacting with the sensor.

In another embodiment, provided herein is a method for detecting an analyte in a sample solution, the method comprising the steps of: providing a field effect transistor (FET); providing a paired set of reference electrodes in close proximity to the FET with the FET positioned between the paired set of reference electrodes; introducing a droplet of the sample solution comprising charged ions to the FET and reference electrodes; electrically biasing at least one of the paired set of reference electrodes relative to the FET or to another reference electrode to electronically remove at least a portion of charged ions from a sensor area adjacent to a sensor of the FET, and thereby deplete charged ions in the sensor area; and monitoring a FET electrical parameter during the electrically biasing step, wherein a change in the electrical parameter corresponds to presence of analyte in the sample solution and a no change in the electrical parameter corresponds to absence of analyte in the sample, thereby detecting the presence or absence of analyte in the sample solution.

In an aspect, the droplet has a volume that is less than 50 nL. In an aspect, the droplet has a substantially flattened geometry. Such a flattened geometry further improves the desalting effect of the reference electrodes by placing essentially the entire droplet within a relatively strong electric field generated by the reference electrodes, and sufficiently strong to attract charged ions to the electrode surface irrespective of the location of within the droplet.

The droplet may be further characterized as having a contact surface area with the FET and the paired set of electrodes, wherein the contact surface area covers a contact surface of the FET and substantially all of a contact surface of the paired electrodes.

In an aspect, the fluid droplet provides a limited number of charged ions, thereby limiting back-filling of charged ions to the sensor area during the electrically biasing step. This is in contrast to bulk samples where the total volume is so high that there is continuous diffusion of a substantial number of charged ions to the depletion region and the sensor area. Such ion diffusion is also referred herein as back-filling.

In an embodiment, the fluid droplet has a volume and the paired set of reference electrodes has an electrode contact surface area in contact with the droplet, with a ratio of droplet volume to electrode contact surface area less than or equal to 1 μm.

In an aspect, the electrically biasing step depletes at least 50% of the total number of charged ions in the droplet. Such depletion may also be described in terms of an at least 50% effective reduction in the effective ionic strength of the solution surrounding the sensor and within the sensor area or the depletion region.

In an embodiment, any of the fluid droplets provided herein have a volume less than 1 nL. In an aspect, the electrode contact surface area is increased by a factor of about 10 by nanoprocessing of the electrode contact surface area.

Any of the methods provided herein further comprise the step of spreading the droplet over the electrode contact surface area. For example, the spreading may correspond to a spread droplet height that is less than or equal to 10% of a radius of a spherical droplet having an equivalent droplet volume. This spreading helps facilitate, in combination with the droplet volume, the electrode geometry, and the electric field strength, that substantially all charged particles throughout the spread droplet are attracted to the oppositely charged electrode, and thereby provides charged ion depletion throughout substantially all or all the droplet volume.

The spreading may be facilitated by any means known in the art, such as by providing a hydrophilic surface on at least a portion of the electrode contact surface area, by hydrophilic surface activation, or by self-assembled monolayers.

Particularly for spread droplets, the method may further comprise the addition of an additive to minimize evaporation of spread droplets, such as an additive that is glycerol.

In another embodiment, any of the methods and devices described herein may have reference electrodes that are surface patterned. For example, the invention may be a method for detection of an analyte in a sample solution, the method comprising the steps of providing a field effect transistor (FET); providing a paired set of reference electrodes in close proximity to the FET with the FET positioned between the paired set of reference electrodes, wherein the paired set of reference electrodes are surface patterned to increase an active working surface area of the reference electrodes; electrically biasing at least one of the paired set of reference electrodes relative to the FET or to another reference electrode to electronically remove at least a portion of charged ions from a sensor area adjacent to a sensor of the FET to the active working surface area, and thereby deplete charged ions in the sensor area; and monitoring a FET electrical parameter during the electrically biasing step, wherein a change in the electrical parameter corresponds to presence of analyte in the sample solution and a no change in the electrical parameter corresponds to absence of analyte in the sample, thereby detecting the presence or absence of analyte in the sample solution.

The surface pattern may comprise nanostructures. The surface patterning may be accomplished by one or more of: electrodeposition of platinum black on a smooth electrode surface to form a rough electrode surface; electroless etching crystalline silicon substrates to from silver dendritic nanowires and optionally converting the silver dendritic nanowires to platinum nanotubes; porous carbon electrodes; or deposition of carbon black.

In an aspect, the surface patterning increases the active working surface area by a factor of at least 50 compared to a corresponding surface area of reference electrodes having a smooth surface. In an aspect, the increase in the active working surface area can be described in terms of an increase in the desalting capacity of the system. For example, the increase in active working surface area may correspond to an at least 10-fold increase in a desalting capacity of the system, or, in other words, an at least 10-fold increase in desalting capacity of the reference electrodes compared to a corresponding smooth-surfaced electrode. "Desalting capacity" refers to the amount or net charge reduction in freely charged ions that are otherwise available to interfere with signal to the FET.

Any specifically described method herein may be combined with any other method described herein to arrive at an operable method. In an embodiment, provided is a device for carrying out any of the methods disclosed or claimed herein. In embodiment, provided is a method for detecting an analyte using any of the devices disclosed or claimed herein.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 2 are plots illustrating ISFET characteristics with on-chip electrodes and desalting for an NMOS device, showing (a) Id-Vg on/off characteristics of on-chip electrodes with desalting shifts compared with fluidic reference electrode, (b) measured desalting ionic current during sensor operation at various ionic strengths, and, Id-Vg characteristics in a large (34 nL) droplet at various ionic strengths with (c) 0.5 V desalting and (d) no desalting.

FIG. 6 illustrates two biasing configurations: Top panel is a two-electrode configuration; bottom panel is a four electrode configuration.

FIG. 7 are images of a desalting experiment with a sample having an ionic strength of 10 mM.

FIG. 8 are plots of normalized intensity for images of a desalting experiment at 10 mM (endpoints at 30 seconds). The solid lines represent forward excitation and the dashed lines reversed excitation.

FIG. 9 are plots of ionic current for a desalting experiment with a sample having an ionic strength of 10 mM.

FIG. 22A. Surface coverage and morphology for single electrode plating. Scale bar is 100 µm. Micrographs of high surface area electrodes fabricated by electrodeposition of Pt-black, showing (FIG. 22B) a pair of circular test electrodes and (FIG. 22C) around a FET device in wells.

FIG. 37. Schematic illustration of the limited scaling of charge uptake.

FIG. 41. Numerical model for calculating ion profiles during desalting.

V desalting bias. (e: negative) and (f: positive) ion distributions for 10 μM concentration at 0.4 V desalting bias respectively. (g: negative) and (h: positive) ion distributions for 1 mM concentration at 1 V desalting bias. Volume of droplet used for simulation is 300 pL and electrode area is 6100 μm². Note that (a) and (b) are in log scale, while the rest are in linear scale.

Figure 40:
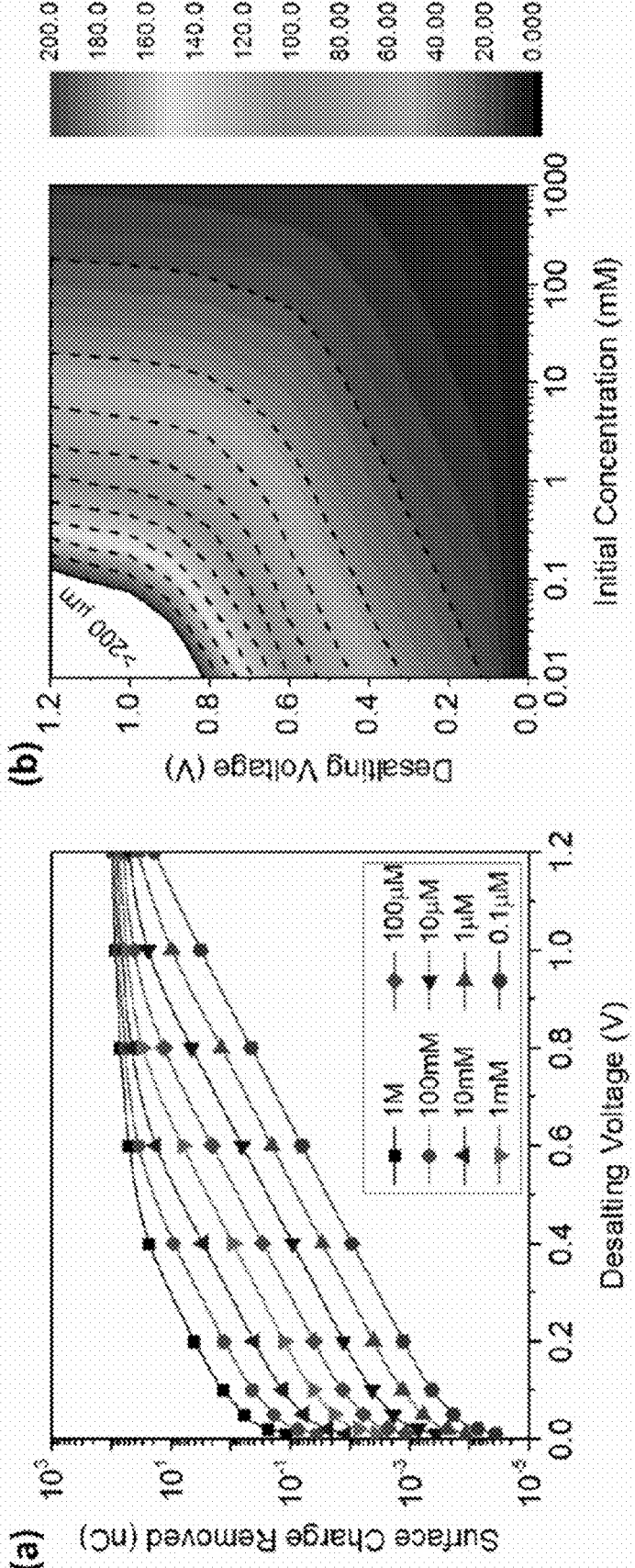
FIG. 40. Estimated desalting capacity of on-chip polarizable metal electrodes. (a) Plots of maximum surface excess ionic charge that may be absorbed into the EDL over an electrode ($10^4$ µm$^2$) from various solutions at non-Faradaic conditions. (b) Voltage-salt map of the limiting radius (projected) of an equivalent droplet that may be depleted to 1% of its ionic strength using these conditions, resulting in 10-fold increase in the Debye length over the sensor. Numerical calculation of ion profile showing negative ion density in a 300 pL droplet (6100 µm$^2$ electrode area) at (c) 1 µM and (d) 10 µM background strength under 1 V desalting bias. (e) Ion density at the center of the droplet is plotted as a function of salt concentration for different desalting bias: red (0 V), green (0.2V), blue (0.4V), black (0.6V), magenta (0.8 V) and cyan (1 V).
Figure 40:
Figure 47:
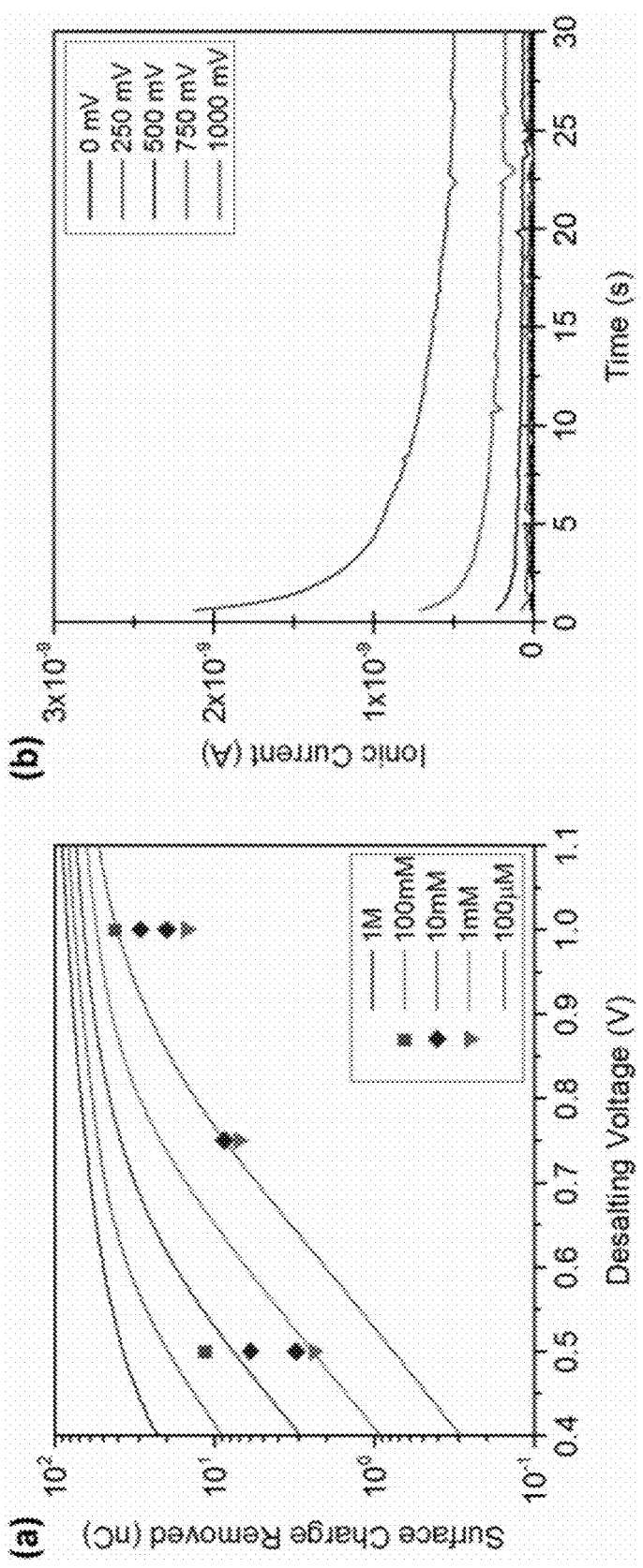

FIG. 47. (a) Plots of desalting capacity estimate from MPB model showing surface excess that can be absorbed in the diffuse EDL (magnified from FIG. 40(*a*)). Desalting data from experiments using sub-nanoliter control volumes has been overlaid for comparison with the theoretical estimate. Each data point is average of 3 separate experiments performed on different devices. (b) Typical ionic current decay measured during a desalting experiment in a 10 mM droplet using 2-electrode configuration of FIG. 1(*c*).

Figure 48:
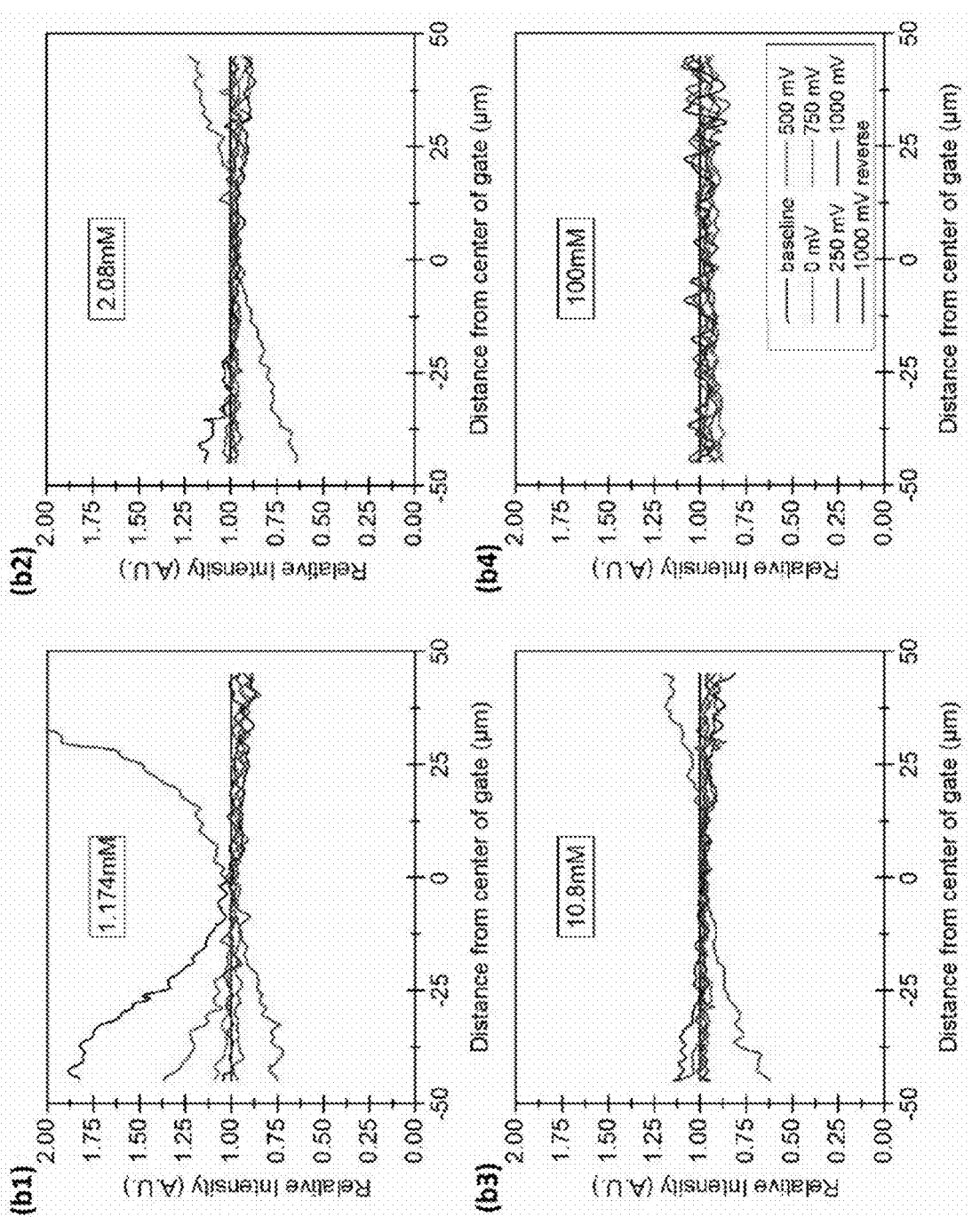

FIG. 48. (a1-a4) Images of desalting in a droplet ([NaCl] =1.174 mM) in 4-electrode configuration, using surface functionalized SNARF-5F dye. (b1-b4) Normalized intensity measurement of dye response over the device (spanning –28 μm to +28 μm) shows variation with desalting voltage at each ionic strength.

Figure 49:
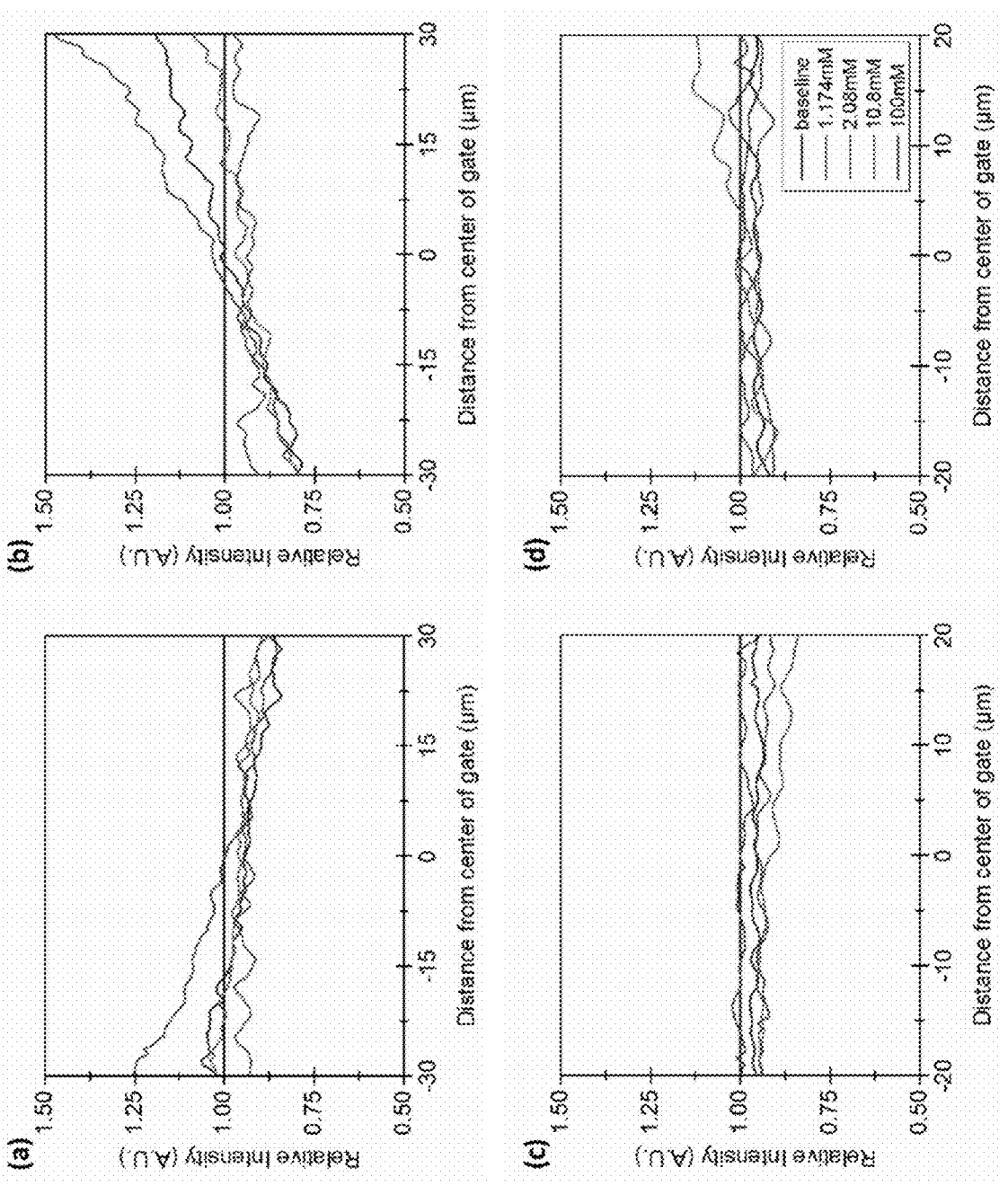

FIG. 49. Normalized fluorescence intensity of SNARF-5F dye response to ±1 V desalting, showing mean variations with ionic strength. (a) and (b: reversed voltage) show diagonal dye profile over the –28 μm to 28 μm device region using 4-electrode desalting configuration. (c) and (d: reversed voltage) show transverse dye profile over the –20 μm to 20 μm device region in 2-electrode desalting experiments.

Figure 50:
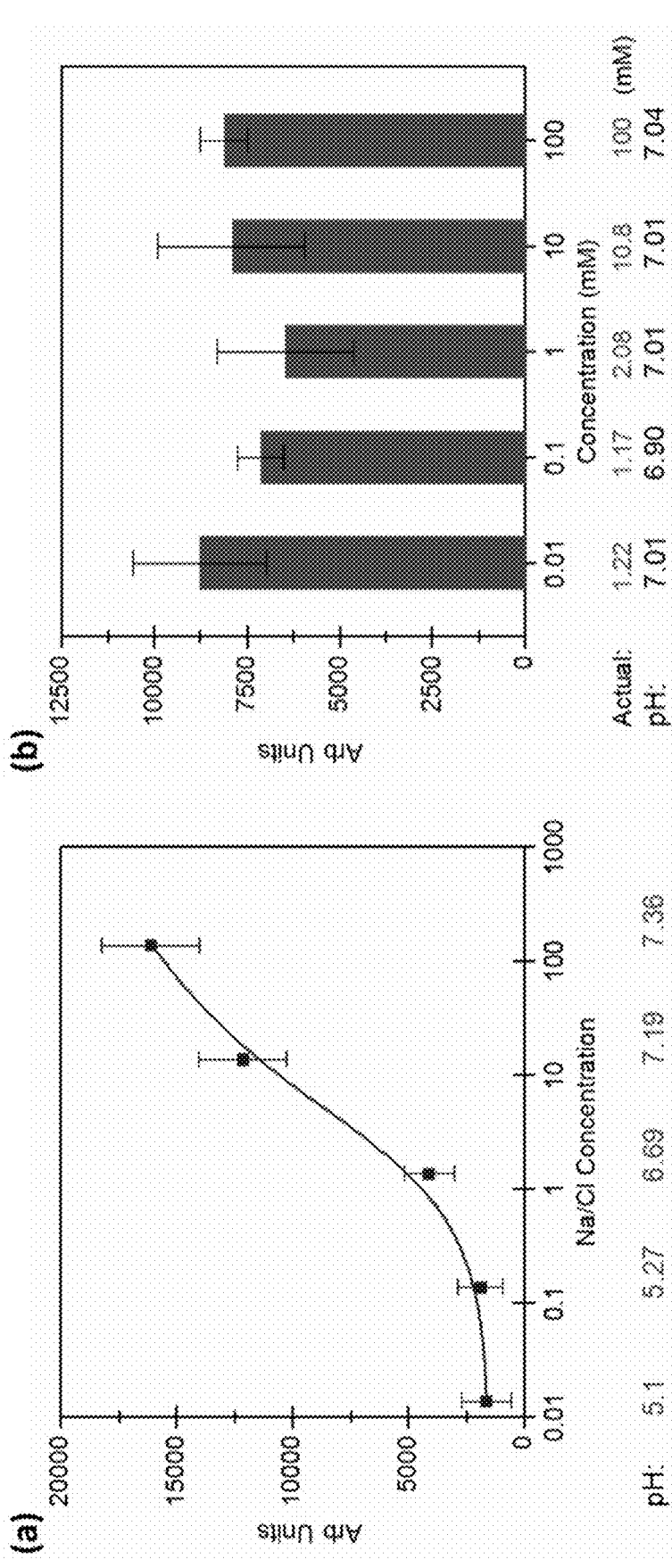

FIG. 50. Fluorescent response of SNARF-5F dye functionalized on a HfO₂ device surface for various ionic strengths. (a) without pH equalization and (b) with pH equalization.

Figure 51:
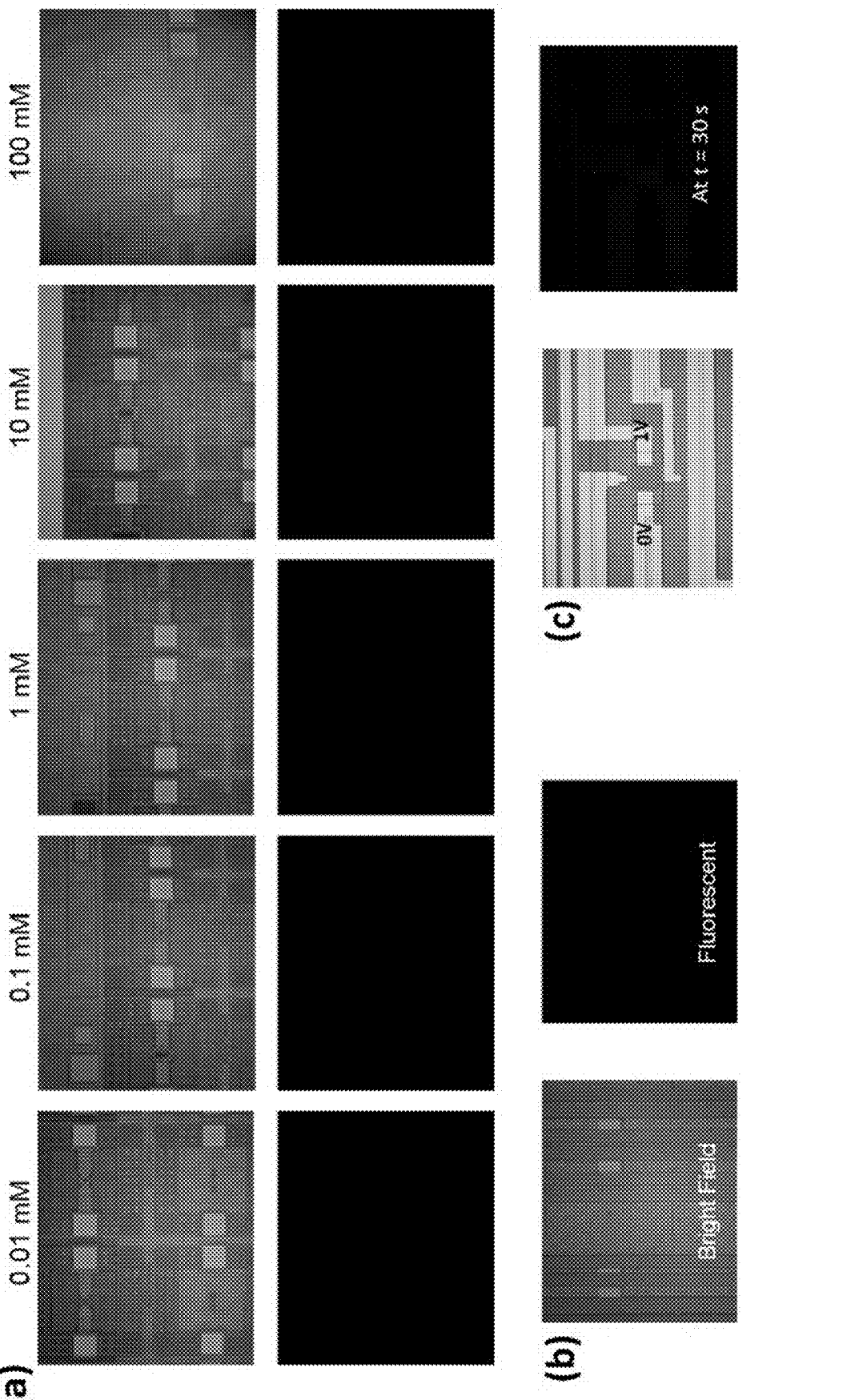

FIG. 51. Negative control experiments of SNARF-5F dye fluorescence. (a) shows droplets of various ionic strengths imaged in the absence of the dye (top row: bright field; bottom row: fluorescence), (b) shows the dye imaged a dry chip (no electrolyte) and (c) shows a device under 1 V applied bias when dry.

Figure 52:
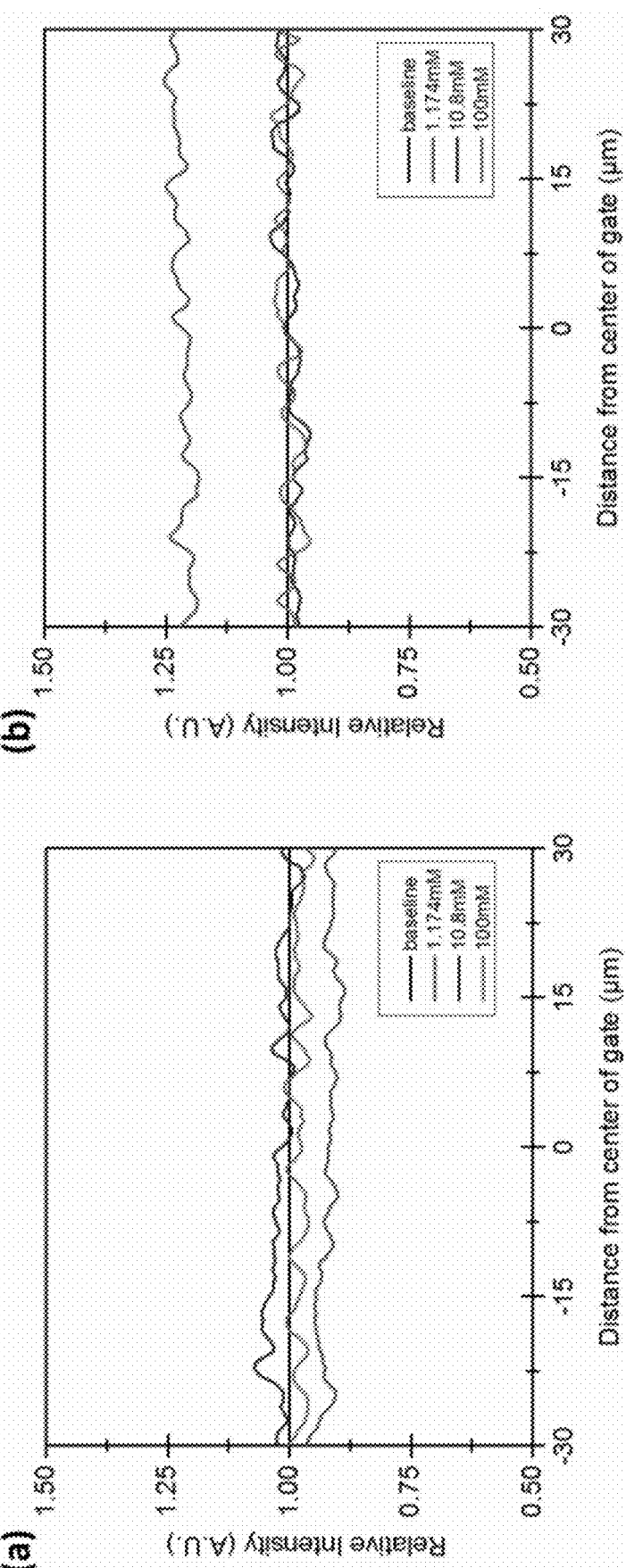

FIG. 52. Normalized fluorescence intensity of SNARF-5F dye response over the device region to desalting in a bulk well (150 μL), at different ionic strengths. (a) shows desalting response for 1 V bias and (b) shows the same when the applied voltage is reversed.

Figure 53:
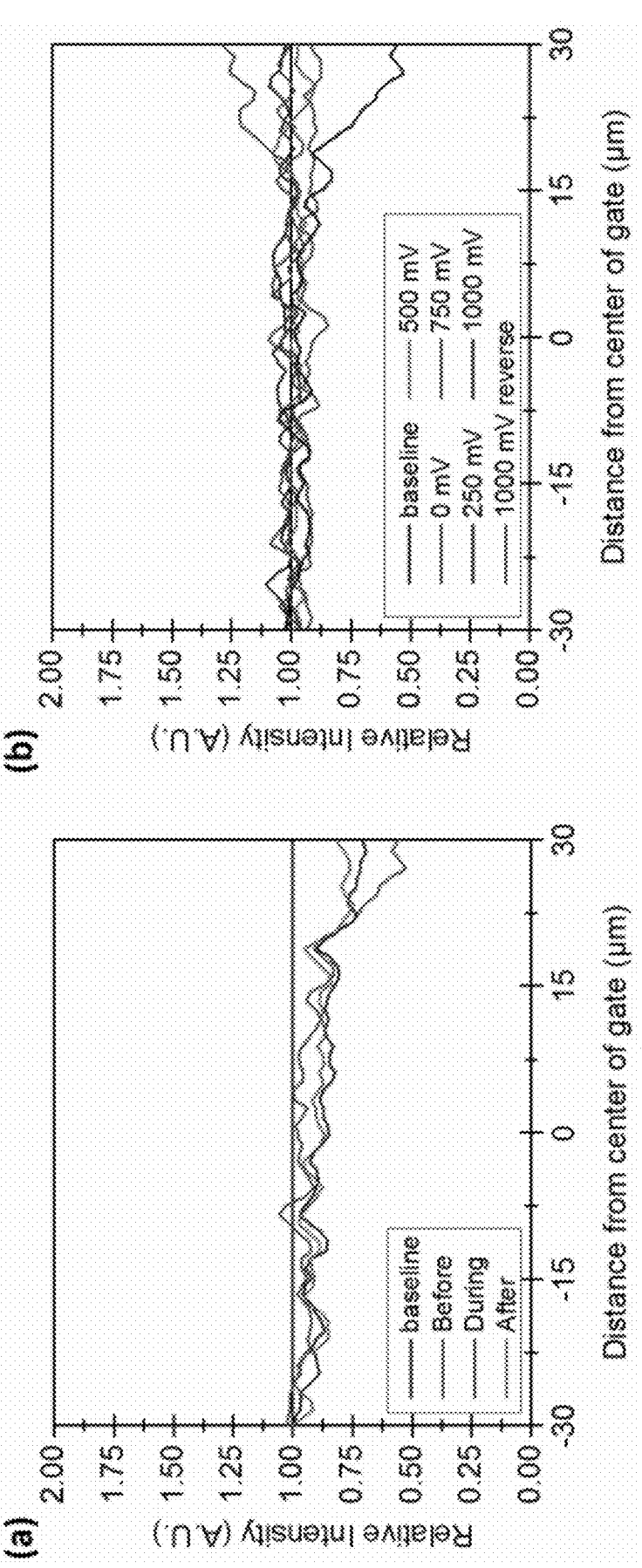

FIG. 53. Normalized fluorescence intensity of SNARF-5F dye response to desalting applied over the device region, for a deionized water droplet. (a) shows desalting response for 1 V bias and (b) shows variation with applied non-Faradaic bias in the 0-1 V range.

Figure 54A:
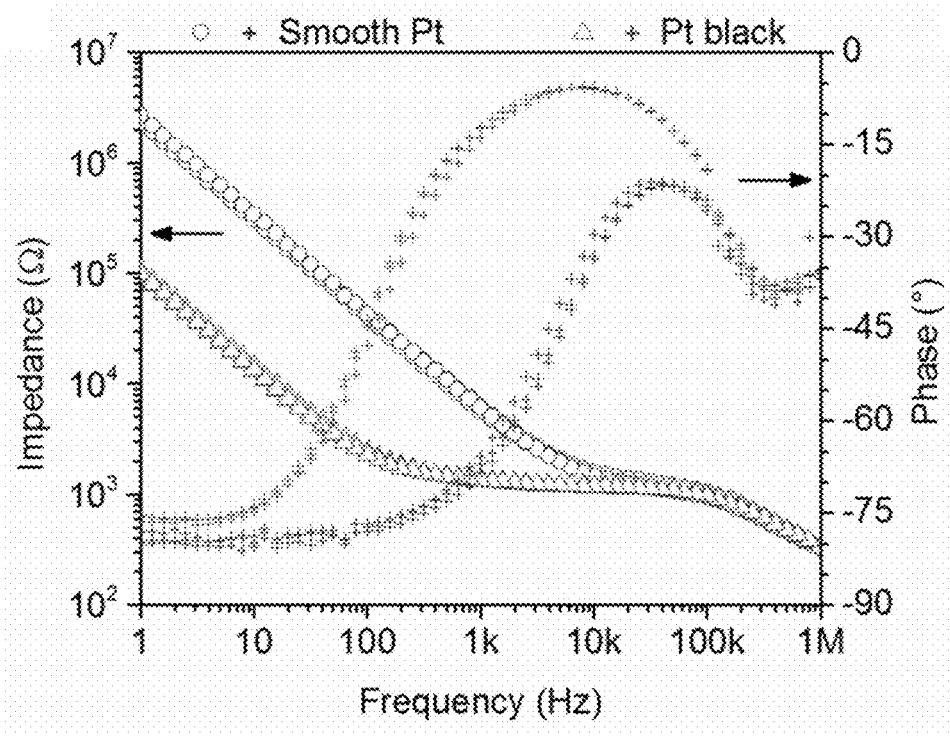
Figure 54B:
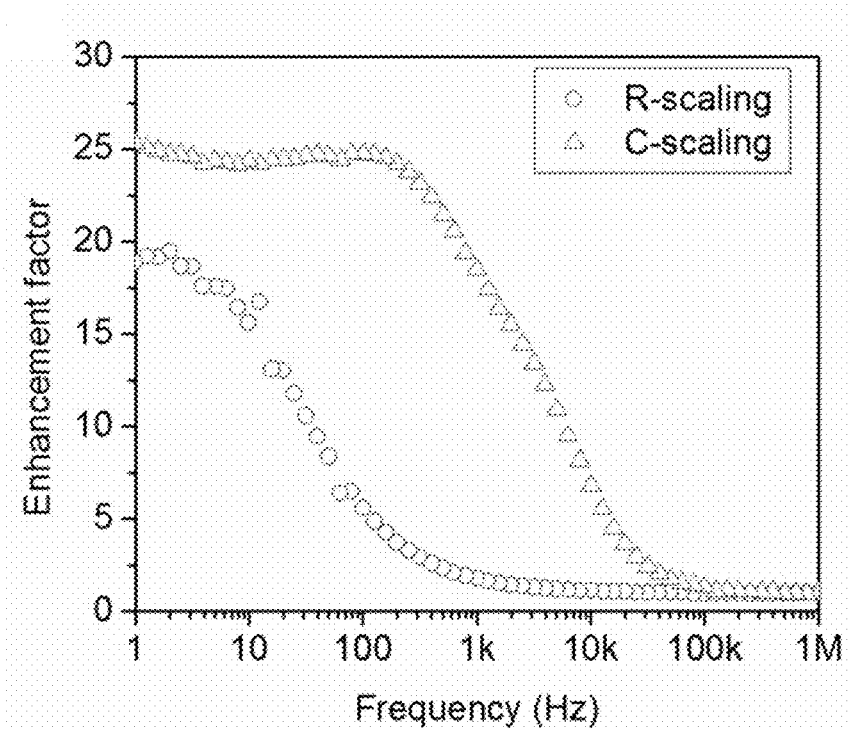
Figure 54C:
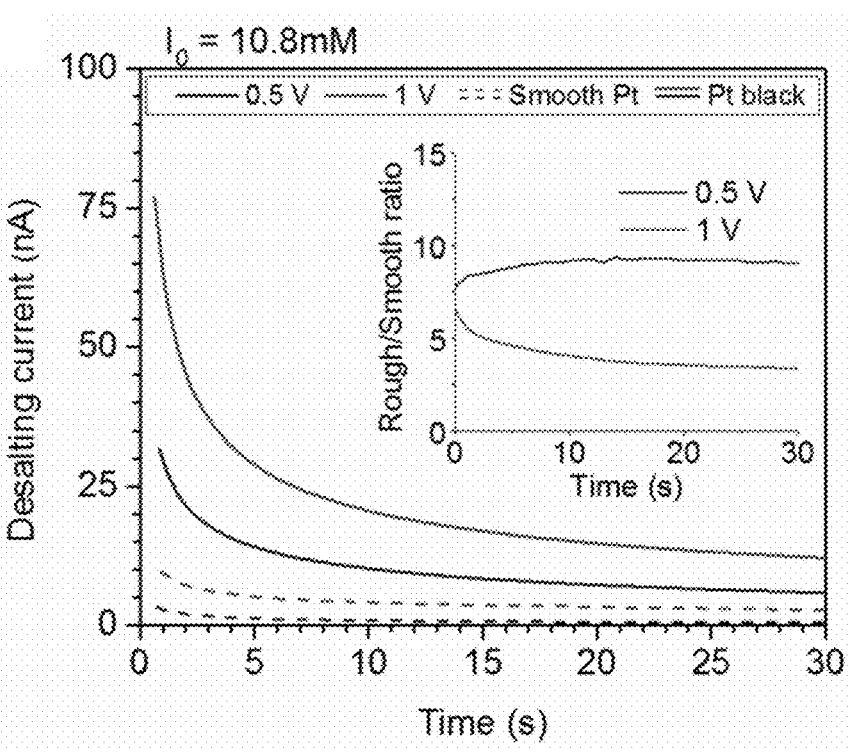
Figure 54D:
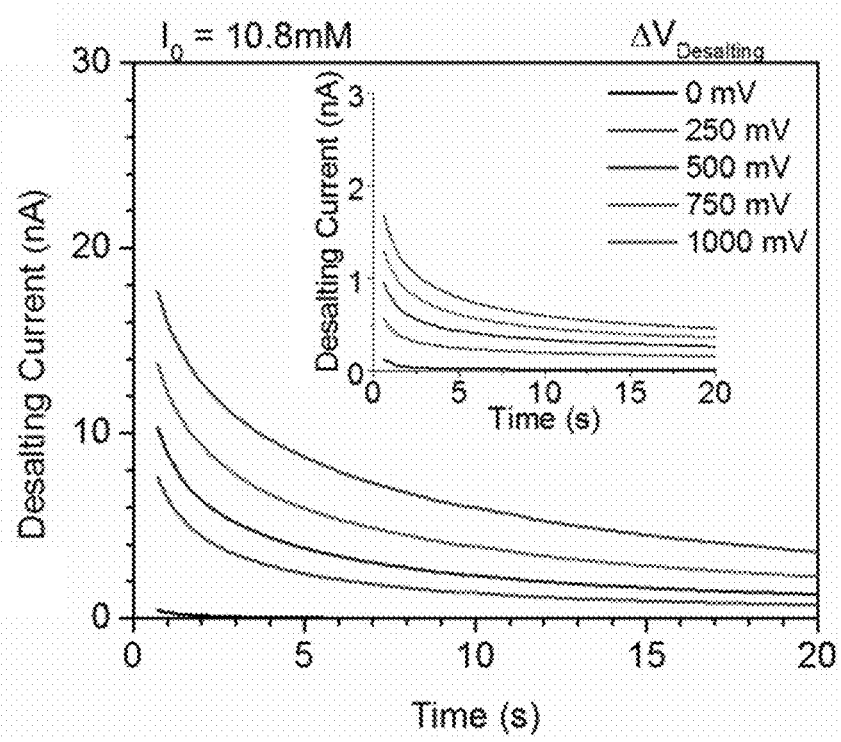

FIG. 54A-D. Electrical analysis of nanostructured electrodes. FIG. 54A. Bode plot of the EIS response in 1×PBS shows distinct improvement from smooth to Pt-black electrodes, observed by decrease in impedance at low frequency or relative shift in the phase minima. FIG. 54B. Shows ratio of the resistive (real) or capacitive (imaginary) components of the EIS spectra between Pt-black and smooth electrodes that determine the effective area enhancement. FIG. 54C. Using circular electrodes, ionic current during desalting scales from smooth (dotted) to Pt-black (solid) electrodes, with inset showing the rough/smooth ratio over time. FIG. 54D. Shows ionic current flowing between on-chip electrodes (Pt-black) as a function of the desalting voltage while operating a FET. Inset shows the same data for smooth electrodes.

Figure 55:
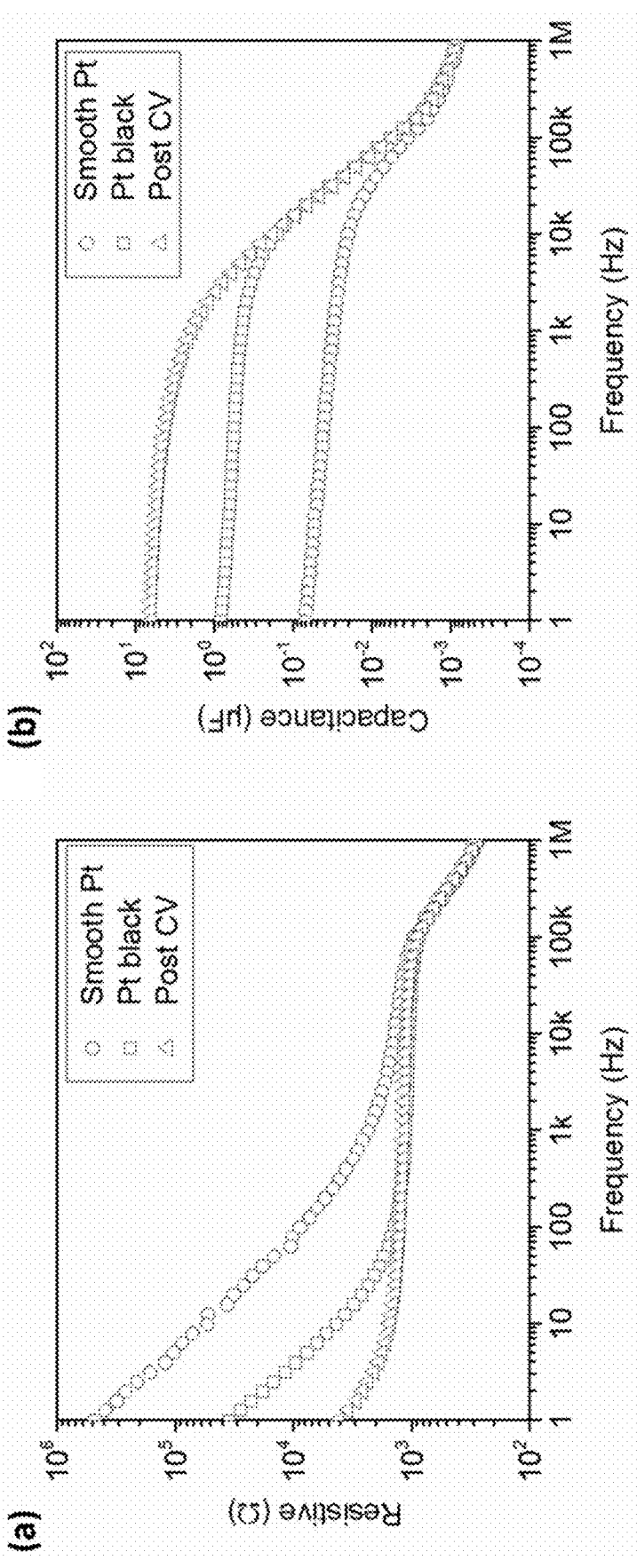

FIG. 55. Plot of (a) resistive (real) and (b) capacitive (imaginary) components from the EIS response versus frequency for a circular test electrode, showing response of smooth Pt, as deposited Pt-black and post CV-treated sample

DETAILED DESCRIPTION OF THE INVENTION

"Analyte" refers broadly to a material suspended in a fluid to be detected by the FET sensor. In an aspect, the analyte is a biological material and so is suspended within a fluid having a relatively high ionic strength.

"Field effect transistor" (FET) refers herein to a transistor having a sensor that detects changes in an electric field in and around the sensor. One unique feature of the instant FETs is that the gate corresponds to reference electrodes that are in close proximity to the FET, in contrast to conventional FETs having a gate corresponding to a fluidic reference electrode. FETs are also referred herein generally as ion-sensitive FETs (ISFETs) to emphasize the FET is sensitive to ions in the sample. Provided herein are devices and methods that minimize excess ions in the sample, particularly in the sensor area of the FET so as to increase FET sensitivity and accuracy. Any of the FETs provided herein may correspond to an ISFET. Any of the ISFETs provided herein may correspond more generally to a FET, as the systems provided herein may relate to molecular sensing and need not be confined to an indirect method like pH or other salt ions associated with ISFET measurements.

"Close proximity", in the context of reference electrodes and FET, refers to positioning of the reference electrodes so that upon energization, there is a detectable and substantial decrease in charged ions around the FET sensor, specifically the sensor area, including the sensor contact surface and region adjacent thereto in which analyte is capable of interacting with the sensor contact surface.

"Electrically biasing" refers to electrical energization of the reference electrodes. The biasing may correspond to one reference electrode having a positive potential and the other reference electrode of the pair having a negative electrode. The gate voltage accordingly is defined as $V_{gate}=0.5*(V_{desalting1}+V_{desalting2})$. Accordingly, the desalting voltages are selected to provide an appropriate gate voltage for analyte detection.

"Desalting" is used generically to refer to the removal of charged carriers, such as charged ions, dissolved salts, and other charged materials that interfere with the electrical detection of analyte by the FET. In an aspect, the analyte is provided an opportunity to interact with the sensor surface and then the reference electrodes are energized to deplete ions from the sensing region.

In the context of electrical biasing and monitoring, "simultaneous" refers to the energized reference electrodes that both desalt and provide the FET gate potential used to detect analyte.

"Sensor area" refers to that portion of the sensor and sample in which analyte is capable of interacting with the sensor to provide a detectable change in the FET electrical parameter. It includes, for example, the surface of the sensor and at least the region of the sample volume that an analyte interacting with the sensor extends thereto.

"Depletion region" is related to the sensor area and functionally describes a region in terms of the amount of charged ion that is removed. In an aspect, the depletion region corresponds to that region where at least 25%, at least 50%, at least 75% or at least 95% of charged ions are removed. Such a removal of charged ions results decreases electrostatic shielding of the sensor surface and associated sensor area, and thereby improves device sensitivity for detection of analyte by the FET. The depletion region may also be described in terms of the Debye screening length, defined by equation (1):

$$\lambda_D = \sqrt{\frac{\varepsilon k_B T}{2 N_A e^2 I}} \qquad (1)$$

where $\lambda_D$ is the Debye length, $N_A$ the Avogadro number, e the fundamental electronic charge, I the ionic strength, T the temperature, $\varepsilon$ the electrical permittivity, $k_B$ the Boltzmann's constant. Typically, for physiological solutions, the Debye length is about 1 nm or less. This means that for analytes that extend more than about 1 nm from the sensor surface into the sample volume, any electrostatic effects outside the Debye length tend to be screened or shielded from detection by the excess free charge. The instant invention presents novel mechanisms for avoiding or significantly reducing this by effectively, for example, increasing the Debye length by effectively minimizing ionic strength, I, in equation (1). This is achieved by removing charged ions from the sensor area to provide a depleted charged ion region where sensor detection occurs. In this manner, device sensitivity is improved dramatically.

"FET electrical parameter" refers to such as current, voltage, impedance or a parameter calculated therefrom that reflects analyte interaction with the FET sensor.

"Physiological level" of salts refers to a solution that is isotonic relative to a biological material, so that the biological analyte does not adversely swell or shrink under osmotic pressure.

"Minimally processed" refers to a biological sample that may be provided to the devices herein without any complex processing steps and so may be suitable for field use where equipment such as centrifuges, refrigerators, heaters, and other equipment associated with fluid processing is not readily available. One example of a process that is considered minimal is sample dilution by introduction of a physiologically-compatible fluid, such as a solution isotonic to biological materials suspended within the sample, such as PBS or equivalents thereof.

"Functionalized" is used broadly to refer to processing of the sensor or sensing surface to facilitate interaction or binding between an analyte and the sensing surface. The processing is dependent on the analyte being measured. For example, an antibody, a receptor, a polynucleotide, a polypeptide, or other target-specific material may be attached to the sensing surface to provide analyte-specific binding.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

Example 1

Electronic Desalting and Voltage Biasing for Label Free Electronic Biomolecular Detection Using ISFET Sensors Provided herein are novel methods and devices for sensing with ion-sensitive-field-effect-transistors (ISFET) that achieve improved sensor responses and approaches for label free molecular detection. The technique engages ISFETs within a solution by the use of locally patterned on-chip metal reference electrodes. The methods and devices use metal electrode on-chip: i) to locally and individually turn on and operate an ISFET using on chip metal electrodes in fluid; ii) for using multiple such electrodes and varying the electrical bias between them to adsorb ions and electronically desalt the region around the ISFET—in order to address a fundamental limitation and improve the device sensitivity; iii) miniaturizing and optimizing the geometry of the ISFET and on-chip electrodes to perform desalting as well as sensing within a droplet so as to facilitate scalabilty into arrays of ISFETs; iv) optimal biasing conditions that establish a stable gate voltage and regimes in which the droplet can be effectively depleted of background salts ions to facilitate the biomolecular charge sensing; v) for increased surface area electrodes to maximize the desalting efficiency.

Conventionally, an ISFET comprises of a transistor whose gate is exposed to an ionic medium, with the gate voltage that determines conduction within the device being applied by a fluidic standard reference electrode. Sensing is accomplished by performing reactions of interest that lead to changes in the concentration of a specific ion or pH which, in turn, modulates the gate voltage of the ISFET. The methods and devices provided herein replace the fluidic reference electrode by patterning (through lithography and microfabrication methods) metal on-chip microelectrodes in close proximity to the ISFET.

Using multiples of such metal electrodes around a device, and appropriate electrical biasing of these on-chip electrodes—both relative to the device—as well as to each other, it is possible to electronically desalt and deplete the region surrounding an ISFET and at the same time apply a gate potential to operate the device—thereby facilitating simultaneous control of an ionic environment as well as sensing within that as the same time. With patterning high surface area electrodes, desalting efficiency is maximized.

Miniaturization of the reference electrodes that function as the gate electrode, facilitates sensing within a droplet that can be substantially electrically depleted charged ions so that the surface of the ISFET can respond to ionic and molecular changes in the vicinity with improved sensitivity. Arrays of thousands of such ISFETs on a single biosensor chip, each with their own on-chip desalting/gating electrodes and encapsulated in a tiny droplet, can be individually and independently operated to achieve multiplexed detection.

Features and benefits of the instant invention include: a) Precise tuning and control of the ionic microenvironment around a biosensor at low voltage to: i) deplete the region of ionic species without the need for Faradaic reactions that could interfere with sensing and cause damage to the device; ii) increase surface area electrodes that improve desalting efficiency by absorbing more ions; iii) lower the detection limits using the FET; b) Species detection within a droplet to: i) minimize the analyte quantities needed for detection; ii) independently and simultaneously address an array of FETs for increased throughput with parallel screening for multiple analytes; c) Simultaneous detection with electronic desalting of the sample with the on-chip electrodes simplify device construction and eliminates the need for complex electronics for high-speed switching between desalting and sensing steps; d) An improved method of establishing a stable gate potential in solution by the use of multiple electrodes and voltage offsets between them; e) Detection of biomolecules and target analytes approaching physiological concentrations that minimize complexity and time associated with sample preparation and washing The invention addresses the need to perform desalting around an electronic biosensor. Whereas physiological fluids, e.g. blood, plasma, serum etc., are high in ionic content, approaching 270-280 millimolar, the large excess of ions interferes strongly with sensing by electrostatically shielding the sensor surface from detecting charged species that are produced in sensing reactions. For example, in a DNA hybridization reaction over a sensor, negative charges are added or a change in pH follows when a target DNA strand (1-10 nm) undergoes hybridization with a capture probe that is functionalized on the sensor surface. However, most of these charges lie outside the Debye screening length (described in equation (1), $\lambda_D$<1 nm) and hence do not actively participate in modulating the gate voltage of the ISFET through which changes in conduction are sensed.

A persistent challenge is the design of a scheme that will enable the application of this gate voltage and extend the Debye length far enough into solution so as to include and detect all possible ionic changes near the sensor surface. Equation (2) is used to estimate the maximum ionic charge that can be absorbed (assuming quasi-equilibrium) from solution on the surface of an electrode by applying a voltage $\psi$.

$$\sigma_D = -\text{sgn}(\psi_D)2N_A e C_o \lambda_D \sqrt{\frac{2}{v}\ln\left[1 + 2v\sinh^2\left(\frac{F\psi_D}{2RT}\right)\right]} \ C/m^2 \quad (2)$$

where, $C_o$ is the bulk ionic concentration, v the packing fraction, F the Faraday's constant and R the universal gas constant. As electrode dimensions approach the order of tens to hundreds of microns that is typical of length scales in ISFET devices, the maximum volume that can be effectively desalted is limited to sub-nanoliter quantities. Hence, it is useful to perform sensing within droplets. For example, a 100 μm×100 μm electrode area at 1 V can be used for desalting a ca. 200-300 μm diameter droplet that contains about 1 nL. However, establishing a solution potential within such a tiny droplet is not feasible with conventional reference electrodes.

Figure 1:
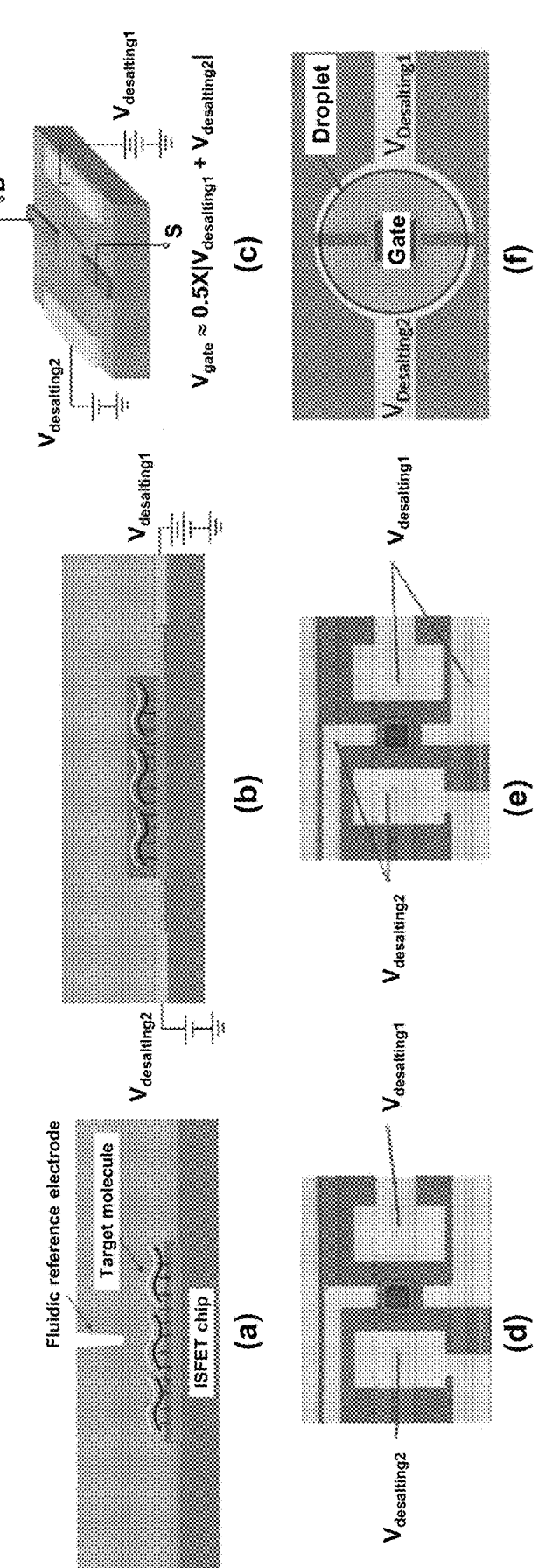
FIG. 1 is a schematic of sensing using ISFET with on-chip electrodes and desalting, showing (a) conventional ISFET, (b) on-chip desalting electrodes replace reference electrode, (c) biasing schematic with desalting voltages and apparent gate voltage, and, micrographs and biasing optimizations with (d) 1-pair, (e) 2-pair and (f) circular on-chip electrodes.

FIG. 1 describes schematics of a method for realizing a new ISFET biosensing device. FIG. 1(a) shows a conventional ISFET using a fluidic reference electrode to apply gate voltage. In this configuration, the detected target molecules are mostly outside the Debye length (shown in green) and hence only passively contribute to the uncompensated resistance against the gating voltage from the reference electrode. Over the last three decades of ISFETs, not much has changed in this basic operating scheme. The instance concept (FIG. 1(b)), however, replaces the reference electrode with pair(s) of on-chip metal desalting/gate electrodes. FIG. 1(c) depicts the biasing schematic and FIG. 1(d) shows a test device consisting of a commercial transistor chip with four platinum metal electrodes patterned around the sensor. By applying a voltage between two metal electrodes, electronic desalting is achieved as oppositely charged ions migrate from the bulk towards the surface of either metal electrode. At the same time, the electrical potential in bulk due to the application of this described voltage is the average of the two desalting potentials. This establishes well-defined gate voltage in solution and can be controlled through the choice of desalting potentials. In this way, the desalting voltage depletes the ions to increase the Debye length so that the target molecules and ions are encapsulated within the green sensing zone in which they actively contribute towards modulating the ISFET when a sensing reaction occurs and charges are incorporated.

FIGS. 1(e-f) show further optimizations to design and placement, by the use of multiple electrode pairs and symmetric circular electrodes surrounding the sensor, in order to maximize the desalting region over the sensor area and within an entire droplet. The circular split-ring electrode design also allows symmetric droplet confinement due to preferred adhesion of an aqueous droplet over the metal surface against the rest of the chip. Increased surface area electrodes, with nanoscale surface roughness and porosity provide greater surface-area to volume enhancement for increased desalting efficiency.

FIG. 2 shows electrical characteristics obtained by biasing the ISFET through the on-chip metal electrodes. FIG. 2(a) compares the characteristics of a fluidic reference electrode gate with the on-chip metal electrode biasing scheme. Each curve shows an average of 5 dual (forward and reverse) voltage sweeps and the device turns on with excellent stability and repeatability. By virtue of applying different desalting voltages, the transfer curves shift with respect to the metal electrode and are in accordance with the apparent gate voltage. FIG. 2(b) shows the measured ionic current between the on-chip metal electrodes that is indicative of the capacitive charging that leads to desalting in the droplet. The sharp drop over time is dominated by contribution of the ionic current and there is minimal gate leakage from the ISFET. FIG. 2(c) compares the desalting effect at 0.5 V with FIG. 2(d) at 0 V for various ionic strengths in a large droplet. Note that the threshold voltages are all shifted in the former by an equivalent value to the desalting voltage. The device shows maximum response and shifts at 0.1 mM ionic strength where an effective change in the Debye length (ca. 43%) is calculated using the charge separation from the measured ionic current. Further, this effect extends to higher concentrations within smaller droplets that carry limited ionic charge.

Desalting measurements around sensor region: Effectiveness of desalting with metal electrodes is tested in a microdroplet (ca. 400 pl. volume) using an ion/pH sensitive dye (known to fluoresce well within the 5-8 pH range) under neutral pH conditions as a function of ionic concentrations. The dye is attached to the surface functionalized chip via well-known surface chemistry. FIG. 3(a) shows a device spotted with a microdroplet and FIGS. 3(b) and (c) show fluorescent response of the device under desalting after 30 seconds. Both 2-electrode (FIG. 3(b)) as well as 4-electrode (FIG. 3(c)) configurations are tested, and at 10 mM and 1 mM respectively. In both cases, ionic activity consistent with desalting voltages is observed.

Measured relative changes in the fluorescent response of the dye to the desalting conditions are analyzed over the sensor region. While this region falls within the bulk of the droplet, a net change in the fluorescence over the gate reflects depletion over the region of interest. FIG. 4(a) shows the desalting response at different voltages (including 0 V and –1 V controls) for a 1 mM ionic strength system. The measured change consistently tracks the magnitude of the desalting voltage and the fluorescence portioning follows the 4-electrode diagonal symmetry. Further, significant desalting is achieved at 0.75 and 1 V biasing conditions and the –1 V case shows expected reversal symmetry. FIG. 4(b) compares measured relative fluorescence of the desalting profile over the gate at 1 V for three different ionic strengths. The desalting effect is most prominent at the lowest ionic strength and also observed are apparent depletion at 10 mM. Importantly, this is performed at low non-Faradaic voltages where issues arising from gas bubbles and corrosive byproducts of aqueous/metal redox reactions as well as heating that could interfere with the device operation as well as damage the FET are avoided.

Figure 3:
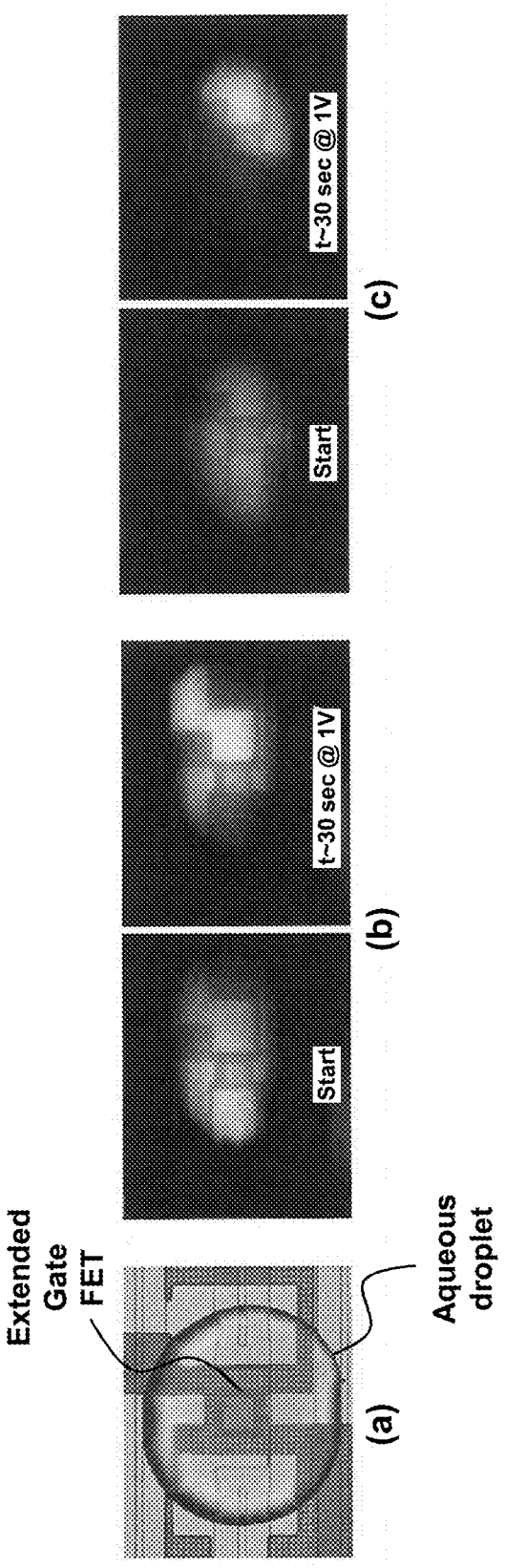
FIG. 3 are dye visualization images of on-chip desalting (a) about 400 pL droplet on chip, and, desalting at 1 V with (b) 2-electrode (see FIG. 1($d$)) and 4-electrode (see FIG. 1($e$)) configurations; fluorescence enhances with cations and diminishes with anions.
Figure 4:
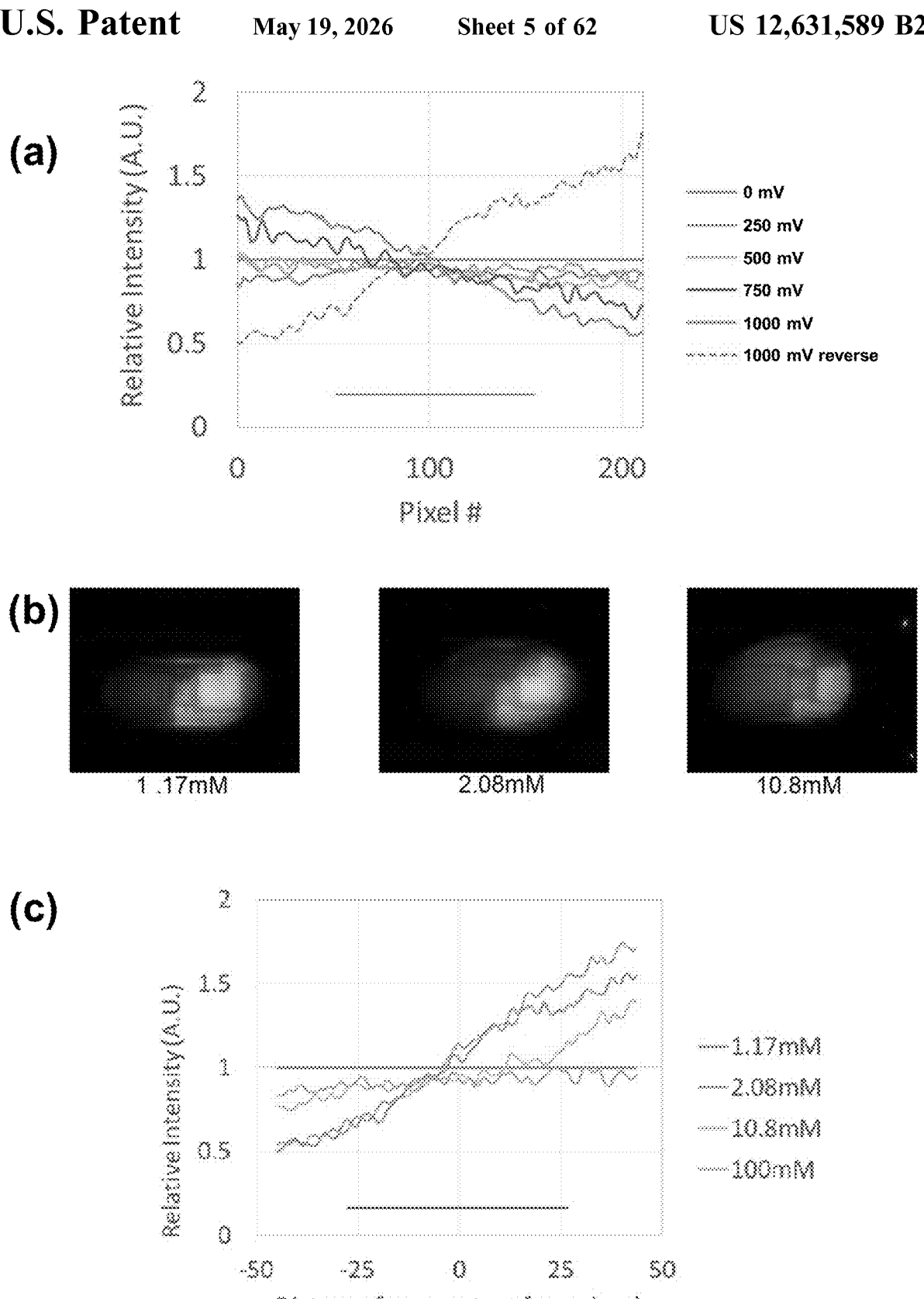
FIG. 4 illustrates measured desalting performance of ion depletion and portioning over the sensor gate region in a 4-electrode configuration showing (a) voltage dependence at an ionic strength of about 1 mM and (b) ionic strength dependence at −1 V. The red line at the bottom of the graph indicates a diagonal profile (57 μm) across the square sensing pad and each pixel spans about 0.5 μm.

The results shown in FIGS. 2-4 support the new design of ISFET and molecular sensing in droplets using a novel on-chip multielectrode scheme that can simultaneously perform electronic desalting as well as FET operation—both of which are important for high sensitivity towards direct molecular detection with ISFET in a droplet.

Development of ISFETs for biosensing, particularly pH and the theory associated with the pH response of these devices is described by Bergveld [1-2]. See also: Y. Cui, Q. Wei, H. Park, and C. M. Lieber, "Nanowire Nanosensors for Highly Sensitive and Selective Detection of Biological and Chemical Species," Science, vol. 293, no. 5533, pp. 1289-1292, August 2001, incorporated specifically herein for nanowire-based FETs for molecular sensing. The layout of ISFET biosensor assembly, with the use of a bulky reference electrode for gate biasing is the accepted standard. Disadvantages of this configuration is that in order for a charge on a biomolecule to induce changes in the electric field around the sensor and in the conduction of the FET, these systems work with low ionic strength electrolytes that are unfavorable for reactions such as DNA hybridization. Van den Berg et al. [3], demonstrated miniaturized Ag/AgCl reference electrodes for use in ISFET pH sensors. However, their performance was strongly dependent and limited by uniformity issues at the wafer scale as well as the electrolytes that were used. Recently, fully integrated CMOS device was demonstrated by Rothberg et al. [4] for genome sequencing using very large-scale array of ISFETs in a conventional gating scheme. However, it will be beneficial to localize the reactions and maximize the efficacy and sensitivity using on-chip electrodes in such a system. Guan et al. [5] have demonstrated complex gating strategies in nanochannel ionic diodes, but they too work best at low ionic strengths (~1 mM).

In previous work, we demonstrate design and performance improvements in the development of ISFET sensors [6-8] as well as biosensors operating in sub-nanoliter droplets with localized DNA melting and sensing reactions [9].

Desalting methods such as capacitive deionization and membrane electrodialysis have been widely studied in the context of water desalination and energy recovery from brackish water [10-11]. Significant limitations to these methods include the need for faradaic overpotentials that can cause undesirable heat and gas generation and large back-pressure in membranes that limit their performance.

Demonstrated herein is an ISFET sensor in a droplet with stable gate voltage established using pairs of on-chip metal electrodes. At the same time, also observed are electronic desalting of a droplet using this process which will lead to improvement in sensitivity and performance. The supporting data provide useful information for further optimizations of electrode design—placement, geometry and optimal biasing conditions.

References for Example 1

1. P. Bergveld, "Thirty years of ISFETOLOGY, What happened in the past 30 years and what may happen in the next 30 years," Sensors and Actuators B: Chemical 88 (2003): 1-20.

2. P. Bergveld, "The development and application of FET-based biosensors." Biosensors 2(1) (1986): 15-33.
3. A. van den Berg et al., "A micro-volume open liquid-junction reference electrode for pH-ISFETs." Sensors and Actuators B: Chemical 1 (1990): 425-432.
4. J. M. Rothberg et al., "An integrated semiconductor device enabling non-optical genome sequencing," Nature, 475 (2011): 348-352.
5. W. Guan et al., "Field-effect reconfigurable nanofluidic ionic diodes," Nature Communications, 2 (2011): 506.
6. B. R. Dorvel et al., "Fabrication of High-k Hafnium Oxide Based Silicon Nanowires for Sensitive Detection of Small Nucleic Acid Oligomers," ACS Nano, 6(7) (2012): 6150-6164.
7. J. Go et al., "Coupled Heterogeneous 'Nanowire-Nanoplate' Planar Transistor Sensors for Giant (>10V/pH) Nernst Response," ACS Nano, 6(7) (2012): 5972-5979.
8. B. Reddy, Jr. et al., "High-k dielectric $Al_2O_3$ nanowire and nanoplate field effect sensors for improved pH sensing," Biomed Microdevices, 13(2) (2011): 335-344.
9. E. Salm et al., "Ultra-localized Thermal Reactions in Sub-Nanoliter Droplets-in-Air," PNAS, 110 (2013): 3310-3315.
10. T. J. Welgemoed, C. F. Schutte, "Capacitive Deionization Technology™: An alternative desalination solution," Desalination, 183(1) (2005: 327-340.
11. V. M. Barragan et al., "Effect of an AC perturbation on a desalination electrodialysis process," Desalination, 142 (2002): 235-244.

Example 2

Characterization of NanoFETs With On-Chip Platinum Electrodes

NanoFETs and on-chip platinum electrodes are examined to further explore and characterize device and biasing schematics. Dye visualization is employed to examine desalting around the devices, including MQAE ($Cl^-$) and SNARF-5F (pH) dyes (see FIG. 5). Further explored are multiple pairs of reference electrodes that surround the FET. To characterize biasing conditions, one electrode is swept while the second electrode of the pair is grounded; and both reference electrodes are swept with an offset. The biasing experiments indicate a fixed desalting voltage with respect to the gate voltage is more stable. This can eliminate interference associated with FET on/off behavior and also eliminates Faradaic overpotential when at large gate voltages.

Figure 5:
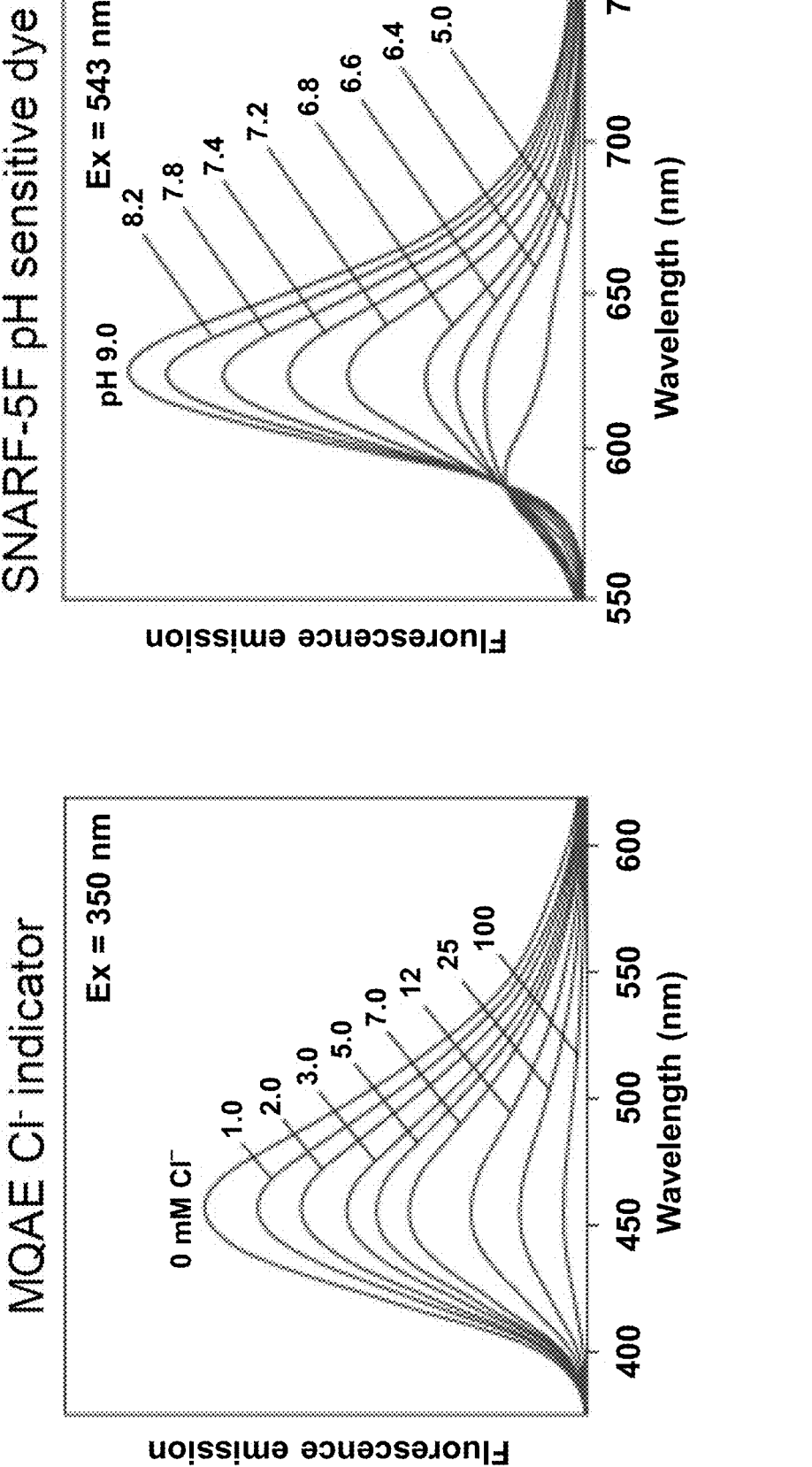
FIG. 5 are fluorescence emission spectra of ion-sensitive (left panel) and pH-sensitive (right panel) dye for use in visualization of the systems and methods provided herein.
Figure 10:
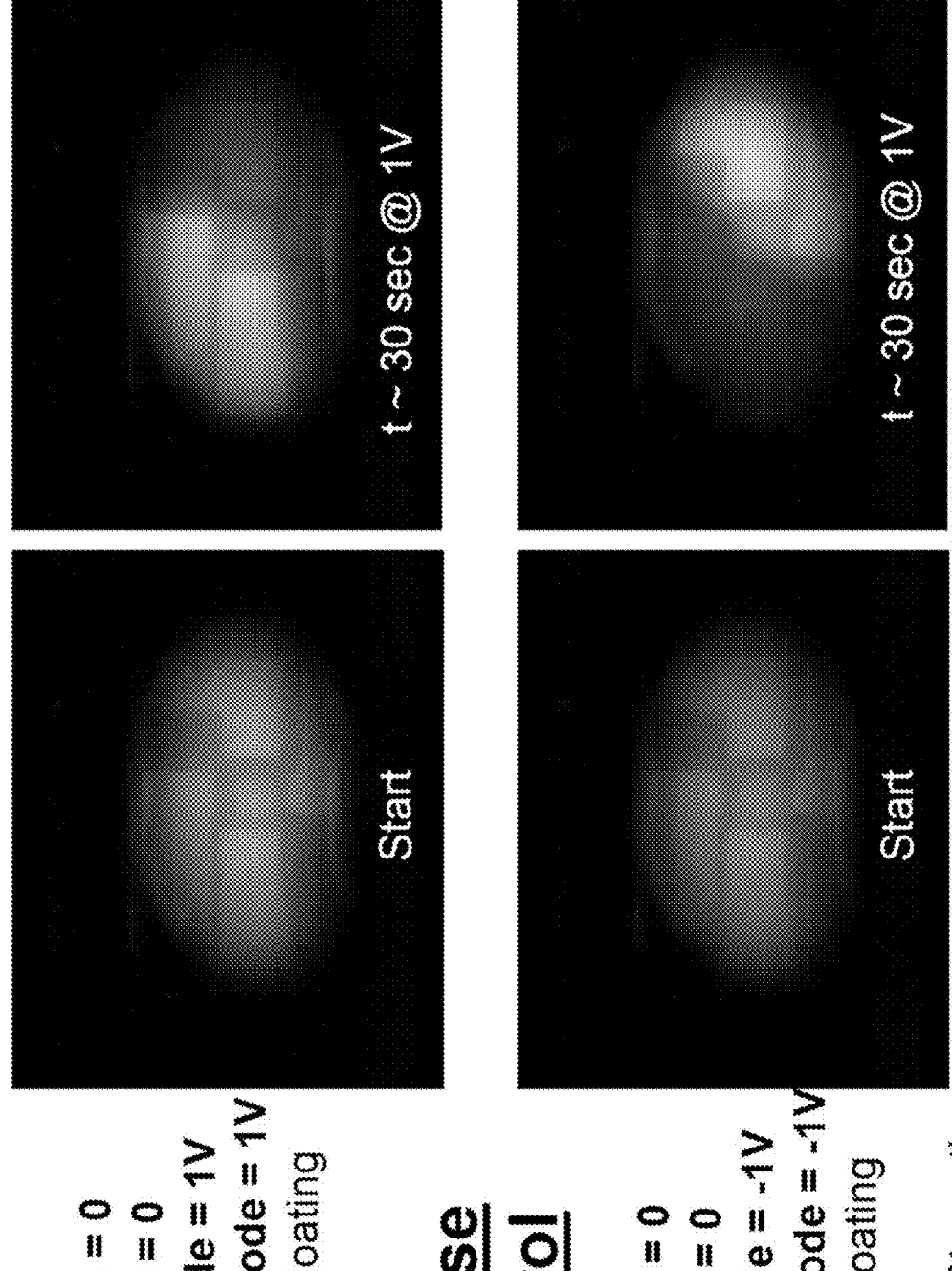
FIG. 10 are images of a four electrode desalting experiment at 1.17 mM (pH neutral).
Figure 11:
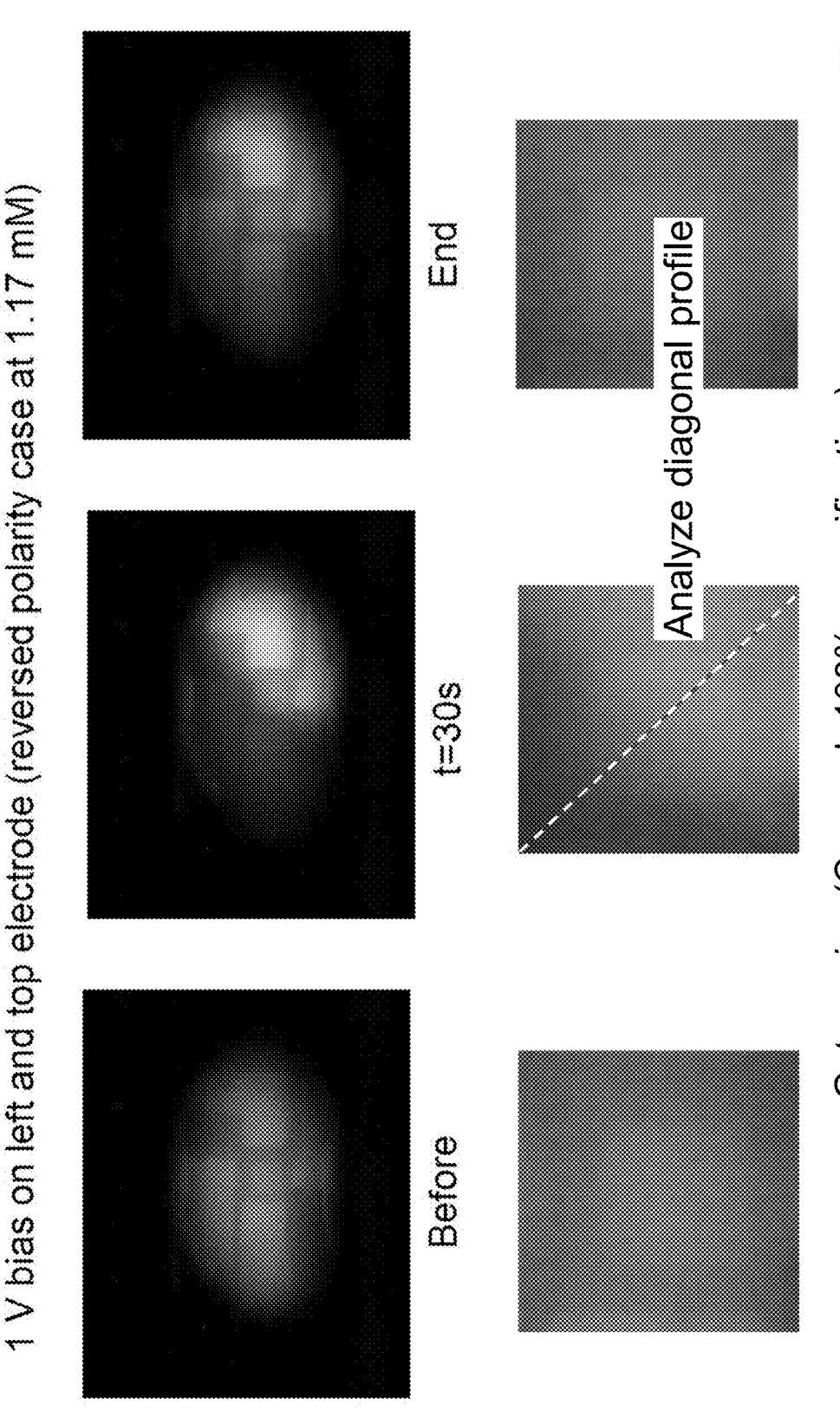
FIG. 11 are images of a four electrode desalting experiment in the device region during desalting for a 1.17 mM ionic strength sample.
Figure 12:
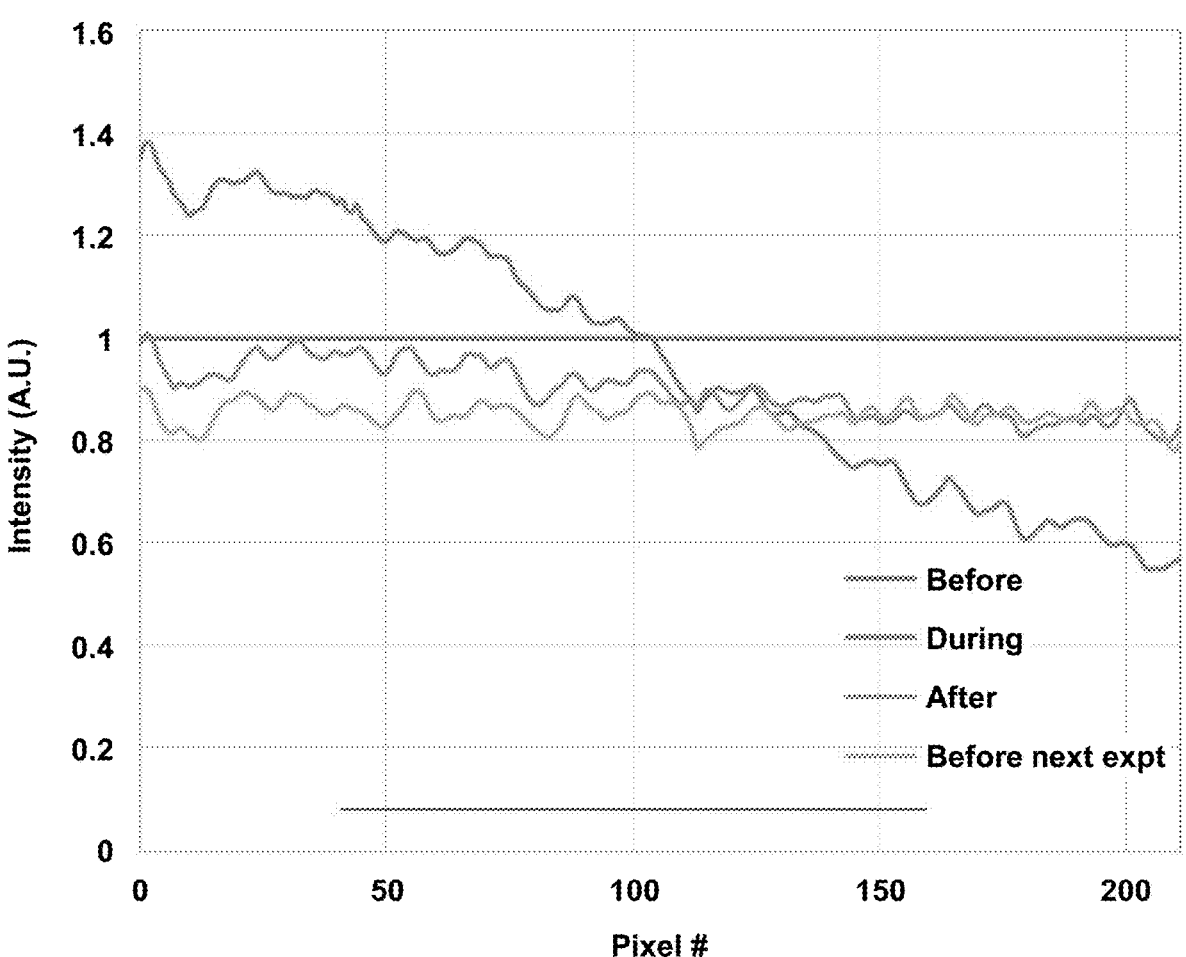
FIG. 12 is a plot of intensity over the diagonal line illustrated in FIG. 11.
Figure 13:
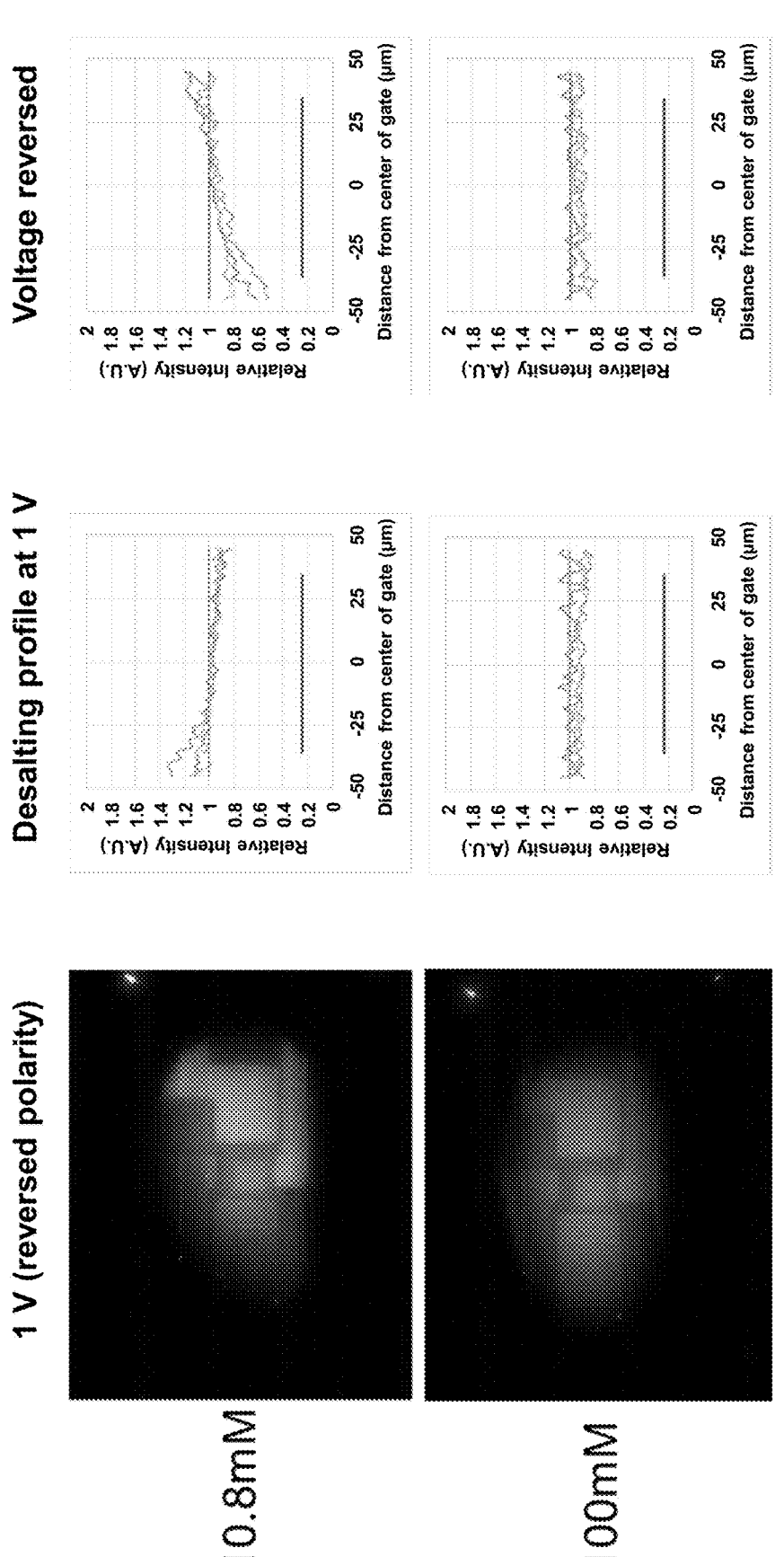
FIG. 13 shows a diagonal desalting profile on gate—repeats for three different ionic strength samples (1.17 mM top; 2.08 mM second row; 10.8 mM third row; 100 mM bottom row).
Figure 14:
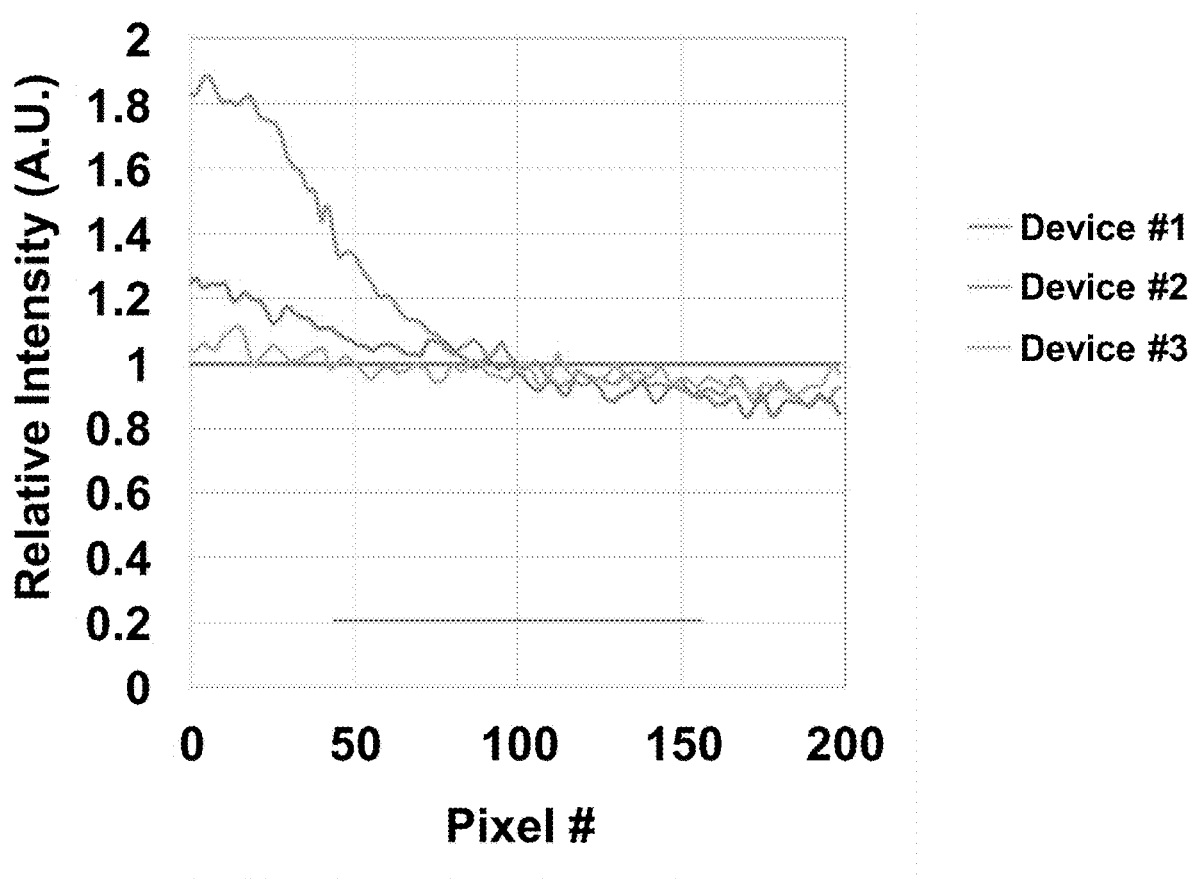
FIG. 14 shows desalting repeatability for 1.17 mM samples.
Figure 15:
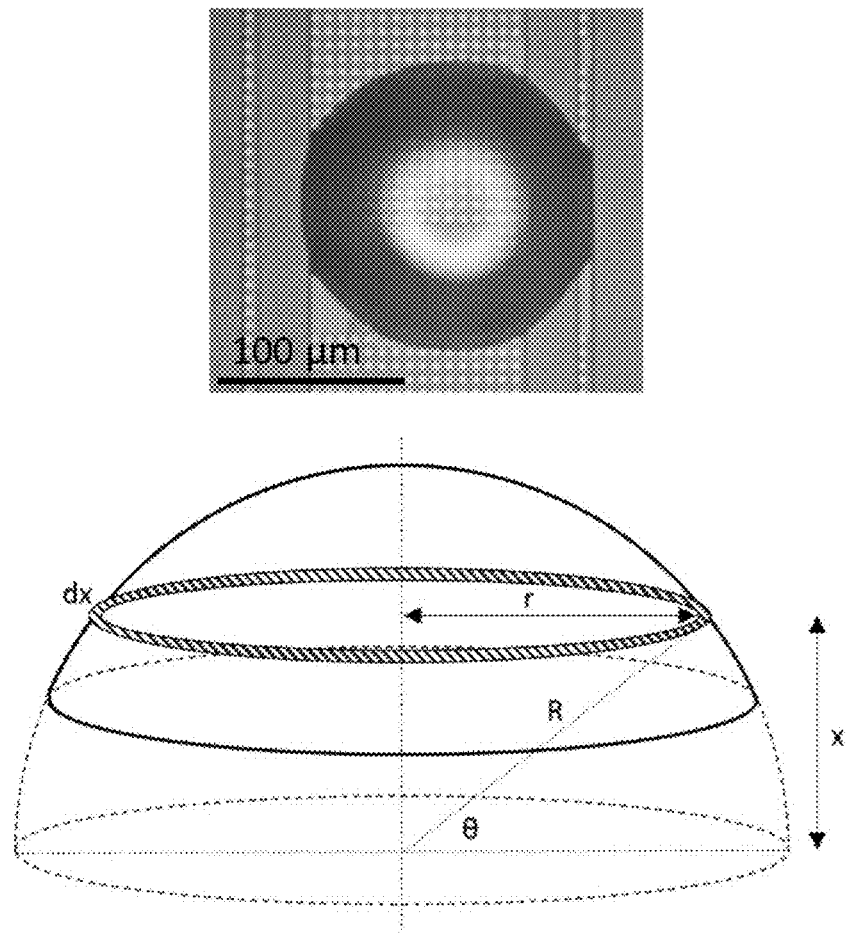
FIG. 15 is a schematic illustration of variables used to estimate the volume and charge in a droplet.

Referring to FIG. 5, dyes are attached to aminosilanized surface using EDC-NHS leaving group chemistry. Ester hydrolysis to carboxylic acid preserves fluorophores for MQAE dye. FIG. 3B shows a microspotted droplet that covers a substantial portion of the FET and both metal electrode pairs. The droplet may be stabilized, such as with 13.5% glycerol. Various ionic strengths are tested (e.g., 0.1-100 mM). A goniometer measures approximate droplet curvature and estimates droplet volume. FIG. 6 illustrates a two electrode (top panel) and four electrode (bottom panel) configuration.

FIGS. 7-9 are experimental results for the two electrode configuration. FIGS. 10-15 are experimental results for the four electrode configuration. Referring to FIG. 8, intensity is normalized to the initial intensity at the start of each experiment. Increase in fluorescence is observed for the electrode where $Na^+$ migrates. Decrease in fluorescence is observed for the electrode where $Cl^-$ migrates. Referring to FIG. 9, ionic current decay between metal electrodes follows desalting trend in accordance with the dye visualization. Data is noisy near the 1E-10 limit (e.g., $V_{desalting} \leq 500$ mV). Higher current in the reverse polarity test suggests residual backfill or backdiffusion after the forward test.

Figure 16:
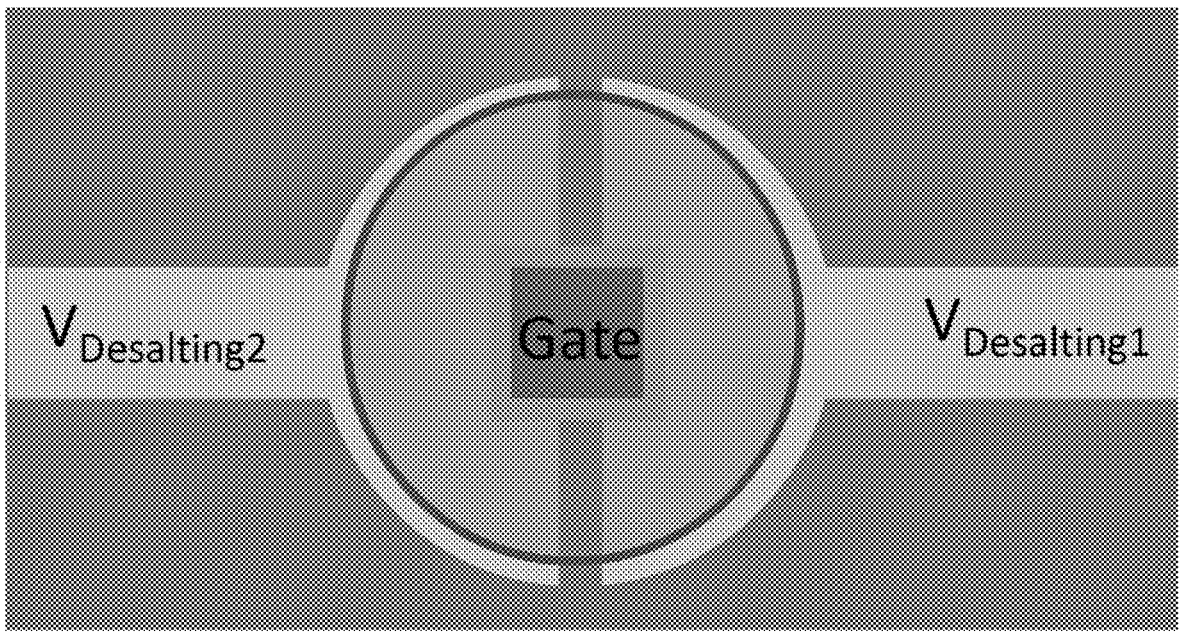
FIG. 16 illustrates a split ring electrode around a gate and sensor of a FET.

FIG. 16 illustrates droplet measurements and schematic used to determine total charge in a droplet. The top panel is a micrograph of a droplet. Droplet characteristics are measured with a goniometer/microscope with the following results: [mead radius=87.30 μm; SD=1.43 μm; N=5 droplets]; [mean contact angle=47.63°; SD=5.59°; N=6 droplets]. As necessary, two or more droplets may be used to ensure coverage of the entire device. The middle panel summarizes variables used to determine fluid droplet, by summing slices of the hemisphere of thickness dx over the droplet height. The volume is calculated as:

$$V = \frac{\pi R^3}{3}(2 - 3\sin\theta_0 + \sin^3\theta_0)$$

where $\theta_0 = \pi/2 - \varphi$, where $\varphi$ is the equilibrium contact angle.

Based on the experimental measurements, an individual droplet is estimated to have a volume of 198.14 pL. The total charge in a 400 pL droplet is summarized in the bottom panel of FIG. 16.

This example characterize multiple metal electrode gate for desalting around FET. The dye experiments confirm counterion adsorption over metal electrodes. Enhanced ion adsorption is observed with both pairs of metal electrodes-gate region shows depletion and partitioning. The predominant desalting effect observed at less than 10 mM ionic strength in microspotted droplet suggests use of even smaller droplet volumes.

Example 3

Paired Electrodes Around Gate

Figure 17:
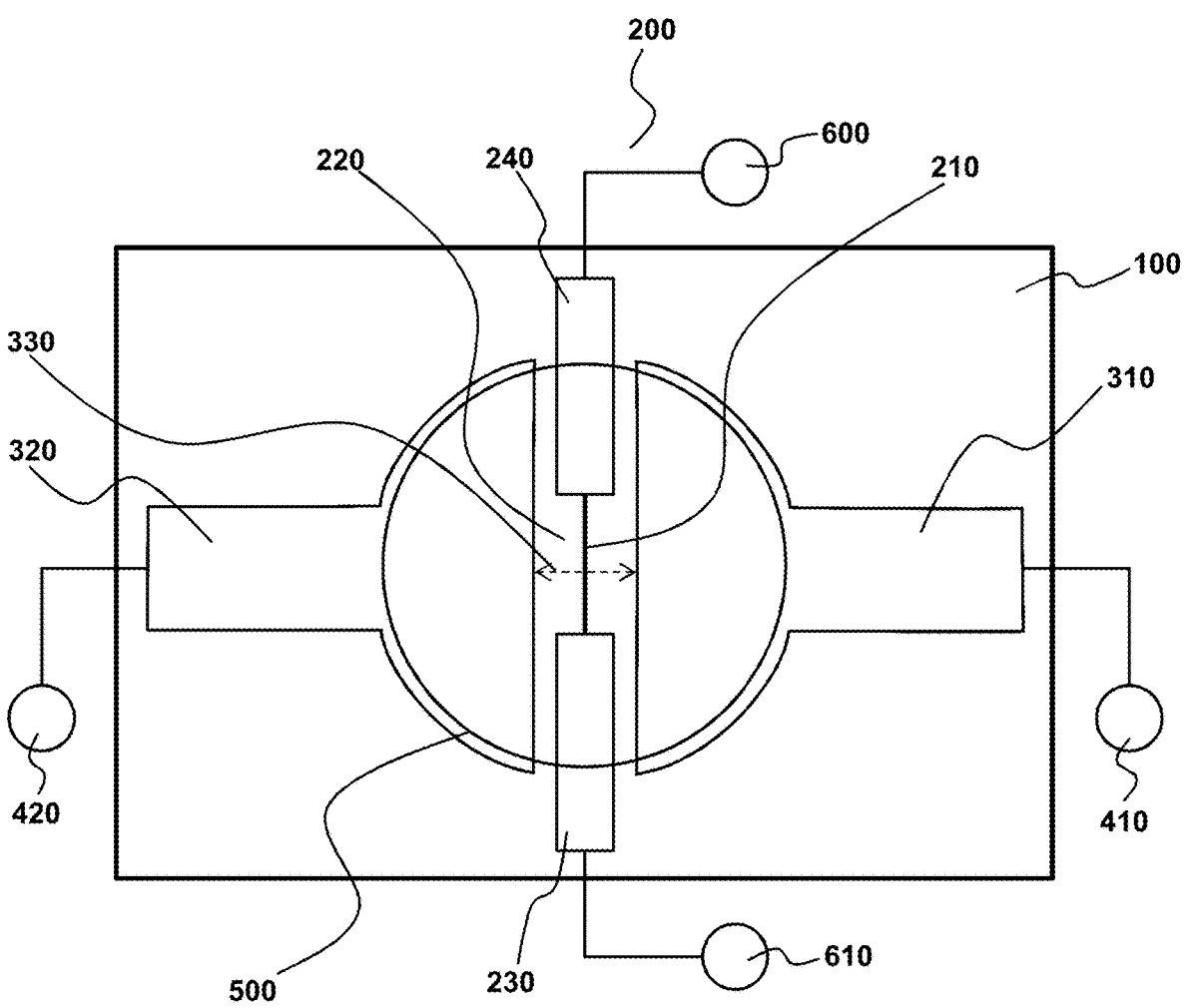
FIG. 17 is a schematic illustration of a split ring ("substantially circular") electrode and FET disposed therebetween.
Figure 18:
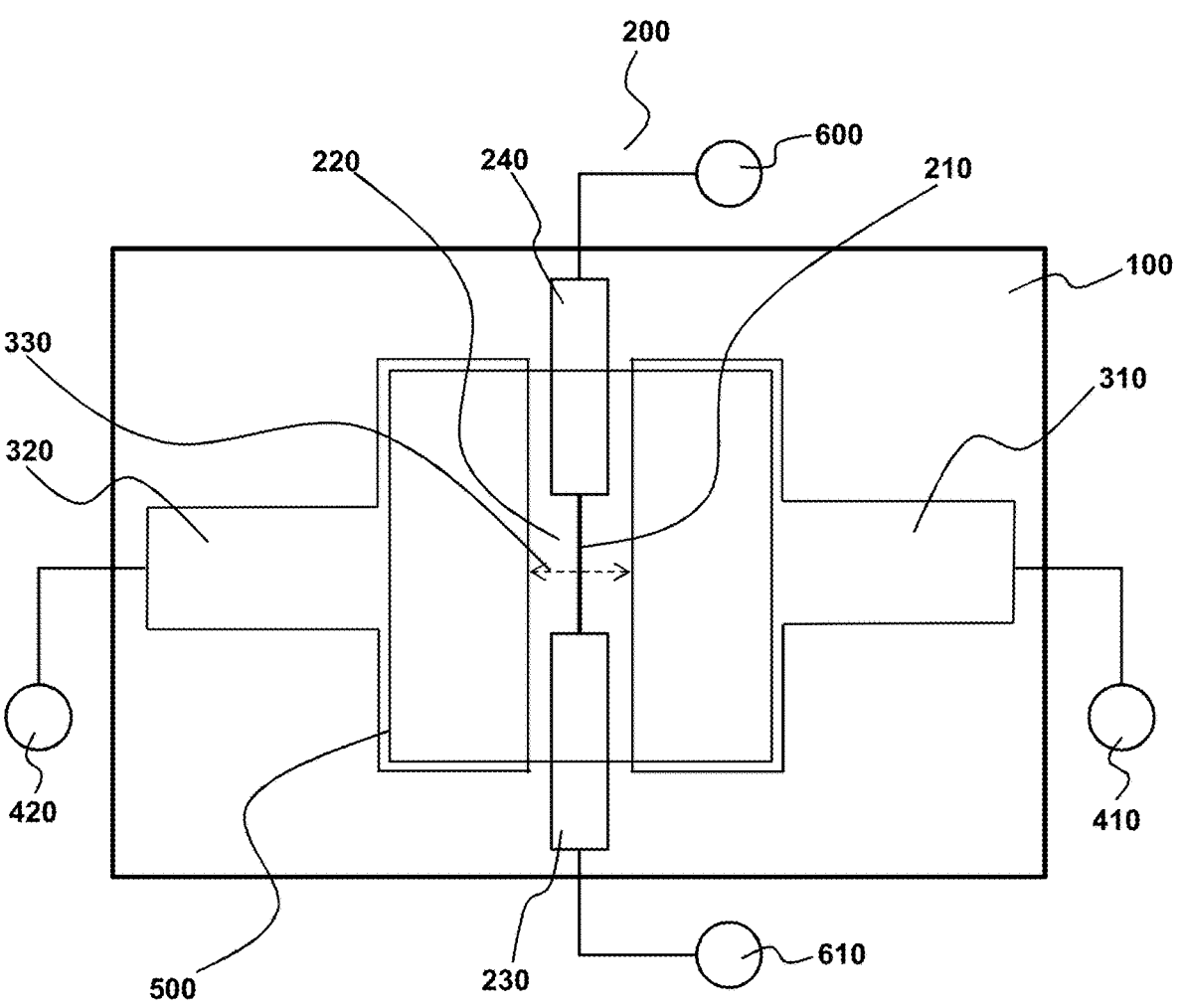
FIG. 18 is a schematic illustration of a pair of non-circular electrodes in a suitable well with a FET disposed therebetween.

FIGS. 17-18 illustrate an increase in metal electrode surface area by more than a factor of 2 to capture more ions. Furthermore, this configuration helps anchor the droplet by wetting of the metal surface around the FET sensor gate. FIGS. 17-18 show a substrate 100, such as a chip, supporting a FET 200, including FET sensor 210, source 230, drain 240, and patterned reference electrodes 310 and 320. Sensor 210 is illustrated as a nanowire with corresponding senor area 220. Reference electrodes 310 and 320 are paired and opposibly face each other separated by a separation distance 330. Electrical controllers 410 and 420 are electrically connected to reference electrodes. Fluid sample is positioned within a well 500 so as to substantially cover the working surface area of reference electrodes 310 and 320 (e.g., the semi-circular shaped portion). Electrical sensor 600 and/or 610 are connected to the FET to monitor an electrical parameter, wherein a change in the electrical parameter indicates presence of an analyte in the sensing region 220.

Figure 19:
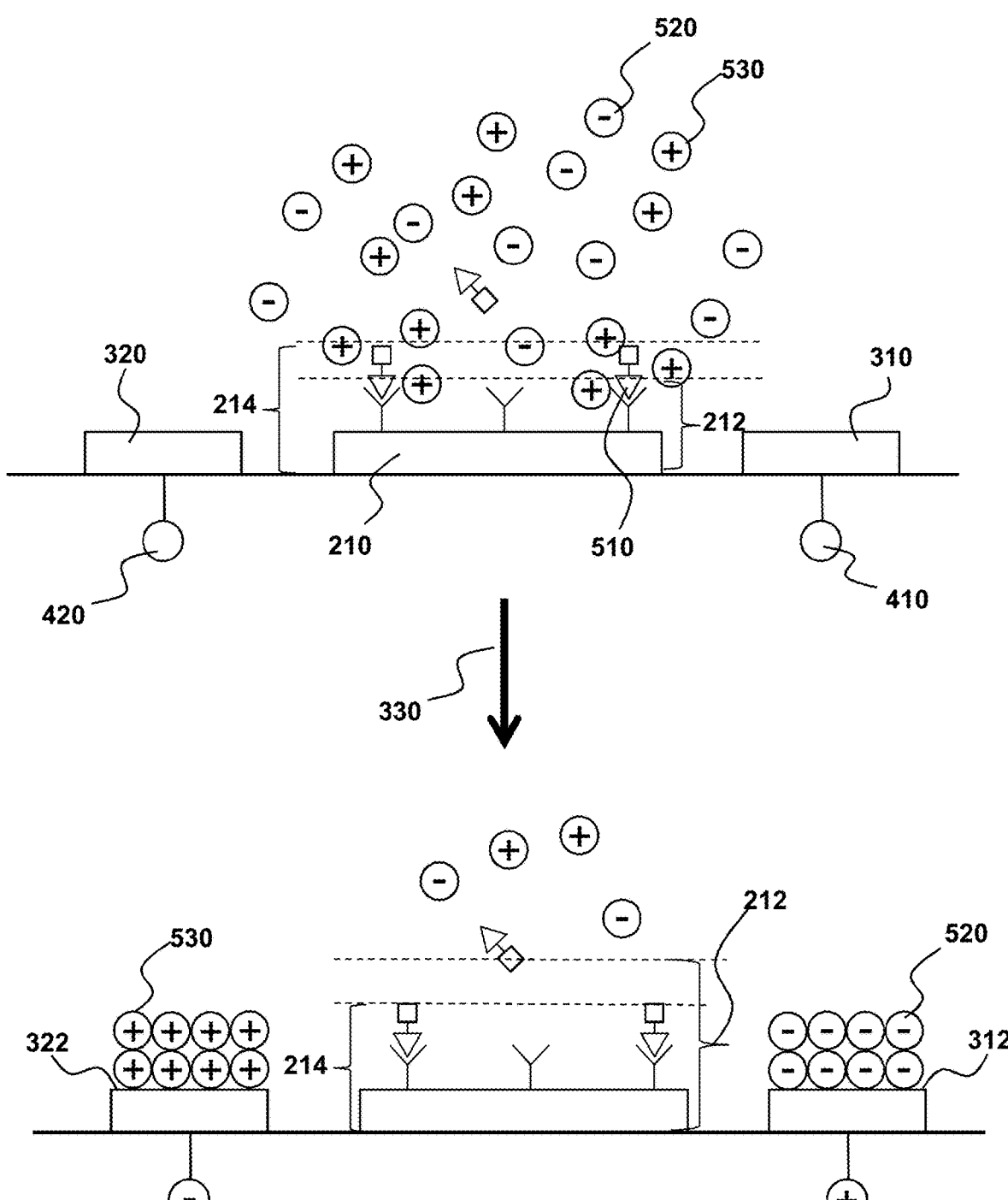
FIG. 19 is a schematic illustration of desalting by reference electrodes and sensing of analyte with a FET sensor. In the top panel, the electrodes are not charged. In the bottom channel one electrode is positively charged and the other paired electrode is negatively charged, thereby removing free charge from the solution and increasing the Debye length.

FIG. 19 is a highly schematized representation of one embodiment of the invention. FET sensor 210 and paired reference electrodes 310 and 320 are shown on a support surface 101 of a substrate. The sample comprises charged ions 520 (negative) 530 (positive) along with analyte 510. The sensor 210 has a sensor surface that is functionalized to facilitate interaction (e.g. specific binding) with analyte 510.

Due to the high ionic strength of the sample, the Debye screening length 212 is indicated as less than the sensor area length 214, with excess charged ions (indicated as positive ions that interact with a negatively charged analyte) screening the electrical effects caused by the presence of bound analyte (see top panel). The instant invention, however, addresses this problem by energizing 330 of reference electrodes 310 and 320 with a desalting voltage by electrical controllers 410 and 420 with the illustrated polarity (see bottom panel). Accordingly, positive ions 530 are attracted to the surface 322 of the one reference electrode and negative ions 520 are attracted to the surface 312 of the other reference electrode. This effectively increases the Debye screening length 212, such as to a length greater than the sensor area length 214, thereby improving device sensitivity with respect to FET detection of analyte in the senor region.

Example 4

High Surface Area Electrodes

To further improve device sensitivity, high surface area electrodes are provided to further improve the desalting effect. In particular, methods for patterning high-surface-area electrodes with nanostructured morphology for improved desalting capacity are provided. Methods may include: (1) Platinum black (Pt-black) that is typically patterned via electrodeposition techniques to convert a seed layer of smooth gold or to platinize smooth platinum [1], [2]. (2) Silver dendritic nanowires that are readily deposited through electroless etching over crystalline silicon substrates and device layers [3], [4]. This may further be converted in a second step to high surface area platinum nanotubes [5]. High surface area carbon black or porous carbon electrodes that find use in many capacitive desalination applications [6].

FIGS. 20-39 summarize various methods of making high surface area electrodes (HAS) for use with any of the methods or devices provided herein. Electrodeposition details are provided, including with respect to deposition uniformity, delamination and bridging. SEM and AFM analysis of rough versus smooth electrodes provide further insight. EIS is used to measure surface area/activity. Desalting experiments using HAS electrodes show ionic current increases with electrode roughening and further characterizes FET biasing and $I_d$-$V_g$ behavior. The desalting and biasing of FET with HAS electrodes informs scaling of surface area and EDL capacitance.

Figure 20:
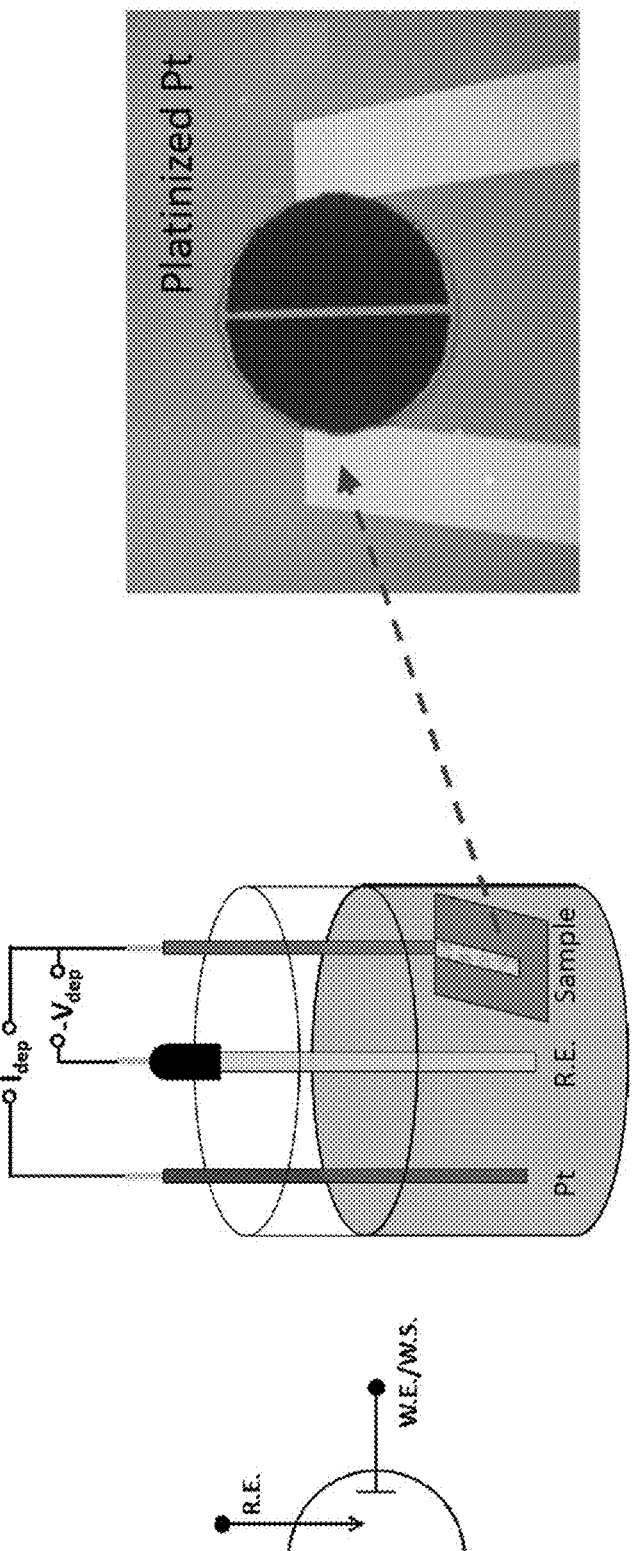
FIG. 20. Increase in active working electrode surface area via electrodeposition.
Figure 21:
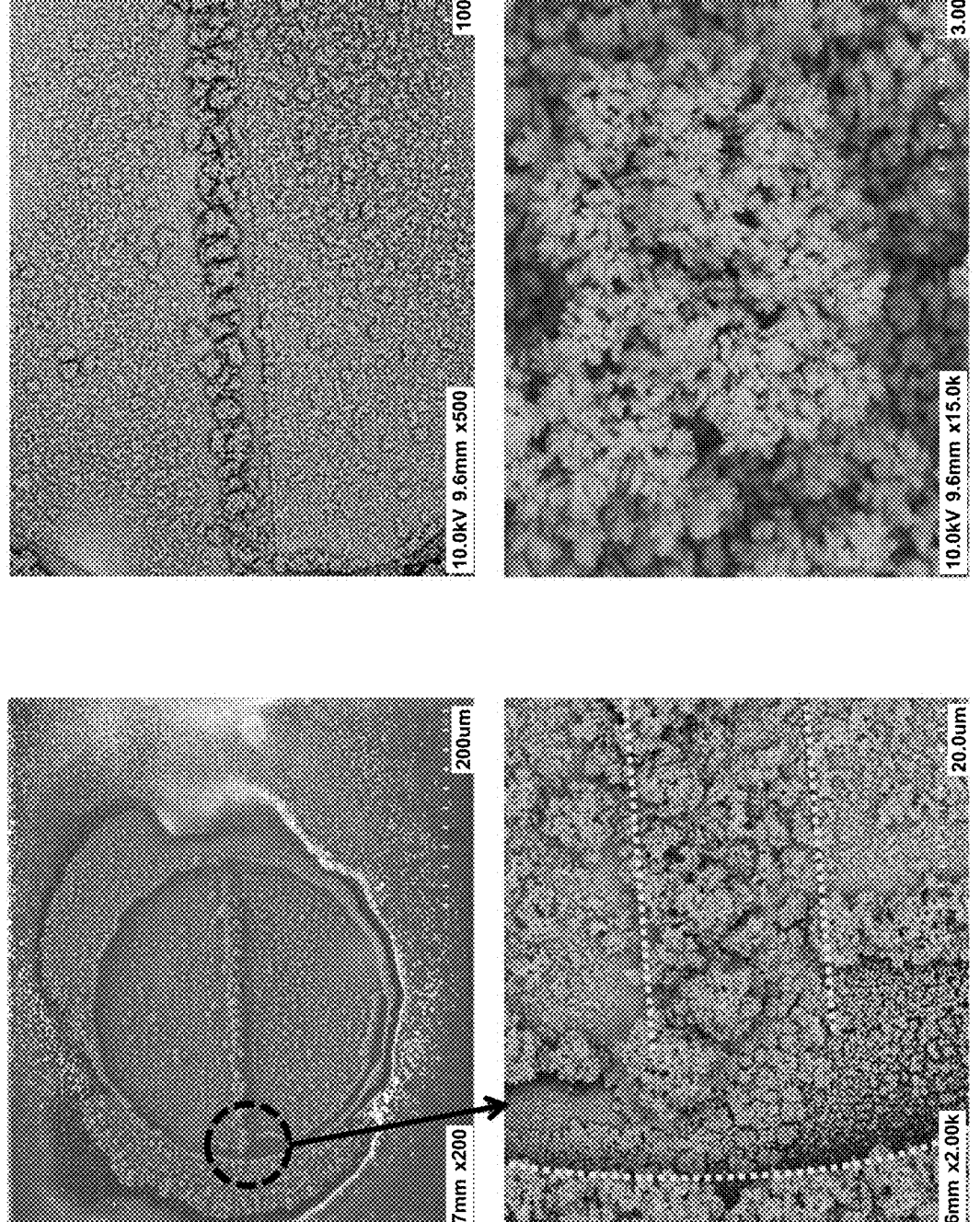
FIG. 21. At "typical" high deposition current density excessive coverage and bridging is observed via SEM.
Figure 23:
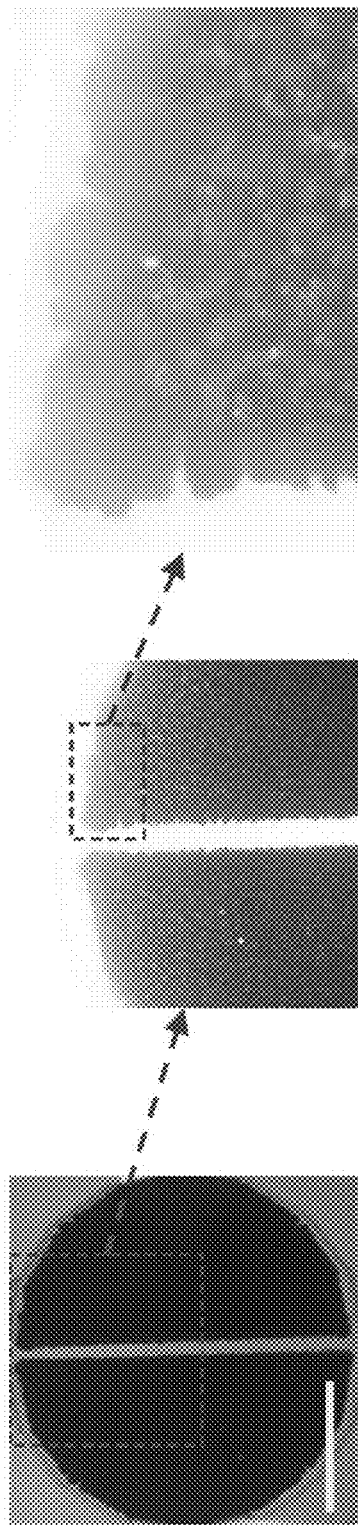
FIG. 23. Surface coverage and morphology for simultaneous electrode plating. Scale bar is 100 µm.
Figure 24:
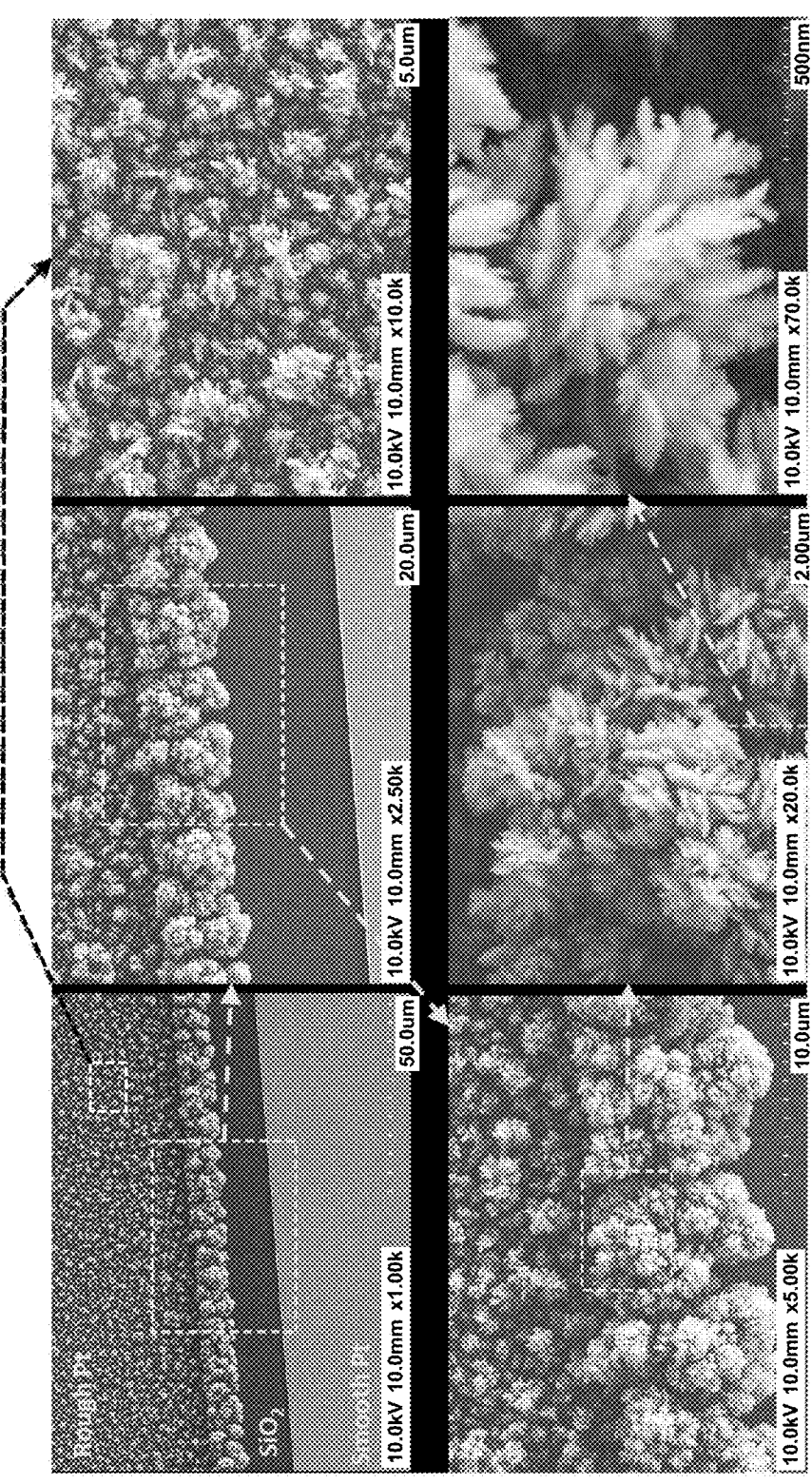
FIG. 24. SEM Images of electrode surfaces. Lower left panel shows a highly branched dendritic morphology that leads to very high surface area, and lower right panel at high magnification (70,000×) shows <50 nm nanoscale structural topology in the features.
Figure 25:
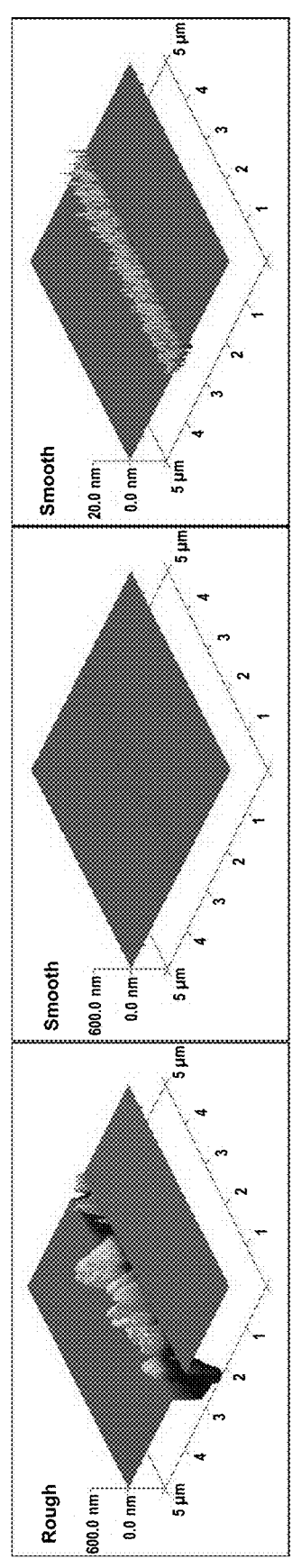
FIG. 25. AFM Roughness Analysis of electrode surfaces.

Available HSA forming methods include Pt black via electrodeposition (Jayshree et al.), Pt black from Ag dendrite (Zhang et al.) and nanotextured Ni from sulfamate/bromide (Ebrahimi et al. Lab Chip, 2013, 13:4248). FIG. 20 illustrates convention 3-electrode cell: Gamry Reference 600 Potentiostat, with an electrolyte (Chloroplatinic acid ($H_2PtCl_6$ $6H_2O$); working electrode (cathode 100 nm Ti/Pt seed layer); reference electrode (Ag/AgCl (leak-fee)); counter electrode (pure Pt wire, preferably galvanostitic condition). Attempts to deposit Pt-black under either galvano/potentiostatic conditions illustrate nonuniformity, delamination, excessive coverage and bridging issues (see, e.g., FIG. 21). FIGS. 22-23 illustrate that decreasing deposition current provides better control, with a trade-off between control of coverage, morphology and area. FIG. 22A-22C illustrates current density of $I = I_o/5$; dep. time, $t = t_o$; about 5× less Pt deposited.

Due to the small amount of material deposited, it is not feasible to weigh deposited material. Accordingly, SEM and AFM is used to obtain data on shape, morphology, surface roughness and area projection. Desalting experiments showing ionic current transience illustrates initial scaling and then decay to similar steady-state values. Impedance change due to area/topology show enhancement with rough electrodes compared to corresponding smooth electrodes.

Figure 26:
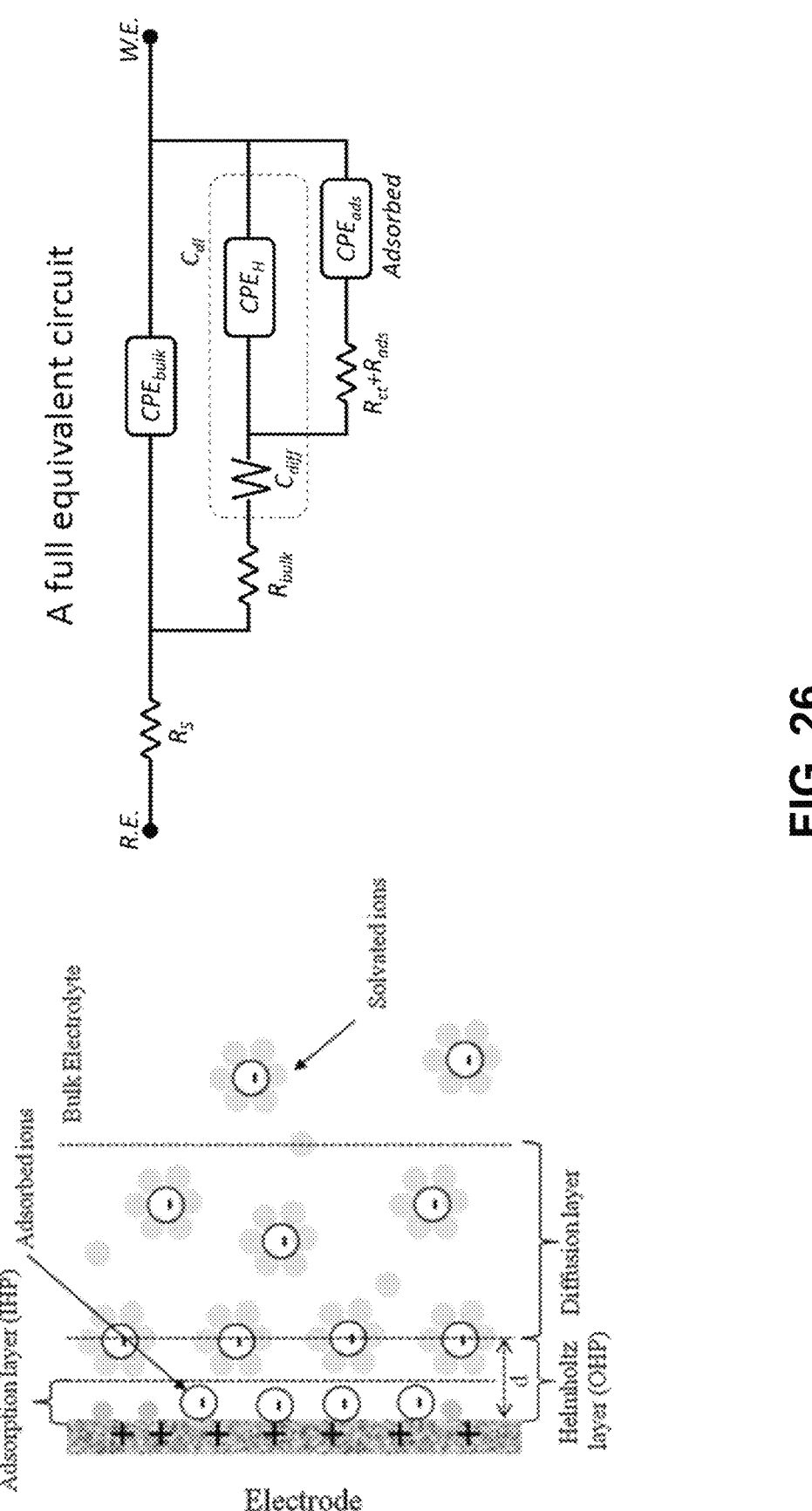
FIG. 26. Surface Analysis of electrodes via EIS.

FIG. 26 illustrates the study of electrical response of surface across frequency spectrum using very small AC perturbations. This model is used to characterize electrochemical activity, thin films and electrodes. See, e.g., Kang et al. Eletrochim Acta, 2014 115:587; Heer et al, Biosens Bioelectron., 2004, 20:358.

Figure 27A:
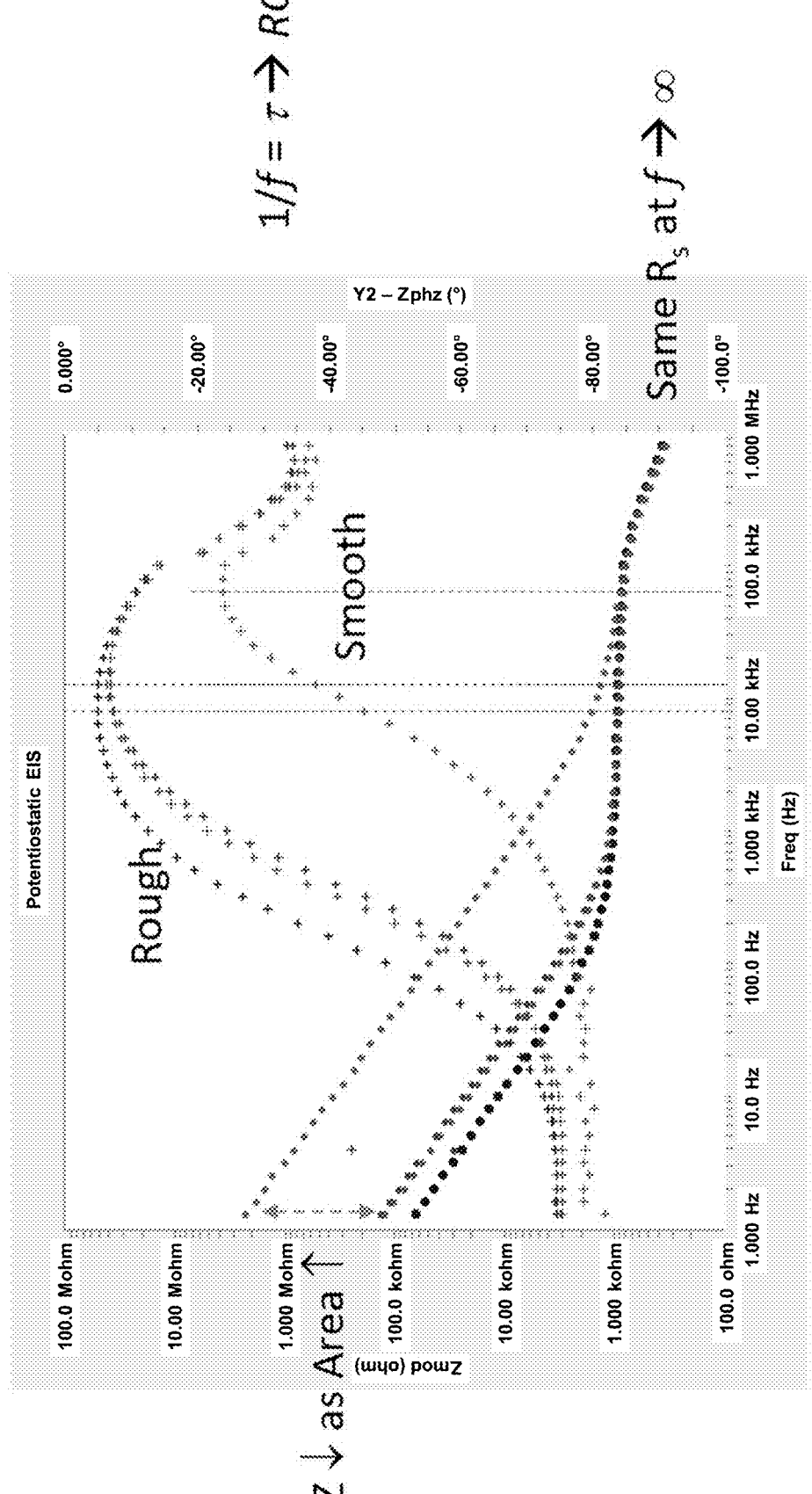
FIG. 27A. Bode plot of the EIS analysis outlined in FIG. 26. Improvements to area enhancement of Pt-black electrodes through cyclic voltammetry treatment.
Figure 27B:
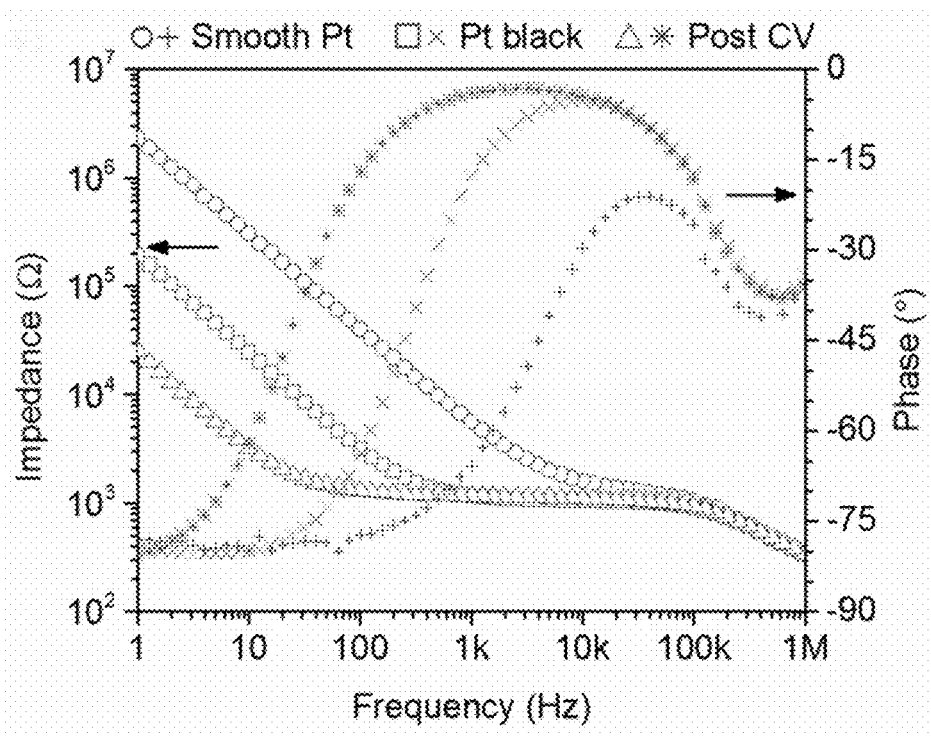
FIG. 27B. Bode plot of EIS in 1×PBS showing changes from smooth to Pt-black (as deposited) to post-CV treatment.
Figure 27C:
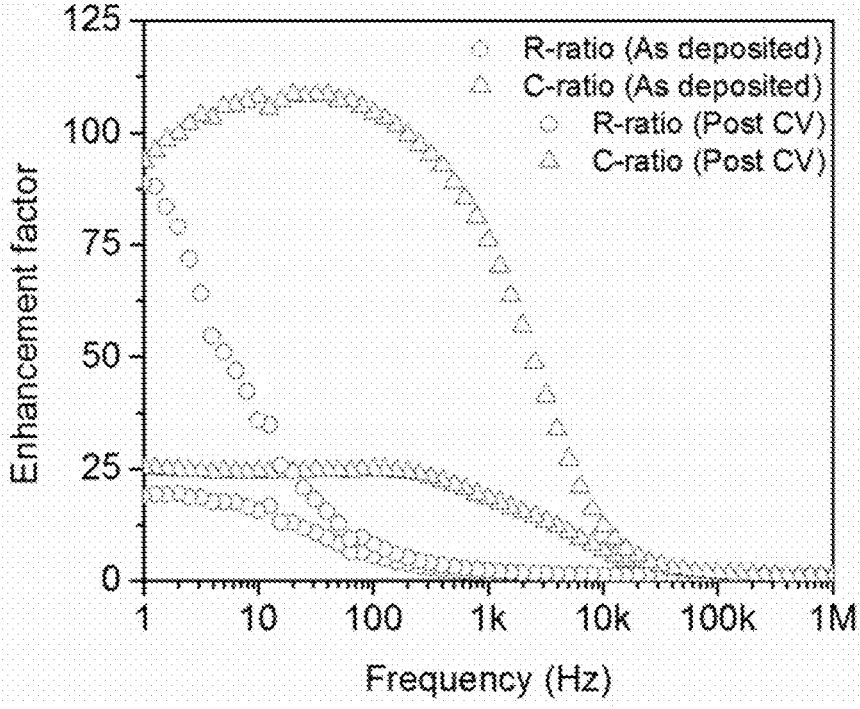
FIG. 27C. Average effective area enhancement (both resistance or capacitance scaling over smooth electrode) shows a further 4-5 fold increase from as deposited to post-CV treated Pt-black electrodes.
Figure 28:
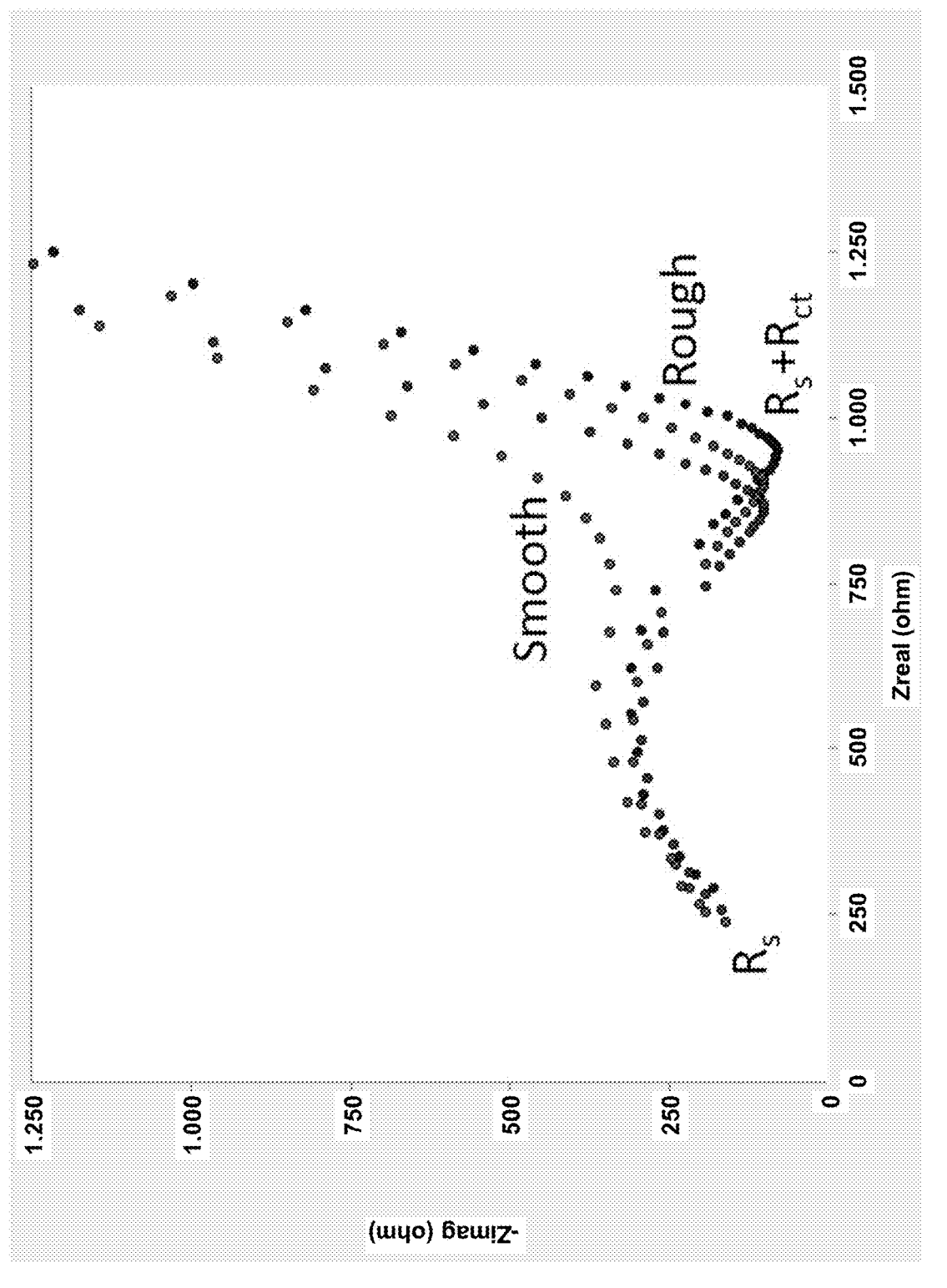
FIG. 28. Nyquist plot of the EIS analysis outlined in FIG. 26.
Figure 29:
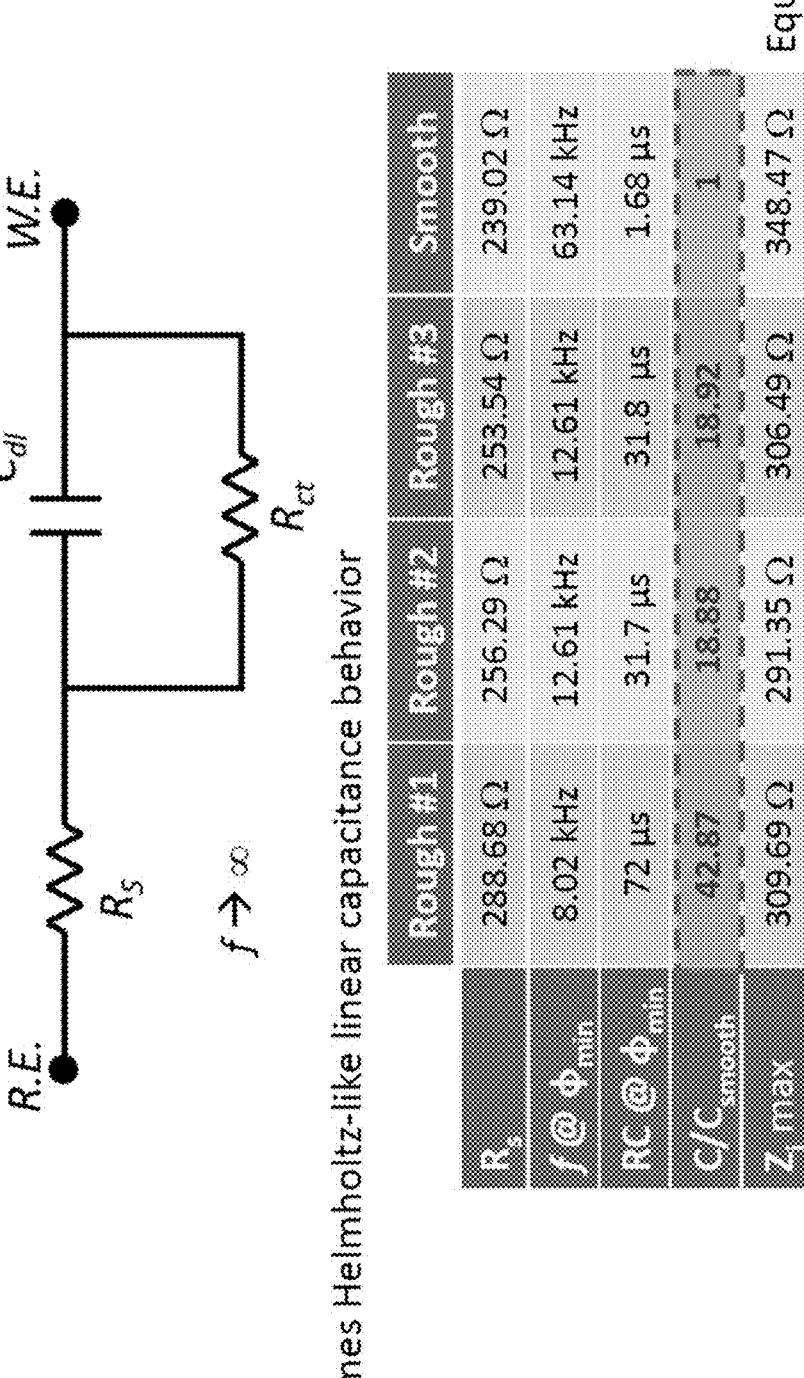
FIG. 29. Randles Equivalent Circuit Analysis, assuming Helmholtz-like linear capacitance behavior.
Figure 30:
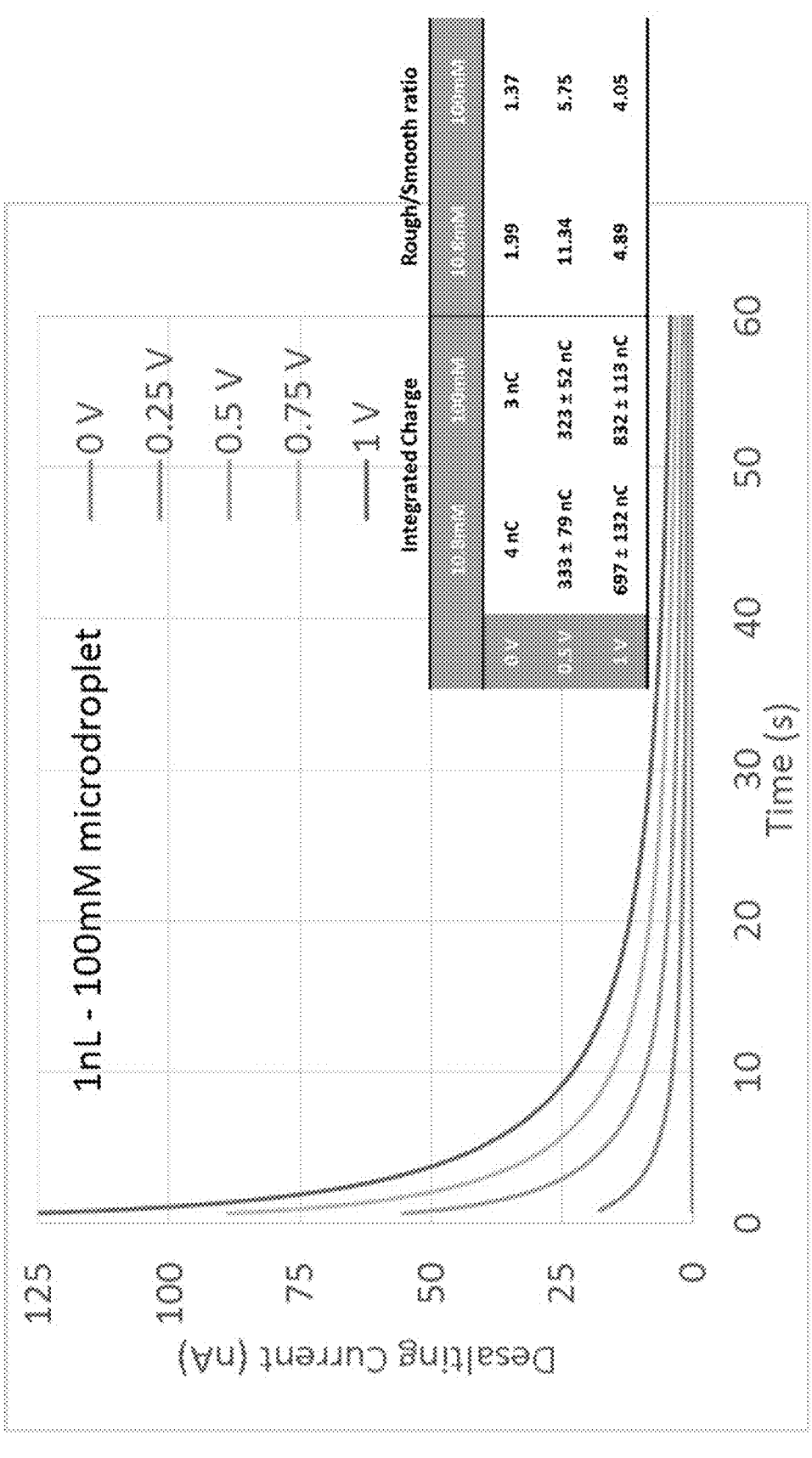
FIG. 30. Desalting with high surface area (HAS) electrodes.
Figure 31:
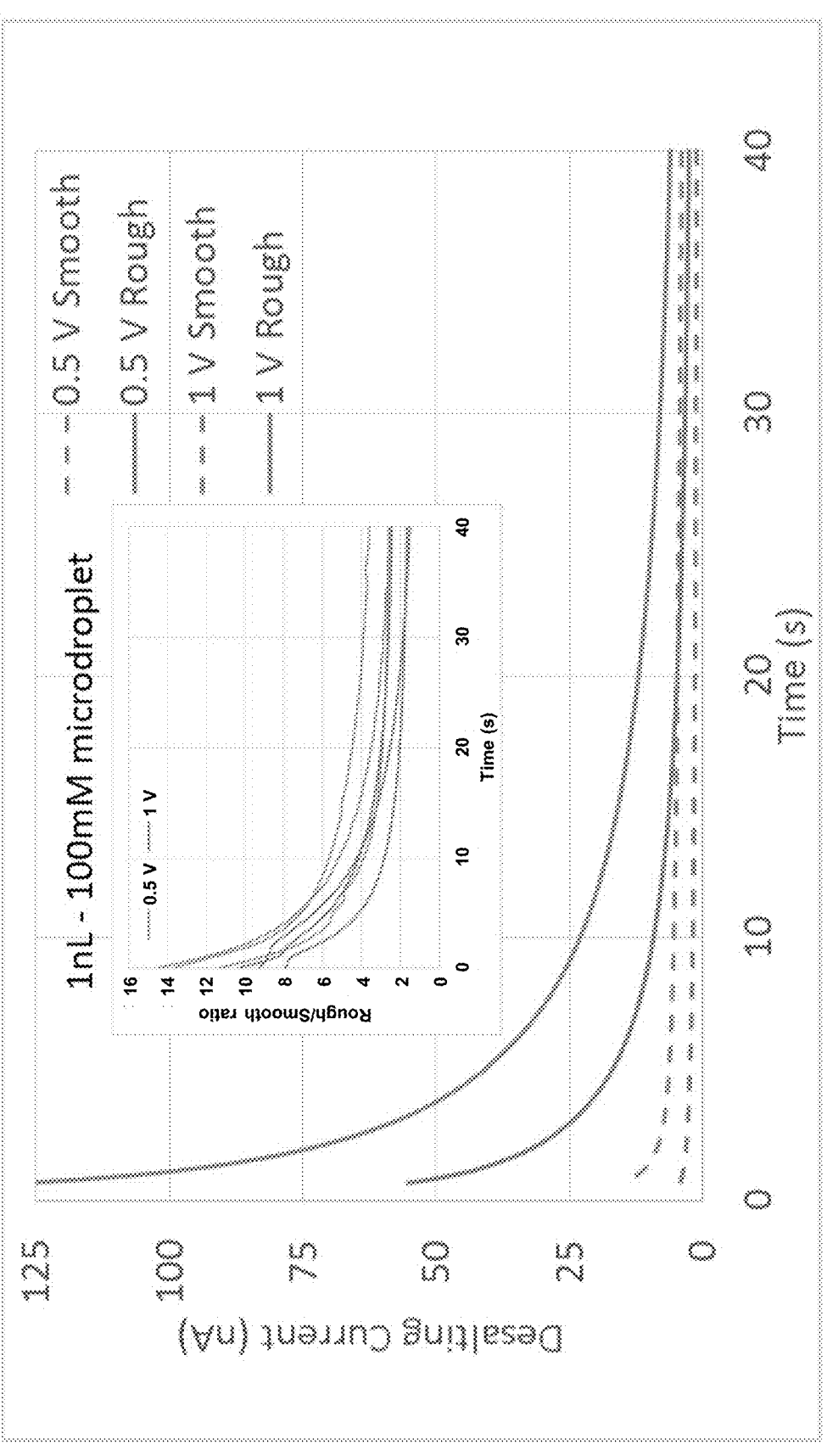
FIG. 31. Desalting: Rough vs. Smooth electrode for 0.5V and 1V conditions The inset is a plot of the ratio of Rough/Smooth.
Figure 32:
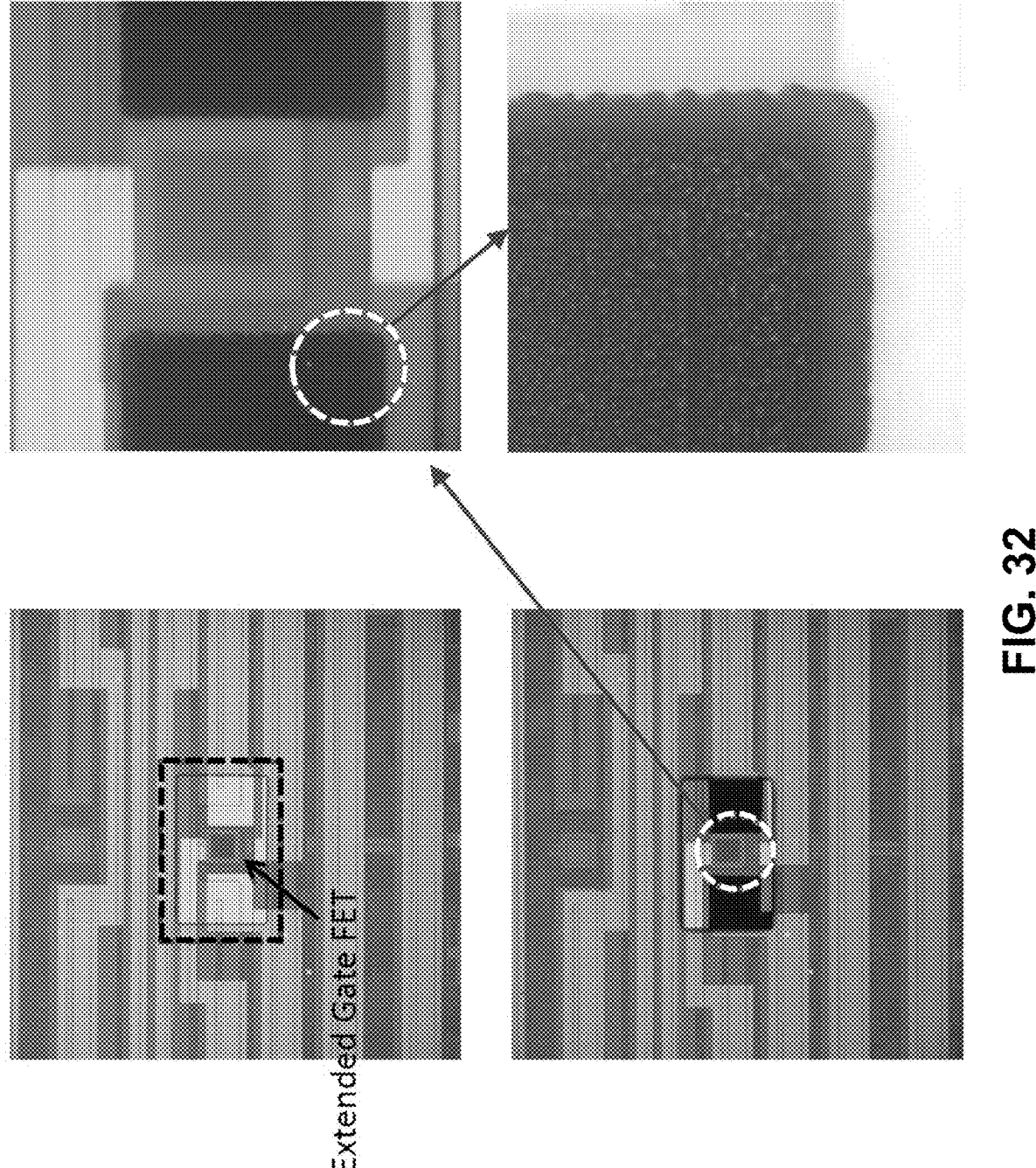
FIG. 32. Surface electrode roughening around FET devices.
Figure 33:
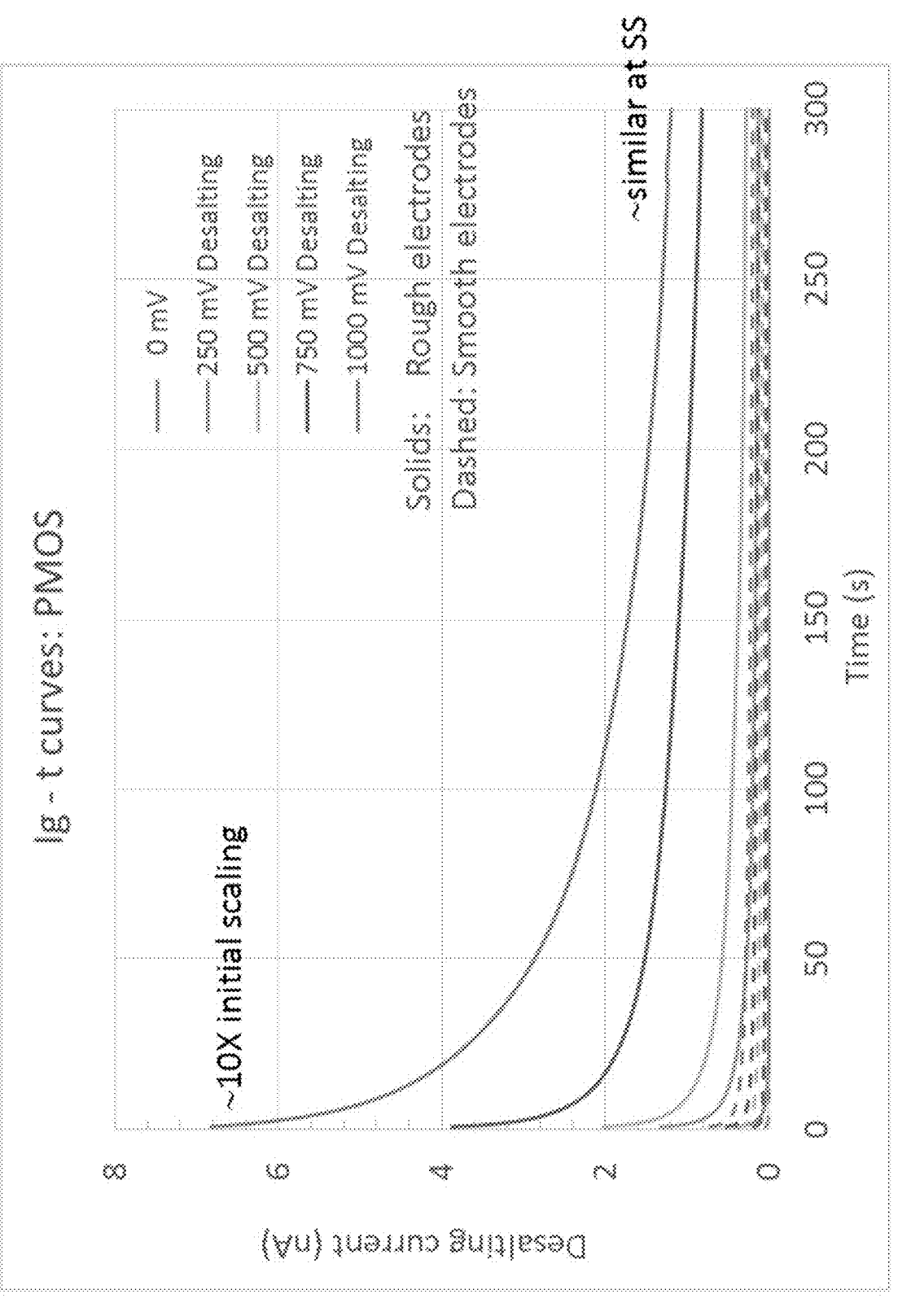
FIG. 33. Desalting around FET: Rough vs. Smooth for 1.174 mM microdoplet (0.5 nL volume) with the same device/electrode measurements.
Figure 34:
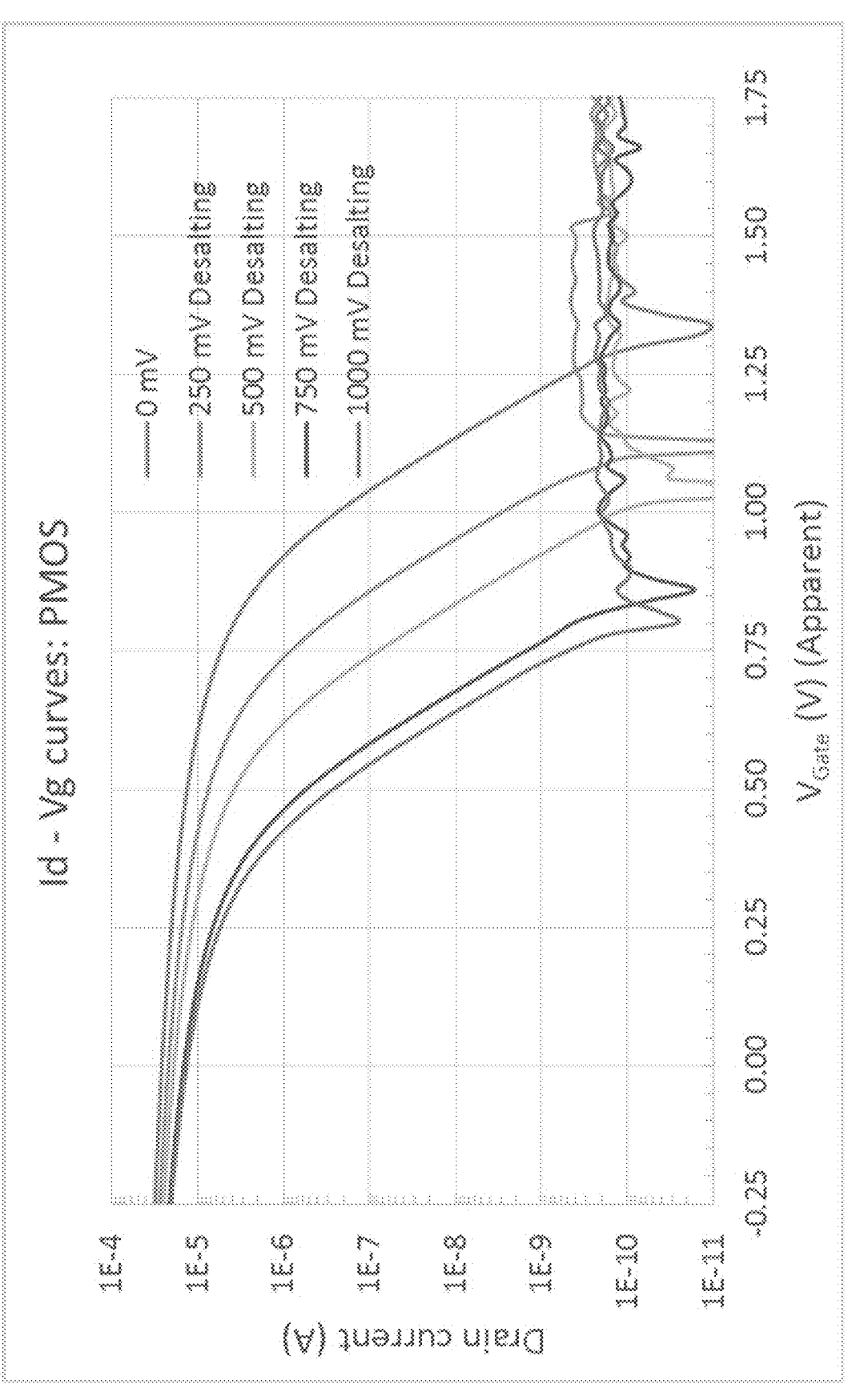
FIG. 34. Operating the FET during desalting with Rough electrode (1.174 mM microdoplet) for different voltages.
Figure 35:
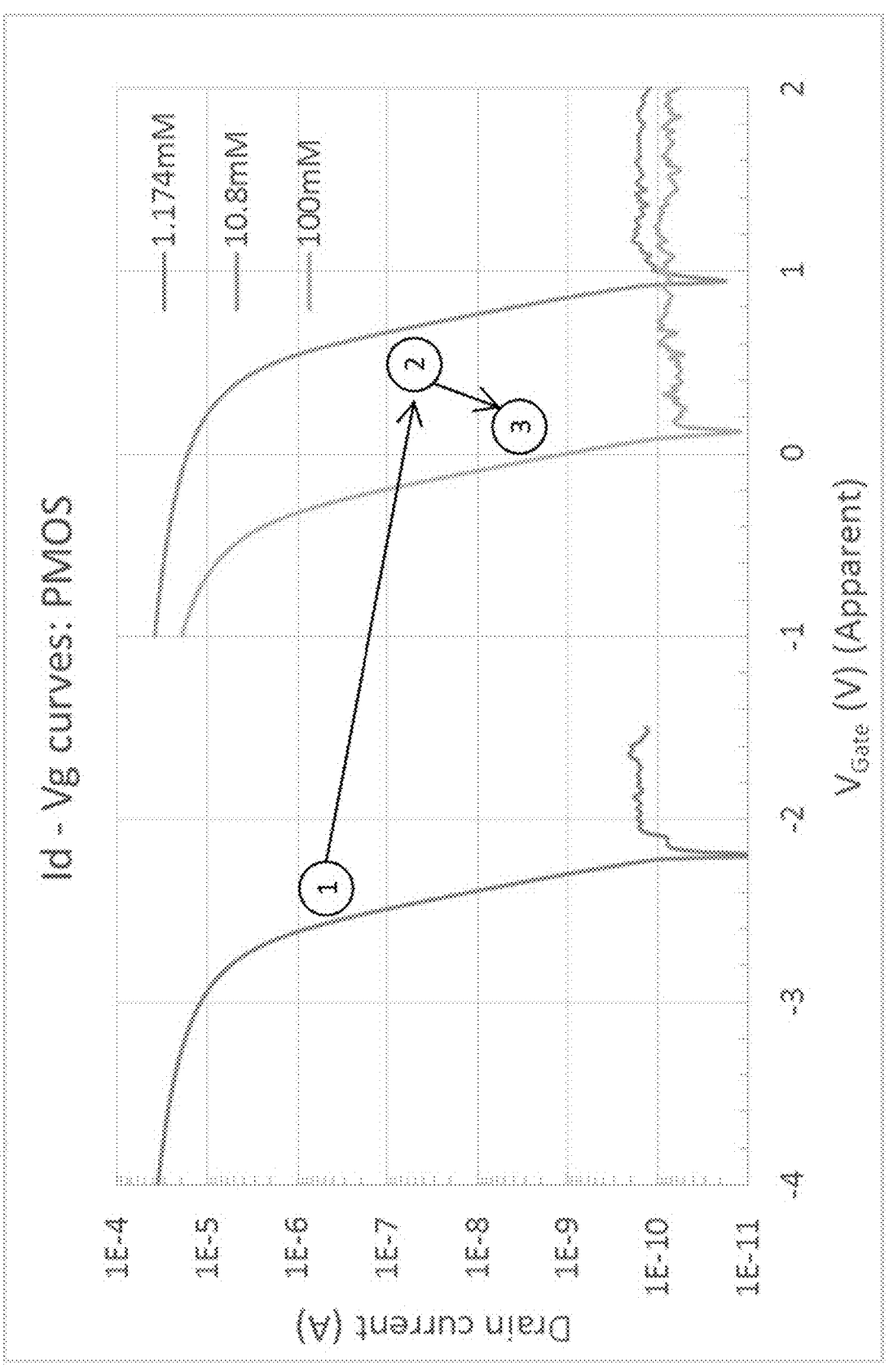
FIG. 35. Operating the FET during desalting with Rough electrode. Across salts $V_{Desalting}$=1 V for various ionic strength solutions.
Figure 36:
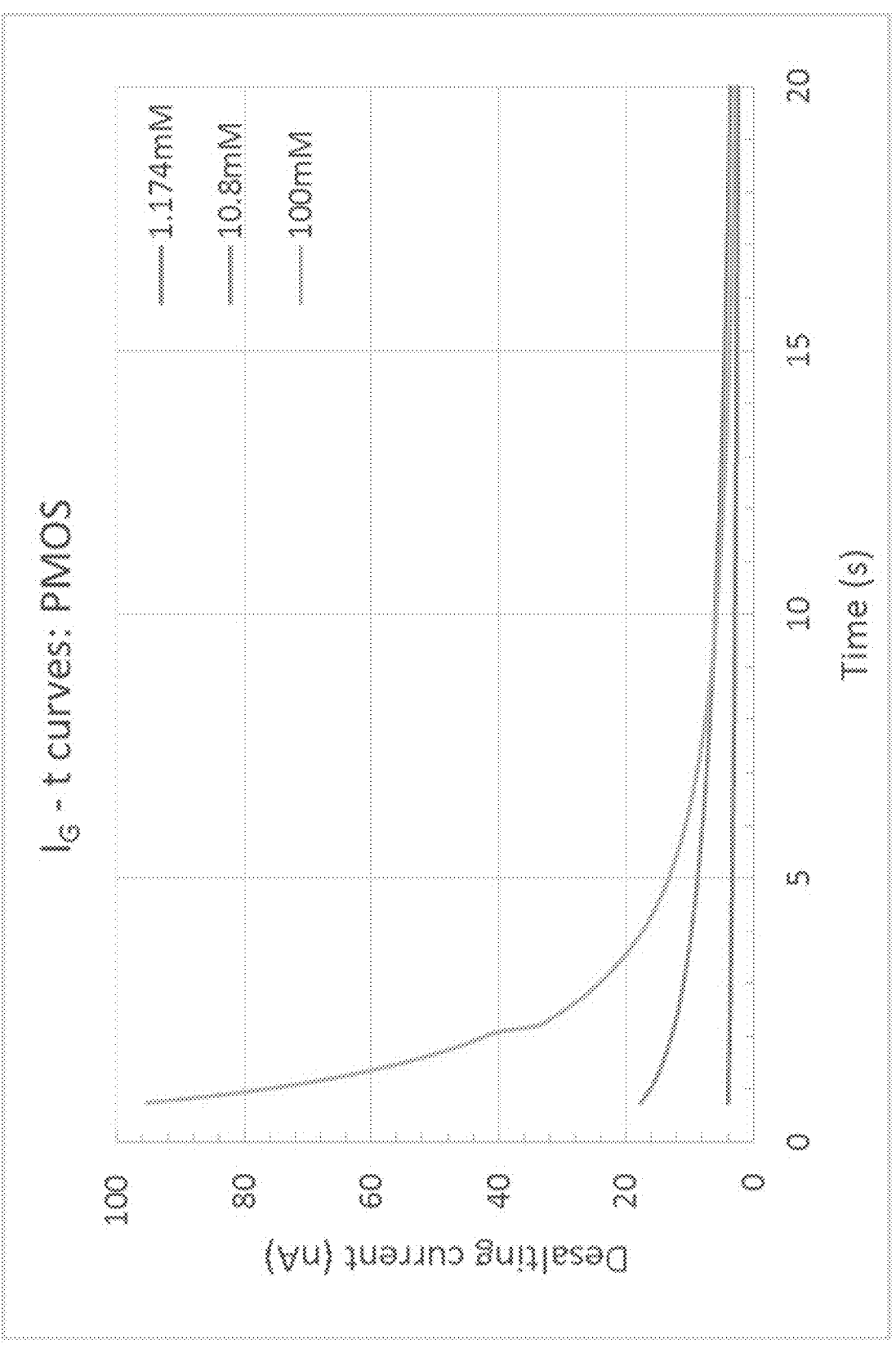
FIG. 36. Operating the FET during desalting with Rough electrode. Across salts $V_{Desalting}$=1 V for various ionic strength solutions.
Figure 38:
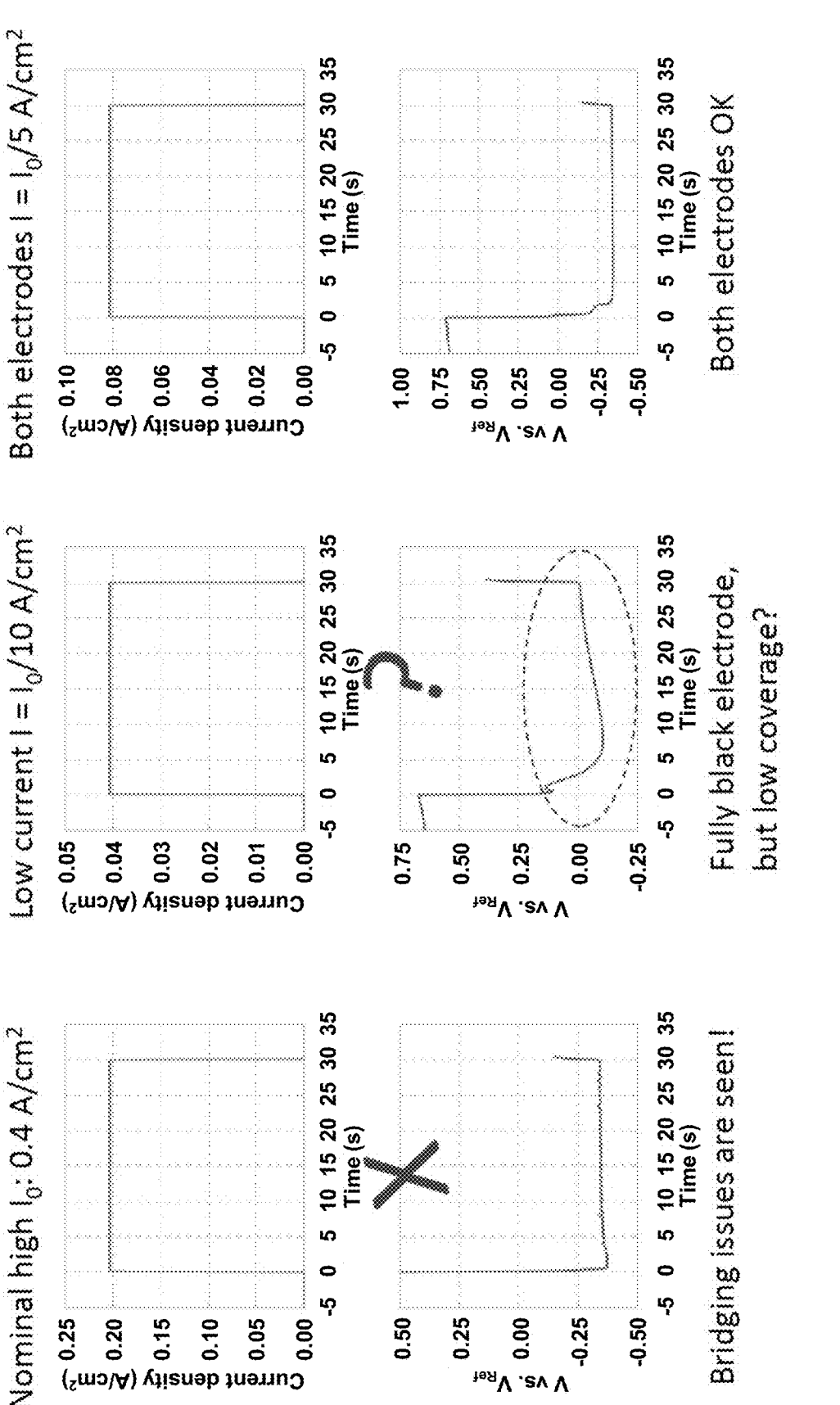
FIG. 38. Deposition conditions for black Pt.
Figure 39:
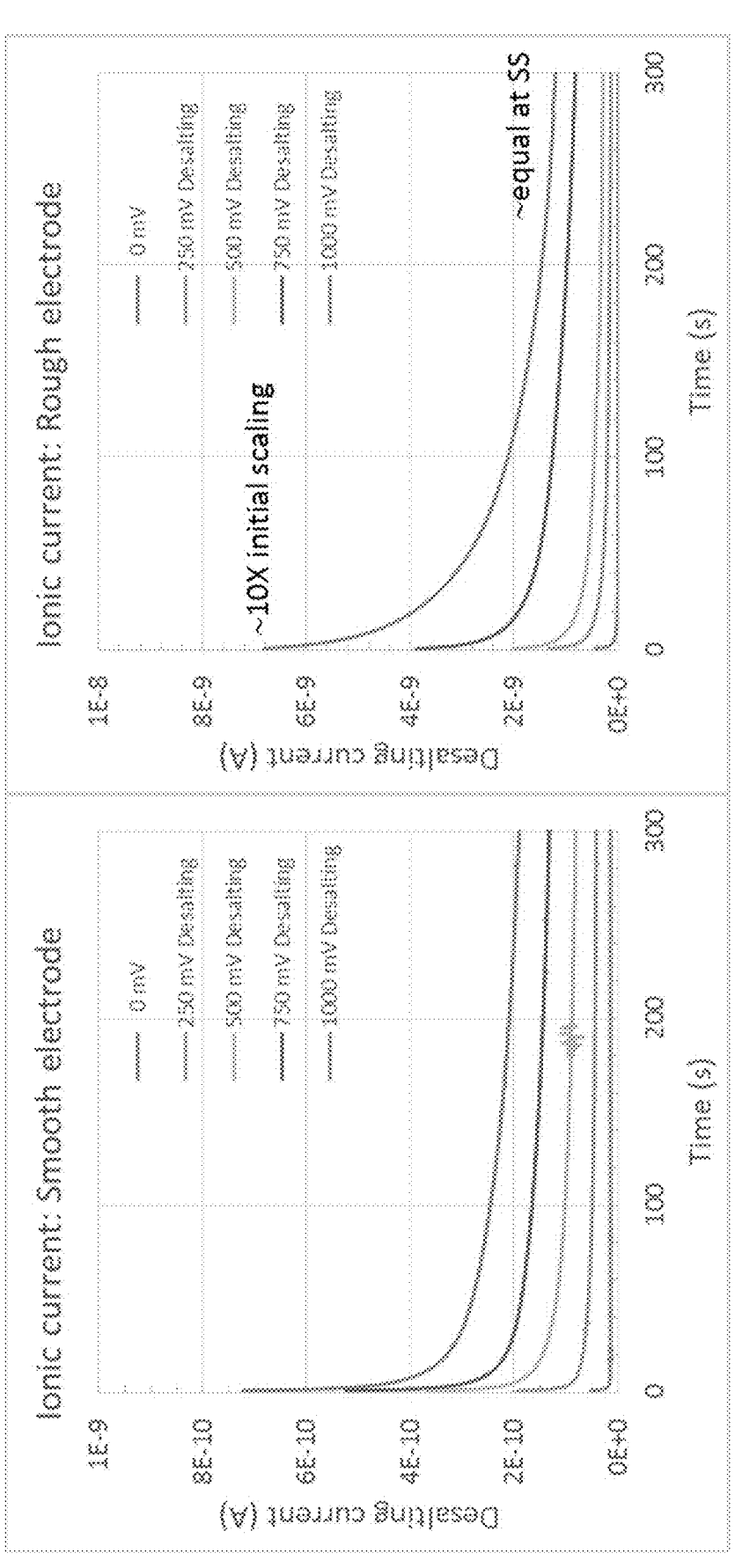
FIG. 39. Desalting around FET: Rough vs. Smooth reference electrodes for 1.174 mM microdroplet (0.5 nL) of same device/electrode dimensions.

FIG. 27 is a Bode plot showing spread of impedance magnitude (chair) and phase angle across the frequency spectrum. A phase peak shift corresponds to smooth to rough capacitance change. FIG. 28 is a Nyquist plot that assists in isolation of the real (resistive) and imaginary (capacitive) elements in the circuit. Similar $Z_r$ minima (solution) and $Z_i$ maxima (EDL blocking) are observed.

FIG. 37 illustrates that physical surface area enhancement may not translate into absorption. For highly branched morphology (3D fractal), inhomogeneities are likely. For nanostructure hydrophobicity, partial wetting is expected. Furthermore, exclusion effects may become relevant as I approaches $\lambda_D$. For length-scales less than 50 nm for dendritic nanostructures in the rough electrode, there may be embedded interstices in the network that ions cannot approach. Ion saturation at tips may also occur as steady state is approached.

The HAS process is optimized and is made compatible with FET/device dimensions for use with the invention provided herein. Extremely dendritic 3D nanostructures are fabricated, of less than 50 nm features. Increased ionic current uptake due to area enhancement is observed. A large initial increase (10-15×) is observed that tends to tape, but not completely (2-4×). Early transients at t much less than 1 sec may be much greater. Integrated charge scales up to at least 5-10×. Inhomogeneity due to exclusions/reduced wetting can explain disparity between physical area increase versus actual absorption. EIS characterization shows a greater than 17-fold increase in EDL activity. FET biasing is also possible with rough electrodes, with similar $V_G$ shifts as observed for smooth electrodes. Further improvement, such as increased capacity, is expected from smaller droplet, wider electrodes, and more Pt black. Early transients at much less than 1 second time period suggest potentiostat can be useful. Nanowire or thin BSS molecular sensing may be integrated with the desalting.

Figure 44:
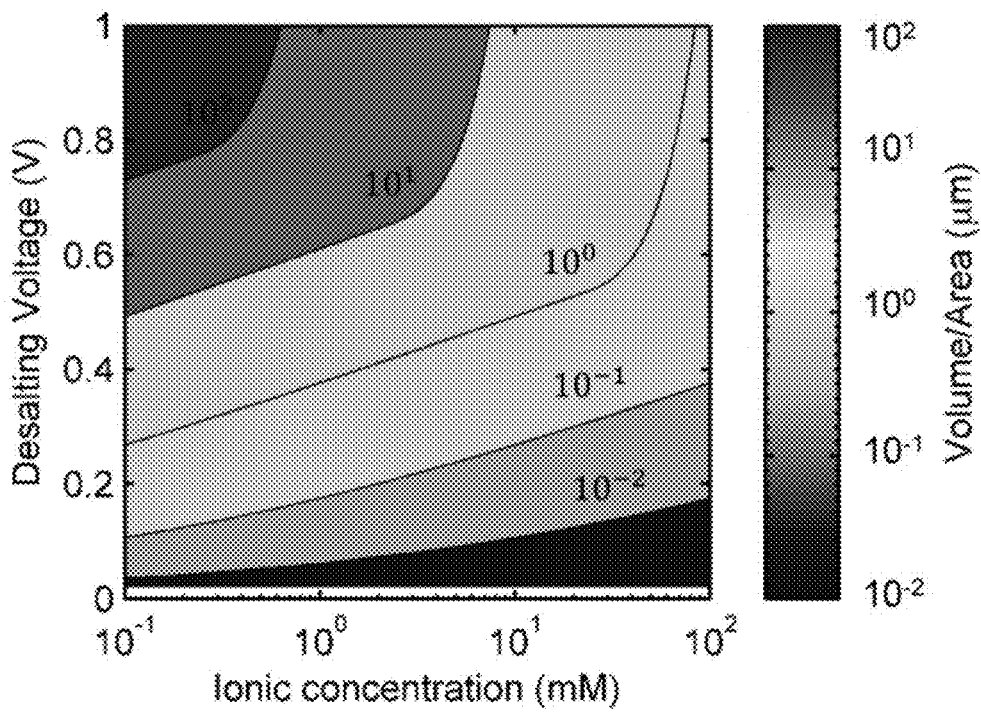
FIG. 44. Ratio of the volume of droplet to the area of the electrode required for desalting the droplet by 50%, as a function of desalting voltage and ionic concentration. Desalting at 100 mM concentration under 1 V desalting bias requires an aspect ratio of ~1 µm.
Figure 45:
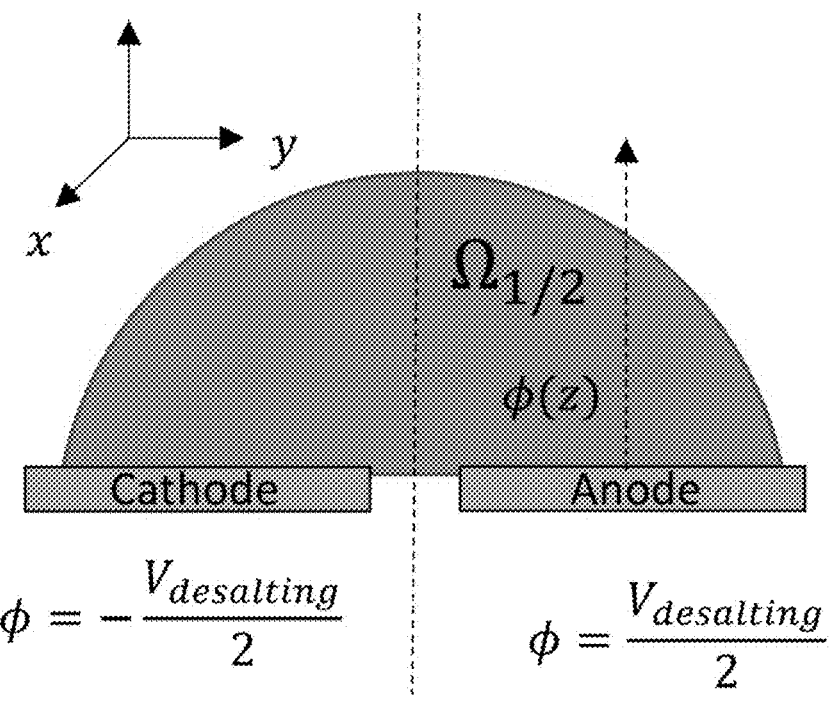
FIG. 45. Schematic illustration of the analytical model.

By depositing 500 pL droplets on 100 μm×100 μm electrodes, we demonstrate desalting from concentrations of up to 10 mM. However, in order to achieve substantial desalting for physiologically relevant concentrations (≥100 mM), the volume of droplet to electrode area must be substantially reduced (<1 μm) as shown in FIG. 44. For example, for a 100 μm×100 μm electrode area, we require ~1 pL droplet volume spread over the entire electrode area to match the desired ratio. This can, in part, be achieved using a superhydrophilic surface[49] over which droplets settle into shallow configurations. However, for desalting of larger, more addressable droplet volumes (≥100 pL) at 100 mM concentration, we use electrodes with significantly higher surface area capable of increased ion absorption.

High surface area electrodes were prepared through electrodeposition of platinum-black from known methods[50,51]. Starting with the seed layer of 1000 Å thick Ti/Pt, Pt-black was galvanostatically deposited from dihydrogen hexachloroplatinate (30 mL of 0.08 mM $H_2PtCl_6.6H_2O$, Sigma Aldrich, with 7.5 mg of $(CH_3COO)_2Pb$, Alfa Aesar) in a conventional 3-electrode setup at a high current density of −0.08 $A/cm^2$ vs. Ag/AgCl. FIG. 22 shows micrographs of Pt-black deposited on both (b) test electrodes in a circular well (250 μm diameter) and (C) on-chip electrodes in a rectangular well (250 μm×100 μm) around a FET. SEM image of these electrodes (FIG. 24) confirms a highly branched, dendritic morphology and, at high magnification (FIG. 24), the critical dimension in the nanostructure is of the order of ≤50 nm, which should provide the necessary area enhancement for desalting from high salt conditions.

Surface area enhancement due to nanostructured rough electrodes over smooth Pt was examined by two methods— a) electrochemical impedance spectroscopy (EIS)[52-54], a known technique for surface analysis of electrodes, as well as b) by comparing their desalting capacities. FIG. 54A shows a Bode plot of the impedance of circular test electrodes in bulk 1×PBS. At high frequencies (≥100 kHz), regardless of the electrode surface, impedance was dominated by bulk solution characteristics. However, interfacial characteristics became apparent in the low frequency response as we approach DC-like conditions. The effect of increased surface area from smooth Pt to Pt-black is reflected in the large decrease in impedance magnitude at 1 Hz, or in the left-shifting of the phase minima to lower frequency because of the increase in EDL capacitance. FIG. 54B shows a plot of apparent area enhancement due to Pt-black versus frequency by comparing the ratio of capacitances (imaginary component) or inverse ratio of resistances (real component). Although the dendritic nanostructure is expected to produce at least 2 orders of magnitude increase in surface area, we observed that the electrically available increment was ca. 25-fold.

The desalting capacity increase was also measured by ionic current on both circular electrodes (FIG. 54C) and on-chip electrodes around the FET (FIG. 54D), in 10.8 mM 500 pL microdroplets, at various desalting voltages. During the experiment of FIG. 54D, the FET is also simultaneously turned on with Pt-black electrodes. In both experiments, the ionic current scaled by an order of magnitude from smooth Pt to Pt-black. The inset of FIG. 54C shows the ratio of ionic current over time, while the inset of FIG. 54D also shows the same desalting current traces when using smooth Pt electrodes around the FET. We saw an effective increase of ~10-fold in charge uptake while desalting in sub-nanoliter droplets.

References for Example 4

[1] R. S. Jayashree, J. S. Spendelow, J. Yeom, C. Rastogi, M. A. Shannon, and P. J. A. Kenis, "Characterization and application of electrodeposited Pt, Pt/Pd, and Pd catalyst structures for direct formic acid micro fuel cells," Electrochimica Acta, vol. 50, no. 24, pp. 4674-4682, August 2005.

[2] L. Zhu, N. Kroodsma, J. Yeom, J. L. Haan, M. A. Shannon, and D. D. Meng, "An on-demand microfluidic hydrogen generator with self-regulated gas generation and self-circulated reactant exchange with a rechargeable reservoir," Microfluid. Nanofluidics, vol. 11, no. 5, pp. 569-578, November 2011.

[3] Z. Huang, N. Geyer, P. Werner, J. de Boor, and U. Gösele, "Metal-Assisted Chemical Etching of Silicon: A Review," Adv. Mater., vol. 23, no. 2, pp. 285-308, January 2011.

[4] W. Ye, C. Shen, J. Tian, C. Wang, L. Bao, and H. Gao, "Self-assembled synthesis of SERS-active silver dendrites and photoluminescence properties of a thin porous silicon layer," Electrochem. Commun., vol. 10, no. 4, pp. 625-629, April 2008.

[5] G. Zhang, S. Sun, M. Cai, Y. Zhang, R. Li, and X. Sun, "Porous Dendritic Platinum Nanotubes with Extremely High Activity and Stability for Oxygen Reduction Reaction," Sci. Rep., vol. 3, March 2013.

[6] T. J. Welgemoed and C. F. Schutte, "Capacitive Deionization Technology™: An alternative desalination solution," Desalination, vol. 183, no. 1-3, pp. 327-340, November 2005.

Example 5

Sample Droplet Volume

To further improve sensitivity, the ratio of droplet volume to electrode area is selected to achieve better desalting capacity. Volumetric considerations and the limited ability to electronically absorb ions over electrodes place constraints on having to deplete salt ions within droplets. While the quantum of ions scales with the volume of the droplet, the desalting effect scales with the surface area of the electrodes. Hence, the ratio of the droplet volume to the available electrode surface determines the extent of desalting and a desirable threshold is approached as the droplet volume is decreased and the electrode area is increased. In order to deplete a droplet by 50% or more of its ions, at 1 V electronic desalting potential, it is necessary that this ratio is of the order of 1 µm or smaller. A 1 nL droplet over 10000 µm² electrodes provides an aspect ratio of 100 µm. Such a desalting system can include a 50 nm wide and 10 µm long nanowire FET biosensor. In order to approach the desired aspect ratio of 1 µm, a combination of one or more of the following three pathways may be employed: (1) Decrease the droplet volume down to the sub-nanoliter and picoliter range, with adequate coverage around the electrodes and FET sensor; (2) Increase the electrically available surface area of the electrode through nanostructured morphology—this provides up to a factor of 100 improvement within the same droplet volume to absorb more ions during the desalting process; and/or (3) Increase the wetting area of the droplet over electrodes via hydrophilic surface treatments that promote spreading of the droplet and allow it to settle in a shallow conformation. This may be accomplished either through hydrophilic surface activation or self-assembled monolayer (SAMs) that decrease the contact angle. This enables designing a larger, shallow well. A fraction of glycerol may also be included to prevent evaporation of flat droplets.

Maximizing the effective area enhancement with surface treatment: While it follows from the microstructure of the Pt-black (FIG. 24) that the physical surface area may be drastically enhanced, our experimentally observed increase in absorption capacity was limited to about an order of magnitude (up to 25-fold). The deficiency from expected increase may be interpreted as due to: either the incomplete coverage of the surface in contact with the droplet because of the increased surface energy cost of nanostructured surfaces that typically renders them repellant, or the exclusion effects from steric issues that may come into play for ion absorption as the physical dimension of the surface (≤50 nm) approaches the phenomenological lengthscale, $\lambda_D$.

However, by suitably conditioning the electrode surface through electrochemical treatment such as cyclic voltammetry (CV)[23,55], we can further improve and stabilize the surface characteristics of the Pt-black for increased ion absorption during desalting. The circular electrodes with Pt-black are subject to 5 cycles between −0.5 V to +0.9 V vs. Ag/AgCl at the rate of 100 mV/s in 1×PBS. FIG. 27 compares the EIS results of CV treated high-surface area electrodes with the as deposited Pt-black as well as smooth Pt. From the Bode plot in FIG. 27B, we observe improvements through further decrease in both the impedance at 1 Hz and the left-shifting of the phase minima to lower frequency. Upon extracting the resistive and capacitive components at all frequencies and scaling the improvement over smooth Pt, the post CV-treated Pt-black electrodes show at least a 4-fold increase over the as deposited Pt-black at low frequency (FIG. 27C). With CV treatment, the Pt-black electrodes demonstrate effective area enhancement factors of ca. 100-fold over smooth Pt that agree with the expected physical area increase of about two-orders-of-magnitude. Maximizing the electrode surface available for desalting is crucial for extending the ion depletion to the 10-100 mM system; with a 100-fold effective surface area enhancement through nanostructured Pt-black and relevant surface conditioning, we can approach the desired droplet volume to electrode area ratio of 1 µm that enables desalting of microdroplets as large as 100 pL to 1 nL around a FET sensor.

Example 6

Physics of Localized Electronic Desalting for Enhanced Sensitivity of FET Biosensors Nanobiosensors that can detect the charge of target biomolecules during binding or hybridization events can facilitate label-free detection schemes with the potential to realize point-of-care (POC) devices. However, the charge of these biomolecules will inevitably be screened by the surrounding ions in any physiological solution, decreasing the charge transduced to the sensor and reducing overall sensor sensitivity. Consequently, most electrical sensing experiments are conducted at very low ionic concentrations. This strategy necessitates complex fluidic exchange/dilution steps and must tolerate sub-optimal binding specificity and kinetics of biological processes in weakly buffered solutions. Sensitivity, selectivity, or both are invariably sacrificed for such systems. To address this fundamental problem, we demonstrate a method for localized electronic desalting on a field effect transistor biosensor by using on-chip polarizable electrodes to locally deplete salt ions around the target analyte molecules of interest. By locally removing these ions, the apparent charge of the target molecules is maximized and the sensitivity of the device can be increased. Sub-nanoliter droplets are used as isolated reaction chambers to prevent back diffusion of ions towards the locally desalted area. We also show that the polarizable microelectrodes can be used to simultaneously establish a stable gate potential for the field effect transistors for electrical sensing experiments during the desalting process itself. This approach could pave the way for multiplexed label free electronic detection in physiological solutions without sacrificing sensitivity.

Nanowire-based FET devices[1] have facilitated label-free electronic detection of a range of small biomolecules, including nucleic acids[2-5], proteins[6,7], viruses[8,9] etc. Silicon nanowire devices have benefited from the scalability of nanofabrication techniques and paved an attractive route towards multiplexed detection with arrays of FETs[6]. While considerable advances in device fabrication have been realized to maximize the sensitivity and robustness of nanowires, including the incorporation of high-K gate dielectrics[10,5] and optimization of device geometry[11,12], little effort has been dedicated towards overcoming the fundamental screening limitations on-chip. On one hand, decades of research on indirect pH-based detection[13,14] has met with success towards marquee applications such as DNA sequencing with the ISFET[15] and led to recent commercial demonstration of genome sequencing using large scale arrays of CMOS FETs[16]; on the other hand, given the inability for direct electrical detection from physiological samples, a commercially viable solution has been elusive for integrating nanowire FETs within portable-scale diagnostics. In order to overcome this major hurdle, it is necessary to directly address the problem of excess salt ions that interfere with sensing. In this example, we report a localized desalting scheme around a FET sensor, within a droplet, using on-chip platinum electrodes that also provide the gate bias. This scheme has many applications of commercial importance, including for label free sensing under physiological conditions. Results are further interpreted by comprehensive numerical simulation of ionic charge profile within the droplet for a range of salt concentration and applied biases.

The background excess of ions in aqueous media greatly complicates the detection of charged species due to heavy shielding of electrode-electrolyte interfaces as well as the target molecules by the electrostatic double layer (EDL)[17-19]. The relevant phenomenological lengthscale is the distance it takes for an electric field induced by a charged molecule to decay down to 1/e of its original value, also known as the Debye screening length[20,21], $\lambda_D$:

$$\lambda_D = \sqrt{\frac{\varepsilon k_B T}{2N_A e^2 I}} \tag{1}$$

where $\varepsilon$ is the dielectric permittivity, $k_B$ the Boltzmann constant, T the temperature, $N_A$ the Avogadro number, e the fundamental electronic charge and I the ionic strength of the electrolyte. Physiological fluids, such as blood, plasma and serum, are replete with salts with ionic strength values in the range of 135-140 mM and, at these concentrations, their Debye length is smaller than 1 nm. In a typical DNA hybridization reaction over a sensor, negative charges are added or an associated change in pH follows when a target DNA strand (1-10 nm) undergoes hybridization with a capture probe functionalized on the sensor surface. However, most of these charges will likely be outside the Debye length as described in equation (1). As a result, surface charges residing on the biomolecules cannot actively participate in modulating the gate voltage of the FET[22-24]. In order to maximize both signal and sensitivity, it is essential to minimize the ion concentration near the surface so that the largest fraction of the molecular charge from the target can be transferred to the device.

Given these fundamental limitations, sensing methods have often resorted to low ionic strength buffers[7], either by performing the entire binding-sensing steps at low strength or using more complex sample handling systems for swapping the diluting and sensing buffers[25], both of which are accompanied by loss of sensitivity due to viability and low binding efficiency[26,27]. Microfluidic preconcentration through capture and release scheme[28] (from concentrated to dilute buffers) using antibodies functionalized over microstructure arrays improves selectivity. Reconfigurable gating methods have opened up possibilities to control ionic conduction in field-effect nanochannel devices[29], but those methods also work best at low ionic strengths (<1 mM). Even as systematic protocols for proper choice of biolinkers have been developed and reported for sensing with nanowires[30-32], their monolayer thickness (5-10 Å) is comparable with the Debye length and has adverse implications for detecting the target charges. Novel workarounds have included engineering of antibody capture fragments[33] that bind the analytes closer to the surface to facilitate improved charge transduction for detection from physiological samples. Alternatively, more complex, highly non-linear schemes of high-frequency AC measurement use electroosmotic mixing to perturb the region around biomolecular dipoles[34]. Our approach is to alleviate the shielding issues and simplify measurements by devising a scheme for localized desalting over the FET sensor and simultaneous gating of the FET sensor. An elegant solution would be to use DC electric fields to adsorb these excess ions within the EDL capacitance of a charged surface in solution. This has been previously demonstrated and discussed in large scale seawater desalination technologies, such as capacitive deionization[35-37] and electrodialysis[38]. In order to minimize side effects such as redox reactions, and gas bubbling and heating[39] that occur under strong forcing fields due to overpotentials, we can design the desalting scheme to work well below the electrolysis limit in a limited volume.

Additionally, an important advantage of the desalting electrodes is that they can act as compact reference electrodes. Generally, the ISFET biosensor includes a (bulky) reference electrode for gate biasing. However, it will be beneficial to localize the reactions for maximum efficacy and sensitivity using on-chip electrodes. Van den Berg et al.[40], demonstrated miniaturized Ag/AgCl reference electrodes for ISFET pH sensors, but their performance was strongly limited by uniformity issues as well as the electrolytes that were used for realization of the reference electrodes. Issues associated with gate biasing through noble metal electrodes have also been studied[41]. Although these electrodes polarize upon adsorbing ions and depleting the solution, the apparent solution potential establishes the transistor gate bias, $V_{gate}=\frac{1}{2}(V_{desalting1}+V_{desalting2})$, to enable simultaneous detection of molecular charge during the desalting process itself.

An important consideration pertains to the time-scale of desalting pulses so that the sensor responds appropriately. Following the desalting step, when the gate voltage is applied, sensing must be completed within time limits of ion back-diffusion. The latter follows a timescale of $\tau=L^2/2D$, where, L is the characteristic separation length and D the ion diffusivity. With L ranging from 10-100 μm and D≈$10^{-9}$ m²/s, back-diffusion occurs within seconds of turning off the polarizing field[42]. Thus, it is vital to combine both desalting and sensing in a single step before the background shielding recurs again. Demonstrate herein is on-chip electrodes and biasing scheme to provide both functions, thereby providing sensing in droplets that can each be independently operated in a multiplexed system.

A schematic of a method for desalting over the FET biosensor, with the use of on-chip desalting and gate electrodes, is shown in FIG. 1. On-chip metal electrodes in the vicinity of the device are used to apply the desalting voltages—$V_{desalting1}$ and $V_{Desalting2}$, as shown in FIG. 1(c). Although these electrodes polarize upon adsorbing ions and depleting the solution, the apparent solution potential establishes the transistor gate bias, $V_{gate}$, to enable simultaneous detection of molecular charge during the desalting process. FIG. 3(a) shows a picture of a sensor surrounded by micro-patterned electrodes and a microinjected droplet in air within which the desalting-sensing experiment is performed. The microdroplet is stabilized with the incorporation of glycerol, which has been shown to prevent evaporation of sub-nanoliter volumes on transistors during heating experiments[43]. Multiple pairs of electrodes can be biased as shown in 2-electrode (FIG. 1(d)) and 4-electrode (FIG. 1(e)) configurations in desalting-sensing is tested.

Ionic shielding at high ionic strengths and large surface potentials: In order to determine the degree of desalting in the droplet at an arbitrary bias $V_e$ and initial condition $n_0$ self consistently, we need to solve for the potential distribution, $\psi$, throughout the volume of the droplet. Consider the case of two opposite polarity electrodes placed in a droplet with volume $V_\Omega$. In a highly ionic system, DC voltages are subject to rapid shielding by adsorption of counter-ions in the electrochemical double layer. The potential distribution and surface charge follow a highly non-linear relationship and the well-known exponential distribution from dilute solution theory breaks down[44]. Steric effects due to finite ion sizes at high ionic strength and large applied voltages are incorporated through Modified Poisson-Boltzmann (MPB) models[45,46], in which the surface potential, $\psi$, decays as follows:

$$\nabla^2 \psi = \frac{zeC_o}{\varepsilon} \frac{2\sinh\left(\frac{ze\psi}{k_BT}\right)}{1 + 2v\sinh^2\left(\frac{ze\psi}{2k_BT}\right)} \quad (2)$$

$$\nabla(\varepsilon\nabla\psi) = -zq(p-n) = -zqn_i \frac{2\sinh\left(\frac{ze\psi}{k_BT}\right)}{1 + 2v\sinh^2\left(\frac{zq\psi}{2k_BT}\right)}$$

where z is the valency, $C_o$ the bulk ionic concentration and $v=a/l_o$ the packing fraction (a ratio of the typical ion size, a, and the interaction length per ion, $l_o$) $v=2n_ia^3$, accounts for the finite size of the ions, a, so that the density does not exceed $1/a^3$. Using equation (2), Kilic et al.[44] have provided accurate calculations to estimate the maximum specific ionic charge per unit area that can be absorbed in the diffuse Debye layer, assuming quasi-equilibrium, from solution on the surface of an electrode by applying a voltage:

$$\sigma_D = -\text{sgn}(\psi_D)2N_AeC_o\lambda_D\sqrt{\frac{2}{v}\ln\left[1 + 2v\sinh^2\left(\frac{F\psi_D}{2RT}\right)\right]} \quad (3)$$

where, F is the Faraday's constant and R the universal gas constant. The goal of our desalting scheme is to maximize absorption of ions within the EDLs of the on-chip electrodes to cause depletion of the bulk and, consequently, to increase the Debye length. The electrode surface area vs. electrolyte volume (SA/V ratio) has implications to sizing the system as discussed further.

Estimation of limiting charge adsorption and droplet size: As electrode dimensions are reduced to the order of 10-100 $\mu$m, we approach a physical limit on the maximum charge that may be absorbed on their surface. Using a $10^4$ $\mu$m$^2$ electrode surface, an estimate from equation (3) of the maximum charge that may be absorbed in the EDL at various surface potentials is shown across a range of initial ionic strengths in FIG. 40(a). In these calculations, we choose non-Faradaic surface potentials in order to avoid coupled effects, asymmetry, gas bubbles and heating from electrochemical reactions. At low (micromolar) ionic strength, we observe that charge absorption follows the exponential, weakly non-linear Guoy-Chapman-Stern theory for point charges, but deviates strongly as ion size effect becomes increasingly prominent at higher concentrations. As a result, in the 1-100 mM range, which is especially relevant for biomolecular sensing, the maximum ionic charge that can be stored within the EDL saturates to a limiting value as observed in FIG. 40(a).

Corresponding to this estimated charge, we estimate an equivalent droplet size that can be depleted to 1% of its initial ionic strength through surface absorption with this desalting method. By depleting the bulk of the electrolyte to 1% of its initial ionic strength, the Debye length is effectively increased by a factor of 10 so that a typical 100 mM system, with $\lambda_D=1$ nm, will now mimic a 1 mM system, with apparent $\lambda_D\approx10$ nm, to include the effect of bound surface charges within this envelop. Assuming a circular footprint and 45° contact angle, this droplet size—the radius of its contact circle on the chip—is mapped as a function of both ionic strength and desalting voltage in FIG. 2(b). From this calculation, the largest droplet of 100 mM electrolyte, subject to electronic desalting at 1 V over $10^4$ $\mu$m$^2$ electrodes, that can be depleted for 10-fold increase in $\lambda_D$ is ca. 45 $\mu$m in diameter—which limits the volume size to sub-nanoliter droplets. However, establishing a solution potential within such a tiny droplet would be practically impossible through a large conventional reference electrode, even using a Luggin-Haber capillary. As far as sensing is concerned, this serves as the motivation to design a novel biasing scheme: one that uses the on-chip electrodes for the dual purpose of electronic desalting as well as gate biasing in order to facilitate FET sensing in a droplet.

Numerical calculations of ion density profiles in droplets: The ionic charge distribution within a droplet can be determined numerically using the composite diffuse layer model[44]. We solve the two-dimensional Poisson equation for the potential distribution, $\phi$, within the droplet, as follows:

$$-\nabla(\varepsilon\nabla\phi)=p-n \quad (4)$$

The ionic distribution is assumed to follow the Boltzmann distribution, where $n_i$ is the minimum ionic density in the droplet, and p and n are the respective positive/negative ion densities. The system is modeled for a symmetric 1:1 electrolyte. In order to account for the finite size of the ions, especially due to crowding near the electrodes at very high concentration, we restricted the maximum ion density in this compact layer to $1/a^3$, where a is the limiting minimum ionic separation. Details of the numerical model are summarized in FIG. 41. For simplicity, we consider only the salt ions and neglect the contribution of H$^+$ and OH$^-$ ions. Equation (2) is highly nonlinear and no general solution is known in a complex geometrical system such as a droplet placed on rectangular electrodes. We therefore adopt a numerical model that provides considerable insight into the desalting properties of the system. The numerical model (FIG. 41) solves equation (2) for a symmetric 1:1 electrolyte (z=1) and implements the right hand side of equation (2) as two discrete functions (equations (5) and (6)). An iterative solution of equations (4) and (7), subject to the boundary condition (equation (8)), determines $\psi$.

FIGS. 40(c) and (d) show the negative ion density within a 300 pL droplet for 1 $\mu$M and 10 $\mu$M initial concentrations, respectively, at an applied desalting bias of 1 V (refer to supplemental material for additional figures). For an unbiased droplet, the concentration throughout the droplet is uniform so that $n(x,y)=p(x,y)=n_0$, where $n_0$ is the ionic concentration. However, with desalting bias, a large fraction of the positive and negative ions from droplet bulk accumulate onto the negative and positive polarity electrodes, respectively. This causes a substantial decrease in n and p from the center of the droplet. FIG. 40(e) shows $n_i$ as a function of $n_0$ for different applied desalting bias. The degree of desalting improves dramatically as the applied bias is increased from 0 to 1 V for lower salt concentrations. However, as the salt concentration increases, the desalting effect reduces due to substantial potential drop near the electrodes where the ionic density is maximum. With the given droplet volume and electrode area, a desalting bias of 1 V can still reduce the salt concentration by almost 50% for 1 mM concentration.

Substrate preparation: All experiments are performed using foundry fabricated CMOS FET devices (TSMC, Taiwan), with an extended gate architecture. On-chip platinum electrodes were defined, with a 1000 Å thick metal-2 layer ensuring adequate step coverage around the sensor through conventional photolithography, evaporation and lift-off procedures. All surface treatment chemicals are purchased from Sigma-Aldrich Corp., MO, USA. During each experiment, prior to the electrolyte loading/exchange step, the chips are degreased and cleaned with oxygen plasma treatment in a diener benchtop RIE system (Thierry Corp., MI USA). Surface functionalization and dye attachment for visual desalting experiments are discussed below.

Solution preparation and pH adjustment: Salt solutions of various ionic strengths are prepared by diluting from a stock 1×PBS buffer using deionized (DI) water from a MilliQ Advantage A Water Purification System (EMD Millipore, MA, USA). In each case, after dilution by a factor of 10, 34% by volume of a 50% DI water/glycerol mixture is added to obtain a final concentration of 13.5% glycerol in order to stabilize the droplet and prevent evaporation. Finally, NaOH is titrated from 1M stock solution to adjust the pH to 7.0 and the resulting ionic strength was noted in each case. Below 1 mM concentration (1000-fold or greater dilutions from stock) we observe that the total ionic strength is overloaded by NaOH addition during pH adjustment, thus the 1 mM system was chosen as the lower limit. The pH adjustment step is specifically incorporated to offset any interference occurring from the native pH response of the on-chip Ti/Pt-electrodes as well as the SNARF-5F dye experiments in order to equalize the baseline fluorescent response across ionic strengths.

Experimental testing: For microdroplet experiments, 0.5-1.5 nL size droplets (including 13.5% added glycerol) are spotted using an IM-300 programmable microinjector (Narishige, Japan), with a 7 μm diameter glass needle tip mounted on a X-Y-Z micrometer stage for precise positioning of the droplet. Bulk solution experiments are performed within a PDMS well that is loaded with 200-300 μL of the electrolyte. Electrical characterization of FET devices and desalting measurements were performed using a Keithley 4200-SCS 4-Channel Parameter Analyzer (Keithley Instruments Inc., OH, USA).

RESULTS AND DISCUSSION: FET characterization in microdroplets using on-chip gate electrode.

Figure 42:
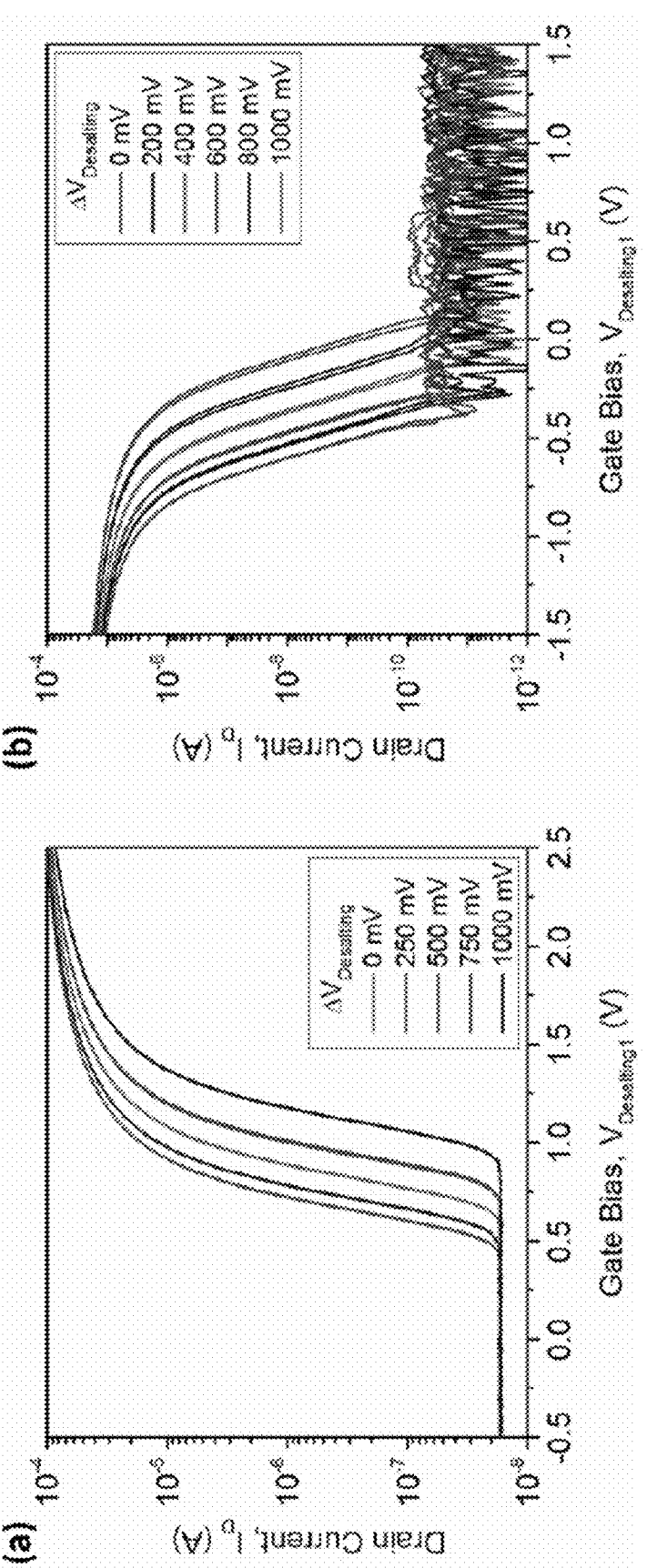
FIG. 42. FET gating with on-chip dual metal electrodes. Electrical characteristics of (a) NMOS and (b) PMOS devices (W/L=2 µm/0.3 µm) measured using the on-chip metal electrodes for gating while simultaneously desalting in a <1 nL droplet. The desalting electrodes are both swept with a fixed desalting offset voltage between them, while source-drain bias is held constant ($|I_{DS}|$=100 mV). Curves are plotted with respect to $V_{Desalting1}$ to observe threshold voltage shifts consistent with the desalting bias. (c) and (d) show device stability between identical $I_D$-$V_G$ sweeps before and after a constant gate bias experiment in each case.
Figure 42:
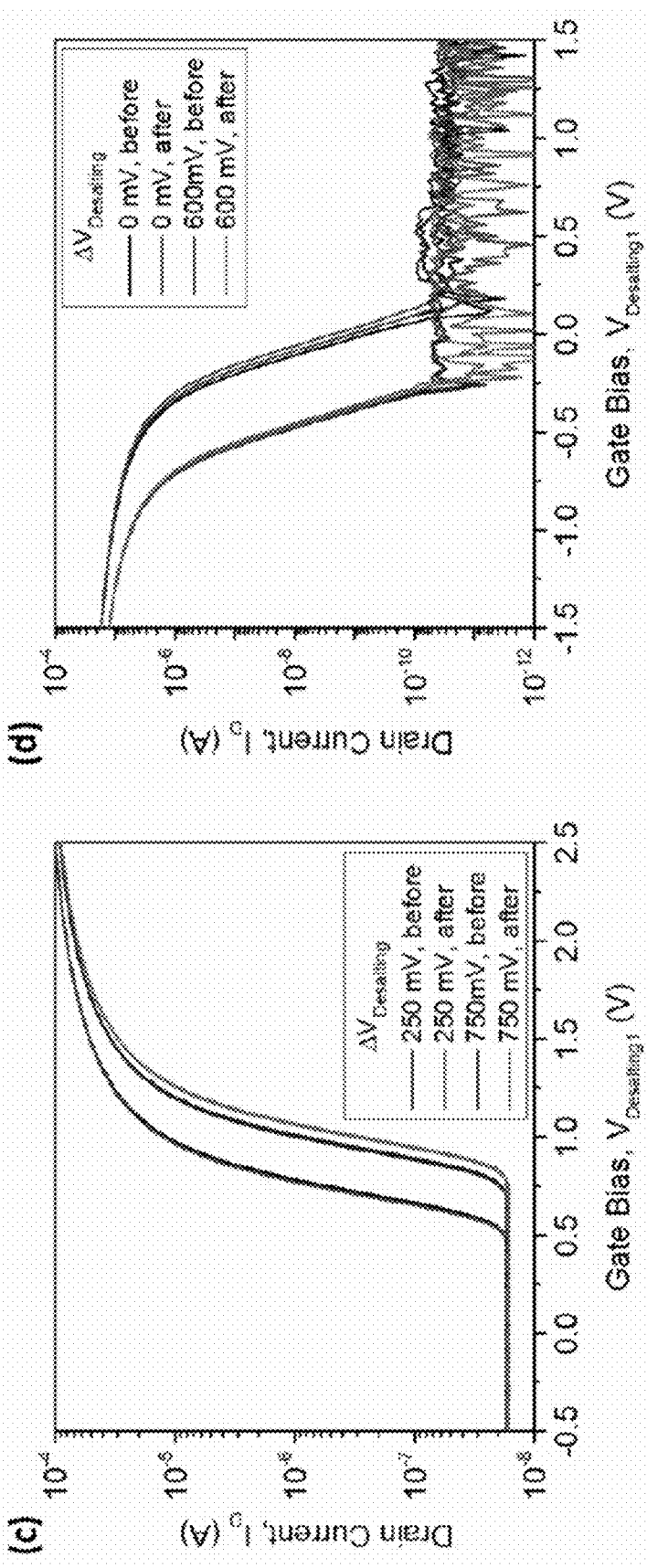

FIG. 42 shows the FET transfer characteristics for both NMOS and PMOS devices when the on-chip Ti/Pt electrodes were used to bias the devices within micro-spotted (<1 nL) droplets. In these experiments, both of the on-chip electrodes are swept at a constant rate of 20 mV/step over the operating range of the FET device as measured earlier in bulk using a leak-free reference electrode (Warner Instruments, CT, USA). $V_{Desalting1}$ is biased over the range of −0.5

Figure 43:
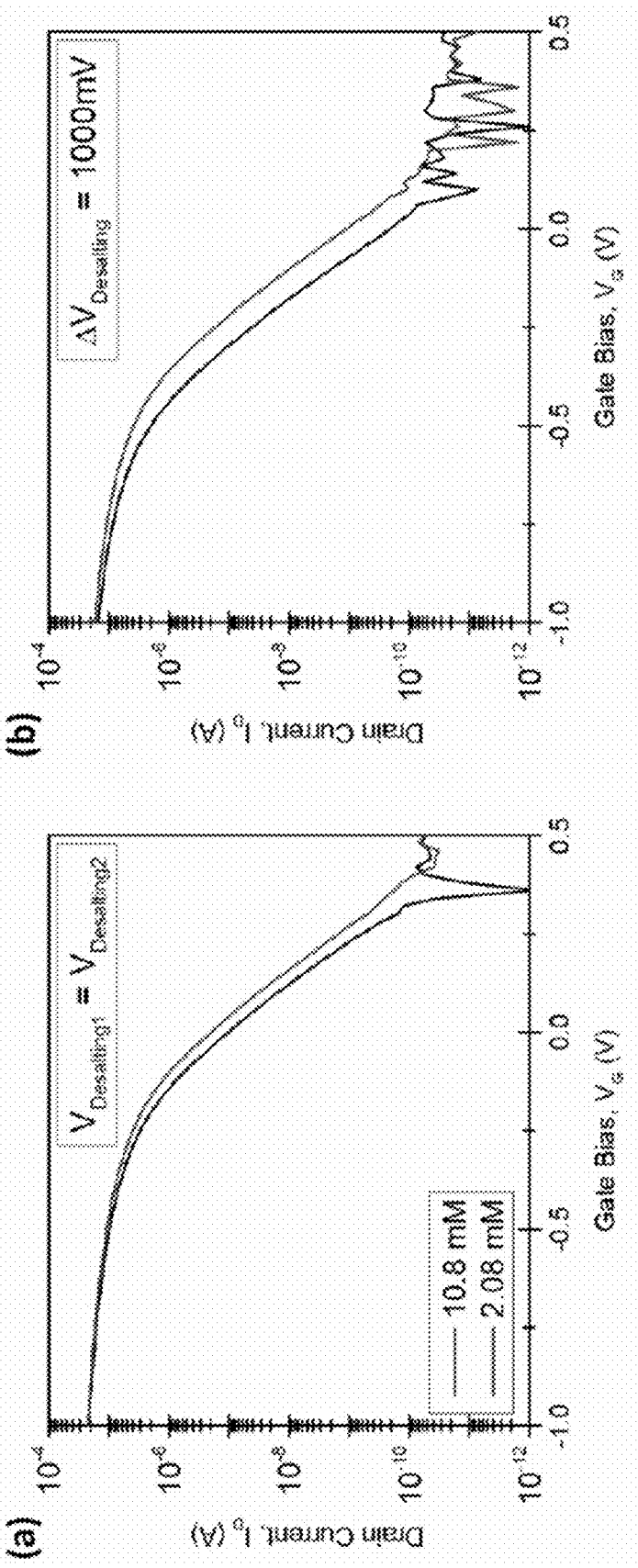
FIG. 43. ISFET response measured using on-chip metal gate electrodes while simultaneously desalting in a microspotted droplet (ca. 500 pL volume). (a: without desalting) and (b: 1 V desalting bias) $I_D$-$V_G$ curves when both the on-chip electrodes are swept such that the apparent gate potential is the same in both cases. (c) $I_D$-t chronoamperograms for the droplet when a constant 1 V desalting bias is applied between the on-chip electrodes. (d) Ionic current decay measured between the on-chip electrodes in the 10.8 mM droplet at various desalting voltages during the FET experiments.
Figure 43:
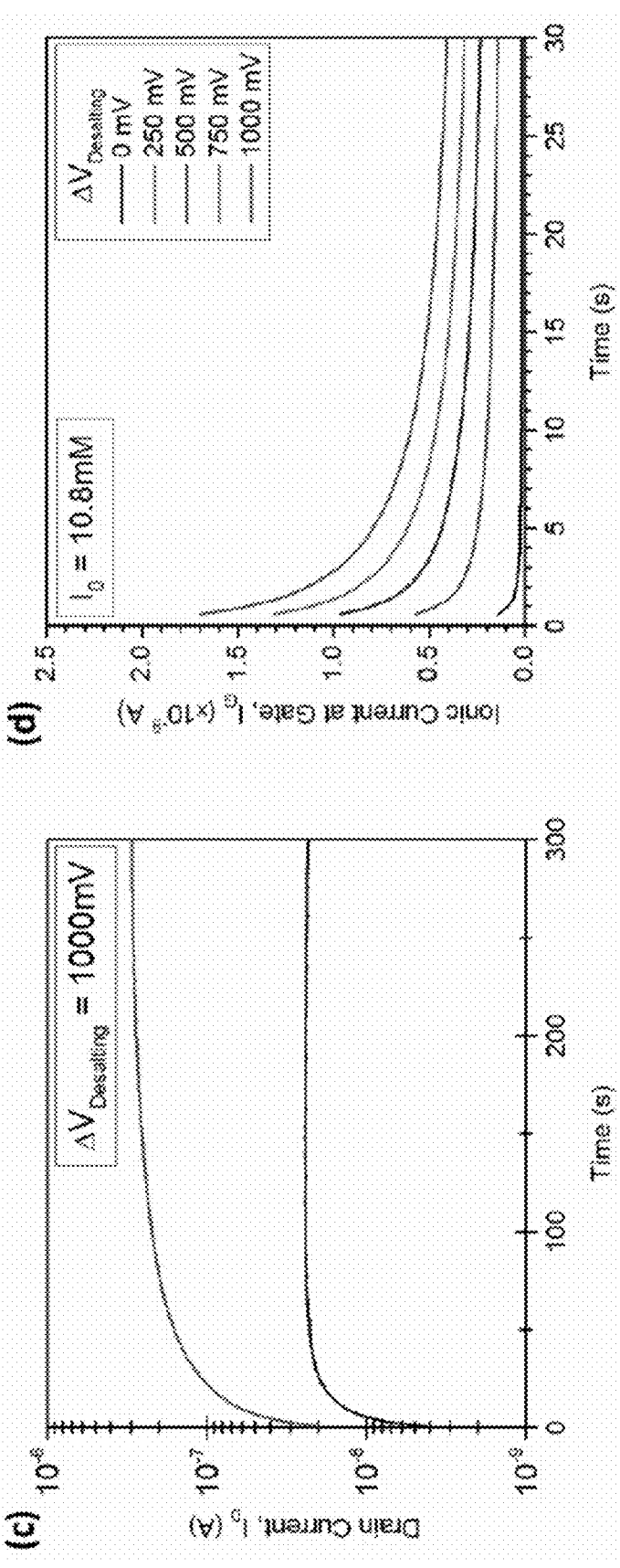

V to 2.5 V for NMOS and 1.5 V to −1.5 V for PMOS devices. A fixed offset voltage lag is maintained with respect to $V_{Desalting1}$ for sweeping $V_{Desalting2}$ in order to introduce simultaneous desalting. The FET is cycled between off-on-off states for 5 cycles in each case, with ample time for ions to equilibrate between experiments. As seen in FIGS. 42(a) and (b), the on-chip electrodes provide stable gating conditions for conduction through FETs. With each step in the desalting bias, we observe that the characteristic curve is shifted by a corresponding value that follows the apparent gate potential established in the bulk of the droplet (FIG. 1(c)). Hereafter, we refer to this apparent gate potential as the gate bias, $V_G$, and device characteristics in subsequent experiments are plotted against this value in FIG. 43. FIGS. 42(c) and (d) show device characteristics before and after a continuous experiment during which the FETs are turned on with a constant gate bias, along with the corresponding desalting bias in each case for 5 min. The desalting process does not cause any apparent irreversibility that may interfere adversely with the FET sensing, and the devices are stable from drift issues between experiments.

Simultaneous desalting and ISFET operation in a droplet: Having obtained stable gating characteristics across the 0-1 V range of desalting bias using the on-chip electrodes, we analyze the effect of desalting on device response. Within the sub-nanoliter microspotted droplets (500 pL by volume, stabilized with 13.5% glycerol), $V_{Desalting1}$ and $V_{Desalting2}$ are biased symmetrically about $V_G$. As depicted in FIGS. 43(a) and (b) respectively, we compare the FET response using both on-chip electrodes without desalting and with 1 V desalting bias. In FIG. 43(c), the drain current trace is plotted for each droplet at 1 V desalting bias during 5 min experiments following the $I_D$-$V_G$ test. While we do not observe significant salt depletion at physiological condition in the 100 mM droplet, the desalting effect became apparent below 10 mM ionic strength. In these micro-droplet experiments, the device response between the salts overlapped when both on-chip electrodes were at the same bias (FIG. 43(a), $V_{Desalting1}$=$V_{Desalting2}$=$V_G$; $\Delta V_{Desalting}$=0). However, we observe shifts in the characteristics when the device is swept with a 1 V desalting bias between the on-chip electrodes (FIG. 43(b)). We again observed an order of magnitude shift in $I_D$-t response (FIG. 43(c)) during 1 V desalting, with the change in ionic environment around the FET and the apparent increase in $\lambda_D$. In contrast with bulk scale systems of the order of several microliters, device response strongly tracked the ionic depletion of the background when the volume is species limited.

FIG. 43(d) shows ionic current measured at various desalting voltages through the on-chip electrode in a 10.8 mM microdroplet during the FET operation. As the electrodes absorb salts in the EDLs through capacitive charging, the ionic current sharply decays over time and tracks the flow of ions as they are depleted from the droplet. The current flow between the on-chip electrode pair mirrored each other and we do not observe any leakage current while the FET is simultaneously biased. The total ionic charge separated during this process is calculated and correlated with the predicted desalting capacity at various biasing conditions. This is further discussed along with other visualization experiments of the desalting process in information provided below.

Desalting at high-ionic concentration: The maximum volume of droplet that can be desalted to a fraction f of the original ionic concentration ($n_0$) with an electrode bias of $V_e$ for a given electrode area $A_e$ is given by:

$$V_{max} = A_e \left( \frac{8\sqrt{f}}{1-f} \lambda_0 \sinh^2\left(\frac{eV_b}{4k_BT}\right) + \frac{l_c}{n_0 a^3(1-f)} \right) \quad (5)$$

For an applied bias, $V_e$, we can also obtain, analytically, an estimate of the surface charge density, $\sigma_e$, absorbed within the EDL over the electrodes (refer Appendix for detailed derivation) as follows:

$$\sigma_e = 4qn_0\lambda_0\sqrt{f} \sinh\left(\frac{qV_b}{2k_BT}\right) + \frac{ql_c}{a^3}$$

where $l_c$ denotes the thickness of the compact layer maximum ion density i.e. $1/a^3$, $\lambda_0$ is the initial debye length for the background ionic concentration, and $$V_c = \frac{k_BT}{e} \log\left(\frac{1}{fn_0a^3}\right)$$

is the critical voltage after which the ionic charge starts to accumulate in the compact layer. The voltage appearing across the Boltzmann layer, $V_b=V_c$ for $V_e>V_c$, or $V_b=V_e$ for $V_e \leq V_c$. Below the critical voltage, all the charge resides within the Boltzmann layer and hence $l_c \rightarrow 0$. The accumulated charge density in Boltzmann layer increases as $$\exp\left(\frac{eV_e}{2k_BT}\right).$$

However, as the bias increases beyond the critical voltage, charge begins to accumulate in the compact layer and $$l_c \approx 2\lambda_0 \sqrt{n_0 a^3 \frac{qV_e}{kT}}.$$

For small ionic concentration, the critical voltage is large and hence, the droplet bulk is considerably desalted. For large ionic concentrations, however, $V_c$ is very small and charge accumulation is forced to occur within the compact layer while desalting the droplet. Since, the thickness of this compact layer is weakly dependent on the applied bias (i.e. $\sqrt{V_e}$), this leads to substantially lower desalting at high salt concentrations (~100 mM).

FIG. 44 shows the ratio of droplet volume to electrode area that is required for desalting the droplet to a fraction, f=0.5 of its original concentration. For desalting of small ionic concentrations (0.1 mM), droplet volume to area ratio can be considerably large (>100 µm). However, in order to desalt large ionic concentrations below the formal potential, the droplet volume to electrode ratio must be small. For example, for a 100 µm×100 µm electrode, sub-pL liter droplets should be deposited for effective desalting at high ionic concentrations (~100 mM). In order to achieve substantial desalting at high ionic concentration, two approaches can be used: 1) an increase in the volume/area ratio by using super-hydrophilic surfaces with shallow droplets (~1 µm height) over the electrodes, or 2) for a given volume of droplet, increasing the surface area for salt adsorption through nanotextured electrodes.

Background salt excess in solution is a fundamental limiting factor in the performance of label-free biosensors for molecular detection. We have demonstrated that on-chip electrodes that manipulate the salt environment around a FET provides localized desalting to overcome shielding issues for improved sensitivity, as well as establish stable potential in solution for simultaneous device gating as a workaround for back-diffusion during a sensing experiment. Volumetric limitation of the desalting capacity adds the requirement of having to do so in a droplet and making this approach more synergistic with digital droplet based assays[47]. However, increasing the area of the on-chip electrodes with nanostructured metal surface for ion absorption will drive the desalting effect to further increase the Debye length around the sensor to maximize the device sensitivity. Notwithstanding evaporation issues, the droplet-scale approach allows sensing in smaller analyte quantities. Combined with droplet microfluidic methods, the ability to integrate and individually address an array of FETs will facilitate high throughput multiplexed detection. More importantly, desalting with the transistor-in-droplet platform provides an elegant solution for biosensing at physiological conditions—an important aspect for POC applications.

Figure 46:
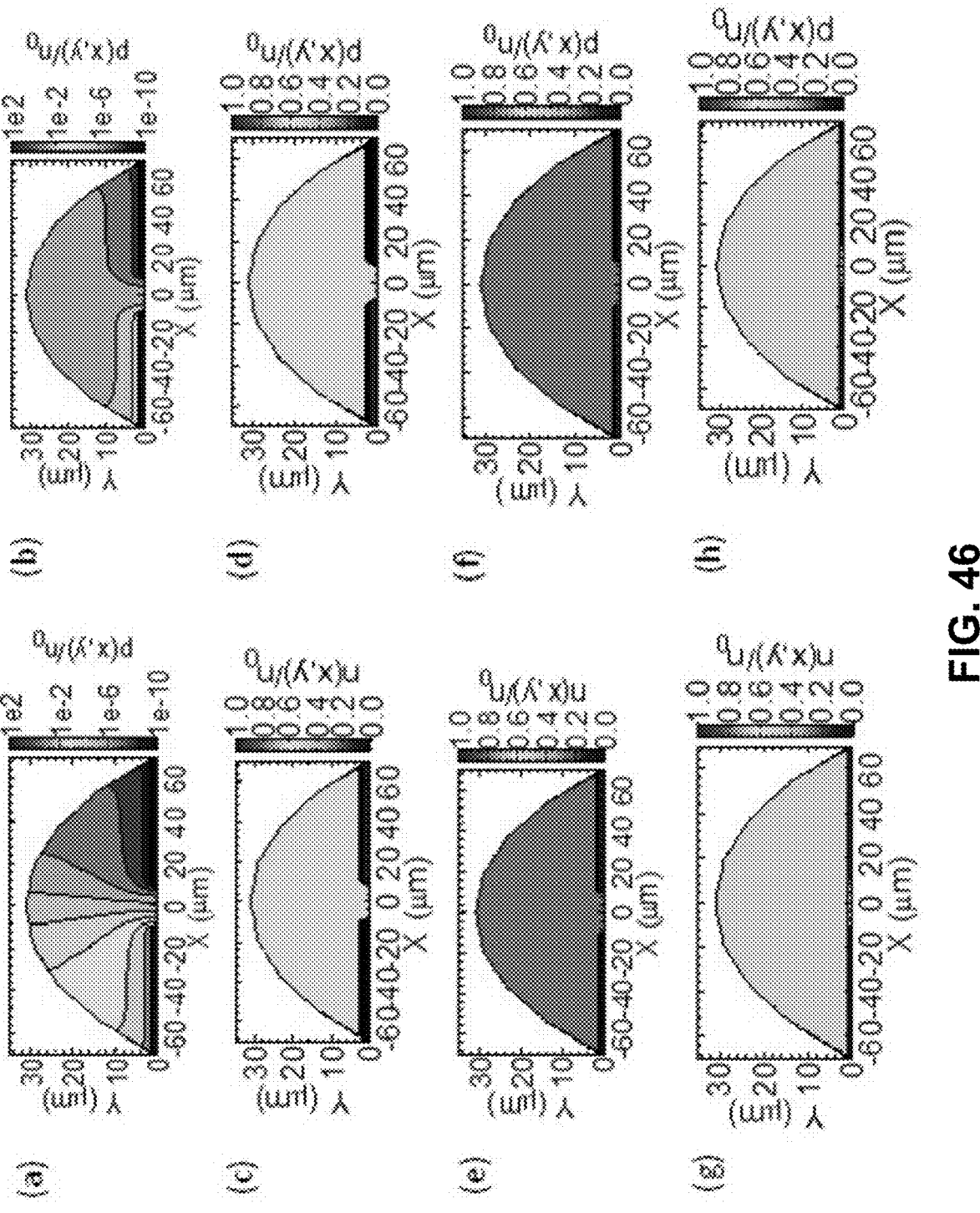
FIG. 46. Distribution of positive ions in (a) 1 µM and (b) 10 µM concentration droplet for a desalting bias of 1 V. (c: negative) and (d: positive) ion distributions for 1 µM at 0.4

Independent examination of the desalting effect in droplets is carried out by fluorescent imaging of an immobilized dye (SNARF-5F), in response to ion separation and partitioning over the device. Details of surface functionalization and dye activation for attachment are discussed below. Numerically simulated ion concentration profiles in droplets during desalting, as a function of applied DC bias, are shown in FIG. 46. Experimentally measured ionic current and charge separation with the EDL is depicted in FIG. 47. Desalting electrode placement and configurations play a crucial role in redistributing salts around the device. The response, with respect to both ionic strength and desalting bias, was characterized for both 4-electrode and 2-electrode configurations (see FIGS. 48 and 49). Maximizing the electrode surface available for desalting is crucial for extending the ion depletion to the 10-100 mM system. Dye calibration, negative dye controls, and desalting control experiments in bulk well and DI water are shown in FIGS. 50-53.

ANALYTICAL MODEL: The potential profile within a droplet can be estimated analytically based on Kilic et al.'s 1-D compact charge model[44]. Consider a droplet placed on two opposite polarity electrodes.

Based on ionic charge conservation:

$$\int_\Omega n_0 dV = \int_{\Omega_{1/2}} n(\vec{r}) + p(\vec{r}) dV \quad (A1)$$

where $n(\vec{r})$ and $p(\vec{r})$ represent the negative and positive ion distributions, respectively, and $\Omega_{1/2}$ denotes the region with one-half of the droplet volume.

$$n_0 V_\Omega = \int_{\Omega_{\frac{1}{2}}} \left(n(\vec{r}) + p(\vec{r}) - 2n_i\right)dV + \int_{\Omega_{1/2}} 2n_i dV \quad (A2)$$

$$n_0 V_\Omega \approx \frac{l_c A_e}{a^3} + \int_{\Omega_{1/2}} 2n_i\left(\cosh\left(\frac{e\phi}{k_BT}\right) - 1\right)dV + \int_{\Omega_{1/2}} 2n_i dV \quad (A3)$$

If we assume that the double layer is thin, $$\phi(x,y,z) \approx \phi(z) \tag{A4}$$

In the Boltzmann layer, the potential varies as[21]

$$\phi(z) = 4 \, \text{arc} \, \tanh\left(\tanh\left(\frac{u_0}{4}\right) \exp\left(-\frac{z}{\lambda_i}\right)\right) \tag{A5}$$

where $\lambda_i$ is the modified debye length based on the applied desalting bias.

This gives, $$n_0 V_\Omega = \frac{l_c A_e}{a^3} + 8 n_i \lambda_i A_e \sinh^2\left(\frac{eV_b}{4k_B T}\right) + n_i V_\Omega \tag{A6}$$

where, $V_b = V_c = \frac{k_B T}{e} \log\left(\frac{1}{n_i a^3}\right)$ for $V_e > V_c$ and $V_b = V_e$ for $V_e < V_c$.

and the compact layer thickness, $$l_c = \lambda_0 \sqrt{2v_0}\left(-1 + \frac{f v_0}{2} + \sqrt{\left(1 - \frac{f v_0}{2}\right)^2 + \left(\left|\frac{eV_e}{k_B T}\right| - \log\left(\frac{2}{f v_0}\right)\right)}\right) \tag{A7}$$

for $V_e > V_c$ and $l_c = 0$ for $V_e \leq V_c$, with $v_0 = 2 n_0 a^3$ and $f = n_i / n_0$. $n_i$ can be solved for using Eq. (A6) for any ionic concentration, $n_0$, and applied bias $V_e$ for a given electrode area and droplet volume. Further for very large bias, $$\left|\frac{eV_e}{k_B T}\right| \gg 1$$

and hence, the compact layer thickness simplifies to $$l_c \approx \lambda_0 \sqrt{2v_0}\left|\frac{eV_e}{k_B T}\right|.$$

Hence, the maximum droplet volume that can be depleted to a fraction f with a given electrode area is given by $$V_{\Omega,max} = A_e\left(\frac{8\sqrt{f}}{1-f} \lambda_0 \sinh^2\left(\frac{eV_b}{4k_B T}\right) + \frac{1}{n_0 a^3 (1-f)}\right) \tag{A8}$$

References for Example 6

1 Y. Cui, Science 293, 1289 (2001).

2 Y. L. Bunimovich, Y. S. Shin, W.-S. Yeo, M. Amori, G. Kwong, and J. R. Heath, J. Am. Chem. Soc. 128, 16323 (2006).

3 G.-J. Zhang, J. H. Chua, R.-E. Chee, A. Agarwal, and S. M. Wong, Biosens. Bioelectron. 24, 2504 (2009).

4 A. Gao, N. Lu, Y. Wang, P. Dai, T. Li, X. Gao, Y. Wang, and C. Fan, Nano Lett. 12, 5262 (2012).

5 B. R. Dorvel, B. Reddy, J. Go, C. Duarte Guevara, E. Salm, M. A. Alam, and R. Bashir, ACS Nano 6, 6150 (2012).

6 G. Zheng, F. Patolsky, Y. Cui, W. U. Wang, and C. M. Lieber, Nat. Biotechnol. 23, 1294 (2005).

7 E. Stern, R. Wagner, F. J. Sigworth, R. Breaker, T. M. Fahmy, and M. A. Reed, Nano Lett. 7, 3405 (2007).

8 F. Patolsky, G. Zheng, O. Hayden, M. Lakadamyali, X. Zhuang, and C. M. Lieber, Proc. Natl. Acad. Sci. 101, 14017 (2004).

9 F. N. Ishikawa, H.-K. Chang, M. Curreli, H.-I. Liao, C. A. Olson, P.-C. Chen, R. Zhang, R. W. Roberts, R. Sun, R. J. Cote, M. E. Thompson, and C. Zhou, ACS Nano 3, 1219 (2009).

10 B. Reddy, B. R. Dorvel, J. Go, P. R. Nair, O. H. Elibol, G. M. Credo, J. S. Daniels, E. K. C. Chow, X. Su, M. Varma, M. A. Alam, and R. Bashir, Biomed. Microdevices 13, 335 (2011).

11 J.-H. Ahn, S.-J. Choi, J.-W. Han, T. J. Park, S. Y. Lee, and Y.-K. Choi, Nano Lett. 10, 2934 (2010).

12 J.-H. Ahn, J.-Y. Kim, M.-L. Seol, D. J. Baek, Z. Guo, C.-H. Kim, S.-J. Choi, and Y.-K. Choi, Appl. Phys. Lett. 102, 083701 (2013).

13 P. Bergveld, Biosensors 2, 15 (1986).

14 P. Bergveld, Sens. Actuators B Chem. 88, 1 (2003).

15 S. Purushothaman, C. Toumazou, and C.-P. Ou, Sens. Actuators B Chem. 114, 964 (2006).

16 J. M. Rothberg, W. Hinz, T. M. Rearick, J. Schultz, W. Mileski, M. Davey, J. H. Leamon, K. Johnson, M. J. Milgrew, M. Edwards, J. Hoon, J. F. Simons, D. Marran, J. W. Myers, J. F. Davidson, A. Branting, J. R. Nobile, B. P. Puc, D. Light, T. A. Clark, M. Huber, J. T. Branciforte, I. B. Stoner, S. E. Cawley, M. Lyons, Y. Fu, N. Homer, M. Sedova, X. Miao, B. Reed, J. Sabina, E. Feierstein, M. Schorn, M. Alanjary, E. Dimalanta, D. Dressman, R. Kasinskas, T. Sokolsky, J. A. Fidanza, E. Namsaraev, K. J. McKernan, A. Williams, G. T. Roth, and J. Bustillo, Nature 475, 348 (2011).

17 M. Gouy, J Phys Theor Appl 9, 457 (1910).

18 D. L. Chapman, Philos. Mag. Ser. 6 25, 475 (1913).

19 A. V. Delgado, F. Gonzalez-Caballero, R. J. Hunter, L. K. Koopal, and J. Lyklema, Pure Appl. Chem. 77, 1753 (2005).

20 P. Debye and E. Hückel, Phys. Z. 24, 185 (1923).

21 A. J. Bard, Electrochemical Methods: Fundamentals and Applications, 2nd ed (Wiley, New York, 2001).

22 P. R. Nair and M. A. Alam, Appl. Phys. Lett. 88, 233120 (2006).

23 P. R. Nair and M. A. Alam, IEEE Trans. Electron Devices 54, 3400 (2007).

24 M. H. Solrensen, N. A. Mortensen, and M. Brandbyge, Appl. Phys. Lett. 91, 102105 (2007).

25 A. Kim, C. S. Ah, C. W. Park, J.-H. Yang, T. Kim, C.-G. Ahn, S. H. Park, and G. Y. Sung, Biosens. Bioelectron. 25, 1767 (2010).

26 B. Honig and A. Nicholls, Science 268, 1144 (1995).

27 N. K. Rajan, X. Duan, and M. A. Reed, Wiley Interdiscip. Rev. Nanomed. Nanobiotechnol. 5, 629 (2013).

28 E. Stern, A. Vacic, N. K. Rajan, J. M. Criscione, J. Park, B. R. Ilic, D. J. Mooney, M. A. Reed, and T. M. Fahmy, Nat. Nanotechnol. 5, 138 (2009).

29 W. Guan, R. Fan, and M. A. Reed, Nat. Commun. 2, 506 (2011).

30 G.-J. Zhang, G. Zhang, J. H. Chua, R.-E. Chee, E. H. Wong, A. Agarwal, K. D. Buddharaju, N. Singh, Z. Gao, and N. Balasubramanian, Nano Lett. 8, 1066 (2008).

31 B. Dorvel, B. Reddy, I. Block, P. Mathias, S. E. Clare, B. Cunningham, D. E. Bergstrom, and R. Bashir, Adv. Funct. Mater. 20, 87 (2010).

32 B. Dorvel, B. Reddy, and R. Bashir, Anal. Chem. 85, 9493 (2013).

33 R. Elnathan, M. Kwiat, A. Pevzner, Y. Engel, L. Burstein, A. Khatchtourints, A. Lichtenstein, R. Kantaev, and F. Patolsky, Nano Lett. 12, 5245 (2012).

34 G. S. Kulkarni and Z. Zhong, Nano Lett. 12, 719 (2012).

35 T. J. Welgemoed and C. F. Schutte, Desalination 183, 327 (2005).

36 M. Andelman, Sep. Purif. Technol. 80, 262 (2011).

37 O. N. Demirer and C. H. Hidrovo, Microfluid. Nanofluidics (2013).

38 K. N. Mani, J. Membr. Sci. 58, 117 (1991).

39 J.-H. Lee, W.-S. Bae, and J.-H. Choi, Desalination 258, 159 (2010).

40 A. van den Berg, A. Grisel, H. H. van den Vlekkert, and N. F. de Rooij, Sens. Actuators B Chem. 1, 425 (1990).

41 S. Chen and S.-L. Zhang, Anal. Chem. 83, 9546 (2011).

42 P. W. Atkins, Physical Chemistry, 6th ed (Freeman, New York, 1998).

43 E. Salm, C. D. Guevara, P. Dak, B. R. Dorvel, B. Reddy, M. A. Alam, and R. Bashir, Proc. Natl. Acad. Sci. 110, 3310 (2013).

44 M. Kilic, M. Bazant, and A. Ajdari, Phys. Rev. E 75, (2007).

45 Iglic, A. and Kralj-Iglic, V., Electrotec. Rev. Slov. 61, 127 (1994).

46 I. Borukhov, D. Andelman, and H. Orland, Phys. Rev. Lett. 79, 435 (1997).

47 B. J. Hindson, K. D. Ness, D. A. Masquelier, P. Belgrader, N. J. Heredia, A. J. Makarewicz, I. J. Bright, M. Y. Lucero, A. L. Hiddessen, T. C. Legler, T. K. Kitano, M. R. Hodel, J. F. Petersen, P. W. Wyatt, E. R. Steenblock, P. H. Shah, L. J. Bousse, C. B. Troup, J. C. Mellen, D. K. Wittmann, N. G. Erndt, T. H. Cauley, R. T. Koehler, A. P. So, S. Dube, K. A. Rose, L. Montesclaros, S. Wang, D. P. Stumbo, S. P. Hodges, S. Romine, F. P. Milanovich, H. E. White, J. F. Regan, G. A. Karlin-Neumann, C. M. Hindson, S. Saxonov, and B. W. Colston, Anal. Chem. 83, 8604 (2011).

SNARF-5F dye functionalization: The HfO2 chip surfaces were functionalized with a monolayer of the SNARF-5F dye molecule using the covalent NHS-amine attachment chemistry. Prior to functionalization, the chips were cleaned and surface activated in a diener oxygen plasma RIE (Thierry Corp., MI USA); this was followed by vapor phase silanization1,2 with 50 μL of 3-aminopropyldimethylethoxysilane (APDMES) in a septum vial, under mild vacuum, at 85° C. for 8-24 hr to achieve a dense monolayer surface with a water contact angle of ca. 45°. Next, using a well-known activation chemistry3, the SNARF-5F dye was modified at room temperature with ethyl(dimethylaminopropyl)carbodiimide (EDC) leaving group and N-hydroxysulfosuccinimide (sulfo-NHS) to form a water soluble intermediate that, subsequently, reacted with the surface amine in 0.5×PBS buffer at pH of 6 for 2 hr. After reaction completion, the chips were rinsed in DI water, dried and stored in darkness in a vacuum dessicator (for short periods only) until experiments. Dye imaging during desalting experiments was performed on a Nikon Eclipse FN-1 Fluorescent Microscope with high NA objectives and 540-580/600-660 nm Y-2-E/C filterblock (Nikon, Japan).

Imaging surface ionic changes during desalting: The desalting effect was tested in microdroplets (ca. 1000 pL volume) through both electrical (FIG. 47) and optical measurements with the ion/pH sensitive SNARF-5F dye (known to fluoresce well within the 5-8 pH range) under neutral pH conditions as a function of ionic concentrations. Each experiment was over a duration of 30-40 seconds, and repeated for 3 different devices in droplets. Charge separation during desalting was calculated by integrating the ionic current over time and the results, in FIG. 47($a$)) are superimposed over theoretical estimate of the EDL capacitor charge (zoomed in from FIG. 1($c$)). The ionic current flow measured between the on-chip electrodes during a desalting experiment in a 10 mM droplet is shown in FIG. 47($b$). The sharp decay is dominated by contribution from capacitive charging of the EDL, and this trend is typical of all the desalting experiments.

FIGS. 48($a$1-$a$4) shows a device within a microdroplet and its fluorescent response at 1V desalting after 30 seconds, with both forward and reverse bias controls. Both 2-electrode (FIGS. 49($c$,$d$)) as well as 4-electrode (FIGS. 48($b$1-$b$4) and FIGS. 49($a$,$b$)) configurations are tested, at 1-100 mM ionic strength range. In the 2-electrode configuration, only the East-West electrode pair are biased, while the North-South pair are floating. In the 4-electrode configuration both pairs are biased such that the North/West and South/East are at $V_{Desalting1}$ and $V_{Desalting2}$ respectively. Measured relative changes in the fluorescent response of the dye to the desalting conditions are analyzed over the sensor region. While this region falls within the bulk of the droplet, a net change in the fluorescence over the gate reflects on the depletion over the region of interest. Based on the biasing configurations, we expect dye partitioning about the vertical (2-electrode) or left diagonal (4-electrode) planes. In both configurations, dye response is consistent with desalting voltage and the effect became particularly apparent at 0.75 V and 1 V, with the −1 V case showing expected reversal symmetry. As visualized from the transverse profile across the plane of symmetry (FIGS. 48($b$1-$b$4)), the on-chip desalting was effective up to the 10.8 mM ionic strength, with no statistically significant change in the droplet bulk at 100 mM. Between the two biasing configurations, using the 4-electrode scheme, by virtue of additional surface area to absorb ions into the EDL, shows increased desalting capacity over the 2-electrode configuration (FIG. 49).

The calibration curve (FIG. 50) shows dye response over the 0.01-100 mM ionic strength range with good dynamic range for pH 5-8. FIG. 51 shows fluorescent response across the electrolytes in negative control experiments from chip regions devoid of surface dye (a) and the dye fluorescence under dry conditions when no ions are present, both without (b) and with desalting bias applied (c). The dye response during 4-electrode desalting experiments in a bulk well (FIG. 52) do not show partitioning and salt depletion over the device—indicative of the overwhelming background excess. Desalting in a DI water droplet (FIG. 53) returns minimal response at ±1 V due to depletion of the trace ionic charges.

Electrochemical Impedance Spectrocopy (EIS) measurements provide a convenient and reliable technique for identifying and analyzing the lengthscales and associated phenomena. Using a low magnitude 10 $mV_{pp}$ signal and a ¾-electrode potentiostat, we can perturb the electrodes across the frequency spectrum without driving any irreversible reactions. With this technique, FIGS. 53($a$-$b$) and 55 were generated and discussed above. Using the impedance magnitude (|Z|) and phase angle (φ) data, it is possible to extract resistive (real, $|Z\cos(\phi))|$) and capacitive (imaginary, $(2\pi f|Z\sin(\phi)|)^{-1}$) components. These components are both plotted in FIG. 55 respectively, for smooth Pt, Pt-black conversion as well as for the CV-treated Pt-black from a single specimen. From both the resistance and capacitance data, we observed that the solution-limiting response at high frequency was independent of the interface whereas the clear scaling of nanostructured surface area came into play at low frequencies. The ratios of capacitances ($C/C_{smooth}$) or resistances ($R_{smooth}/R$) were then used to characterize the extent of surface area enhancement in FIGS. 53(*b*) and 55(*b*) above.

SUPPLEMENTARY REFERENCES

1 B. Dorvel, B. Reddy, I. Block, P. Mathias, S. E. Clare, B. Cunningham, D. E. Bergstrom, and R. Bashir, Adv. Funct. Mater. 20, 87 (2010).
2 B. Dorvel, B. Reddy, and R. Bashir, Anal. Chem. 85, 9493 (2013).
3 Thermo Scientific, (2011).

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a size range, a charge range, an area range, a voltage range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A device for detecting an analyte in a droplet of a sample solution, the device comprising:
   a substrate;
   a field effect transistor (FET) supported by the substrate;
   a plurality of reference electrodes supported by the substrate and positioned in close proximity to the FET and
      a droplet disposed on the plurality of reference electrodes, wherein the plurality of reference electrodes comprises paired reference electrodes, each pair of reference electrodes having a first reference electrode and a second reference electrode opposably facing each other and separated by a separation distance, with the FET positioned between the paired reference electrodes so that the FET and the paired reference electrodes are in a planar configuration relative to the substrate; wherein the plurality of reference electrodes comprise thin patterned metals having a high contact surface area for contacting and supporting the droplet of the sample solution, wherein the separation distance between paired reference electrodes is less than or equal to 30 μm; wherein the droplet has a droplet volume ($V_{droplet}$) of 50 nL or less and the paired reference electrodes have an electrode contact surface area in contact with the droplet (AED) of at least 10000 μm², wherein the droplet is an aqueous droplet and the electrode contact surface area comprises a hydrophilic surface treatment, and wherein a ratio $V_{droplet}$/AED expressed as μm³/μm² is less than or equal to 1 when a desalting bias of 1 V is applied between the paired set of reference electrodes;

an electrical controller configured to electrically bias at least one reference electrode relative to the FET or to another reference electrode and generate a stable FET gate bias, further configured to electronically remove at least a portion of charged ions in the droplet of the sample solution from a sensor area and generate a charged ion depletion region in the sensor area; and an electrical sensor configured to monitor a FET electrical parameter, wherein a change in the electrical parameter corresponds to presence of the analyte in the droplet of the sample solution.

2. The device of claim 1, wherein the FET comprises a nanowire for sensing biological analytes.

3. The device of claim 1, wherein the pair of reference electrodes form a circle having a surface area that substantially corresponds to a droplet contact area.

4. The device of claim 1, comprising two pairs of non-circular reference electrodes that surround the FET.

5. The device of claim 1, further comprising a well that surrounds the FET sensor and at least a portion of the reference electrodes for containing a droplet of sample solution.

6. The device of claim 5, wherein the well defines a well volume, having a well volume that is less than 10 nL to confine a droplet of sample volume around the FET sensor and on the reference electrodes.

7. The device of claim 1, further comprising platinum black on a contact surface of the reference electrodes to increase a surface roughness of the reference electrodes.

8. The device of claim 1, further comprising on a contact surface of the reference electrodes one or more of: electrodeposited platinum black; dendritic silver nanostructures; or platinum black nanotubes.

9. The device of claim 1, wherein the FET further comprises a source electrode and a drain electrode, and the sensor electrically connects the source and drain electrodes.

10. The device of claim 9, wherein the electrical sensor has a functionalized sensing surface to facilitate a binding interaction with the analyte.

11. The device of claim 1, wherein the reference electrodes comprise symmetrically opposed metal electrodes with the FET disposed therebetween, and wherein the symmetrically opposed metal electrodes are substantially semicircular or substantially rectangular opposed electrodes separated by the FET.

12. The device of claim 1, comprising two reference electrode pairs.

13. The device of claim 1, wherein the reference electrodes comprise on-chip platinum electrodes.

14. The device of claim 1, wherein the reference electrodes have a surface configured to adsorb ions and thereby electronically remove at least a portion of charged ions from the sample solution.

15. The device of claim 1, comprising an array of FETs and reference electrodes for multiplexed detection.

16. The device of claim 1, wherein the hydrophilic surface treatment comprises hydrophilic surface activation or self-assembled monolayers.

17. The device of claim 1, wherein electrode contact surface area comprises a surface pattern having a plurality of nanostructures, where the nanostructures have features less than 50 nm.

*     *     *     *     *